United States Patent
Corn et al.

(10) Patent No.: US 11,085,057 B2
(45) Date of Patent: Aug. 10, 2021

(54) COMPOSITIONS AND METHODS FOR MODIFYING A TARGET NUCLEIC ACID

(71) Applicant: The Regents of the University of California, Oakland, CA (US)

(72) Inventors: Jacob E. Corn, Berkeley, CA (US); Christopher D. Richardson, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 172 days.

(21) Appl. No.: 15/773,543

(22) PCT Filed: Dec. 1, 2016

(86) PCT No.: PCT/US2016/064419
§ 371 (c)(1),
(2) Date: May 3, 2018

(87) PCT Pub. No.: WO2017/096041
PCT Pub. Date: Jun. 8, 2017

(65) Prior Publication Data
US 2018/0320202 A1    Nov. 8, 2018

Related U.S. Application Data

(60) Provisional application No. 62/262,189, filed on Dec. 2, 2015.

(51) Int. Cl.
| | | |
|---|---|---|
| *C12N 15/90* | (2006.01) | |
| *C12N 9/22* | (2006.01) | |
| *A61K 31/7088* | (2006.01) | |
| *C12N 15/10* | (2006.01) | |
| *C12N 15/113* | (2010.01) | |
| *C12N 15/11* | (2006.01) | |

(52) U.S. Cl.
CPC ........ *C12N 15/907* (2013.01); *A61K 31/7088* (2013.01); *C12N 9/22* (2013.01); *C12N 15/102* (2013.01); *C12N 15/11* (2013.01); *C12N 15/113* (2013.01); *C12N 2310/20* (2017.05)

(58) Field of Classification Search
CPC .................................................. C12N 15/113
See application file for complete search history.

(56) References Cited

U.S. PATENT DOCUMENTS

| | | |
|---|---|---|
| 2015/0071898 A1 | 3/2015 | Liu et al. |
| 2015/0159174 A1 | 6/2015 | Frendewey et al. |
| 2018/0127787 A1* | 5/2018 | Gurumurthy ............ C12N 9/22 |

FOREIGN PATENT DOCUMENTS

| | | | | |
|---|---|---|---|---|
| WO | WO 2015/013583 | 1/2015 | | |
| WO | WO 2015/030881 | 3/2015 | | |
| WO | WO2015/134812 | * 9/2015 | ........... | C12N 15/113 |
| WO | WO 2015/134812 | 9/2015 | | |

OTHER PUBLICATIONS

Sander et al. (nature biotechnology. Apr. 2014;32(4): 347-355 ) (Year: 2014).*
Arribere, et al.; "Efficient Marker-Free Recovery of Custom Genetic Modifications with CRISPR/Cas9 in *Caenorhabditis elegans*"; Genetics; vol. 198, pp. 837-846 (Nov. 2014).
Inui, et al.; "Rapid generation of mouse models with defined point mutations by the CRISPR/Cas9 system"; Scientific Reports; vol. 4, No. 5396, 8 pages (Jun. 23, 2014).
Maruyama, et al.; "Increasing the efficiency of precise genome editing with CRISPR-Cas9 by inhibition of nonhomologous end joining"; Nature Biotechnology; vol. 33, No. 5, 9 pages (May 2015).
Ran, et al.; "Double Nicking by RNA-Guided CRISPR Cas9 for Enhanced Genome Editing Specificity"; Cell; vol. 154, pp. 1380-1389 (Sep. 12, 2013).
Richardson, et al.; "Enhancing homology-directed genome editing by catalytically active and inactive CRISPR-Cas9 using asymmetric donor DNA"; Nature Biotechnology; vol. 34, No. 3, 7 pages (Mar. 2016).
Wu, et al.; "Correction of a Genetic Disease in Mouse via Use of CRISPR-Cas9"; Cell Stem Cell; vol. 13, pp. 659-662 (Dec. 5, 2013).

\* cited by examiner

*Primary Examiner* — Scott Long
(74) *Attorney, Agent, or Firm* — Bozicevic Field & Francis, LLP; Paula A. Borden

(57) ABSTRACT

The present disclosure provides a system for editing genomic DNA, the system comprising an asymmetric donor DNA template; and methods of editing genomic DNA involving use of an asymmetric donor DNA template. The present disclosure provides a system for editing genomic DNA, the system comprising a Cas9 polypeptide with reduced enzymatic activity; and methods of editing genomic DNA involving use of a Cas9 polypeptide with reduced enzymatic activity.

7 Claims, 42 Drawing Sheets

Specification includes a Sequence Listing.

C - Cas9 / n1 - D10A / n1 - D10A / d - dCas9

FIG. 6

| Figure | Substrate DNA | Nuclease Variants | RNP-DNA | Challenge DNA | Supershift Products |
|---|---|---|---|---|---|
| Fig. 2B | | Cas9 | | | |
| Fig. 2C | | Cas9 | | | |
| Fig. 2D | | Cas9 D10A / H840A dCas9 | | | |
| Fig. 2E | | Cas9 dCas9 | | | |

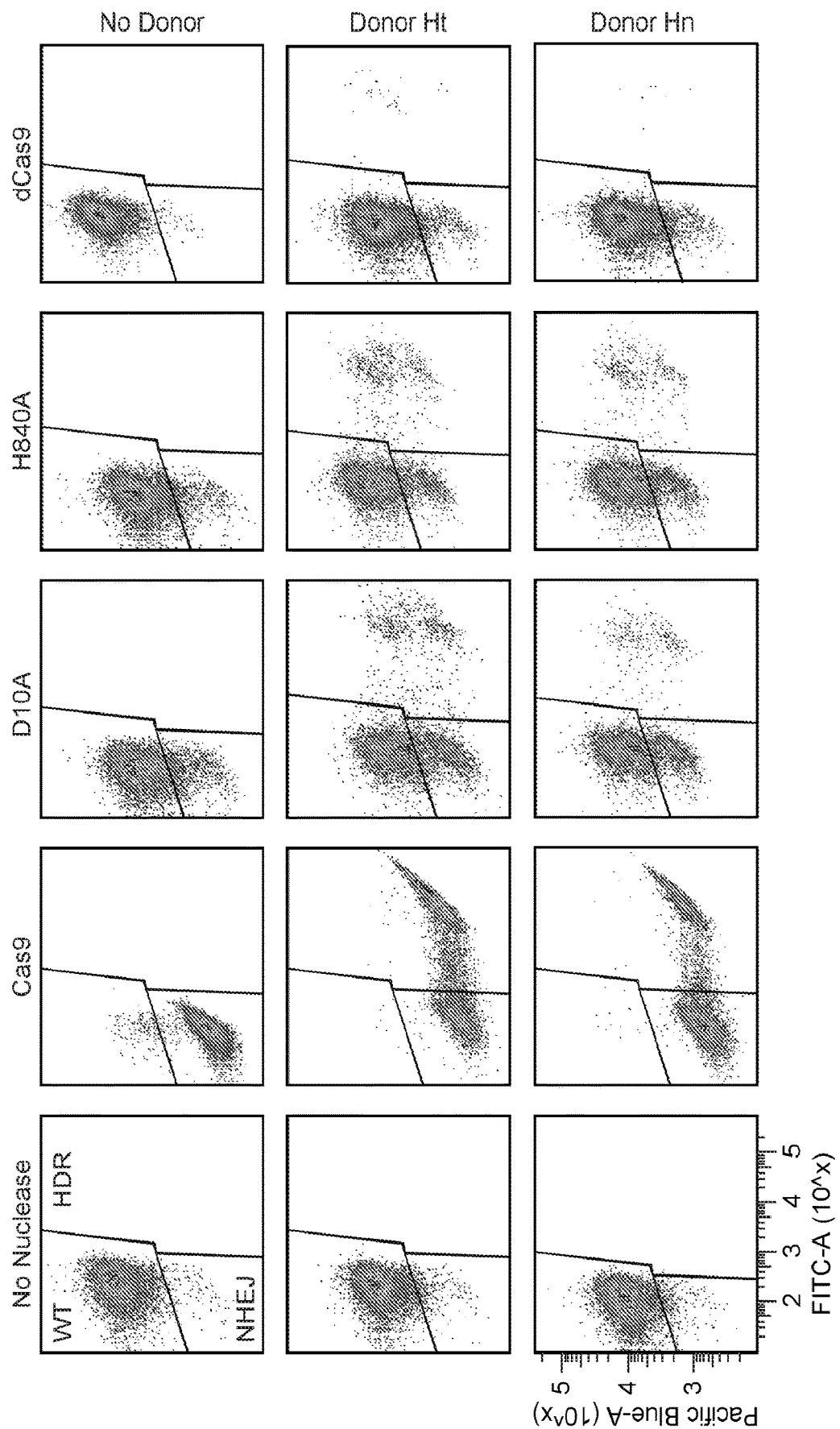

FIG. 17 sgRNA template DNA (protospacer annealing in CAPS)

λ1  ccagtgaattctaatacgactcactatagACGCATAAAGATGAGACGCGt
tttagagctatgctgttttggaaacaaaacagcatagcaagttaaaataa
ggctagtccgttatcaacttgaaaaagtggcaccgagtcggtgcttttt
tg A   ccagtgaattctaatacgactcactataggCCATATCTGTGAGGGAGCCA
gttttagagctatgctgttttggaaacaaaacagcatagcaagttaaaat
aaggctagtccgttatcaacttgaaaaagtggcaccgagtcggtgctttt
tttg 1   ccagtgaattctaatacgactcactataggAGATTCTAAATCCTGCTCCT
gttttagagctatgctgttttggaaacaaaacagcatagcaagttaaaat
aaggctagtccgttatcaacttgaaaaagtggcaccgagtcggtgctttt
tttg B   ccagtgaattctaatacgactcactataGGTCTCGTAGTCCGGTGAGCgt
tttagagctatgctgttttggaaacaaaacagcatagcaagttaaaataa
ggctagtccgttatcaacttgaaaaagtggcaccgagtcggtgcttttt
tg 2   ccagtgaattctaatacgactcactataGGGGAGAGTGACCGGCTCACgt
tttagagctatgctgttttggaaacaaaacagcatagcaagttaaaataa
ggctagtccgttatcaacttgaaaaagtggcaccgagtcggtgcttttt
tg AAVS1-F  ggatcctaatacgactcactatagTGTCCCTAGTGGCCCCACTGgtttta
gagctagaaatagcaagttaaaataaggctagtccgttatcaacttgaaa
aagtggcaccgagtcggtgctttttt AAVS1-R  ggatcctaatacgactcactatagACAGTGGGGCCACTAGGGACgtttta
gagctagaaatagcaagttaaaataaggctagtccgttatcaacttgaaa
aagtggcaccgagtcggtgctttttt BFP-L2   ggatcctaatacgactcactatagGCTGAAGCACTGCACGCCATgtttta
gagctagaaatagcaagttaaaataaggctagtccgttatcaacttgaaa
aagtggcaccgagtcggtgctttttt EMX1-F   ggatcctaatacgactcactatagCGATGTCACCTCCAATGACTgtttta
gagctagaaatagcaagttaaaataaggctagtccgttatcaacttgaaa
aagtggcaccgagtcggtgctttttt

FIG. 17 (Cont.)

Substrate DNA (protospacer, bold; PAM, bold underline)

S1　　　　AGCAGAAATCTCTGCTGACGCATAAAGATGAGACGCTGGAGTACAAACGT
　　　　　CAGCT

S1　　　　AGCAGAAATCTCTGCTGACGCATAAAGATGAGACGCTcGAGTACAAACGT
pam-　　　CAGCT

S1　　　　tatgagatgactctgaGACGCATAAAGATGAGACGCTGGgtgacctaacg
nh-　　　　taaga

D1　　　　GGGATGGGAGGTGTG**AAGATTCTAAATCCTGCTCCTTGGCTCCCTCACAG
　　　　　ATATGGCCCAGAAAGGCCGCGGTCTCGTAGTCCGGTGAGCCGGTCACTCT
　　　　　CCCC**GAGGTCCCACACTCCC

BFP　　　 ATGGTGAGCAAGGGCGAGGAGCTGTTCACCGGGGTGGTGCCCATCCTGGT
　　　　　CGAGCTGGACGGCGACGTAAACGGCCACAAGTTCAGCGTGTCCGGCGAGG
　　　　　GCGAGGGCGATGCCACCTACGGCAAGCTGACCCTGAAGTTCATCTGCACC
　　　　　ACCGGCAAGCTGCCCGTGCCCTGGCCCACCCTCGTGACCACCCTGA**CCCA
　　　　　TGGCGTGCAGTGCTTCAGC**CGCTACCCCGACCACATGAAGCAGCACGACT
　　　　　TCTTCAAGTCCGCCATGCCCGAAGGCTACGTCCAGGAGCGCACCATCTTC
　　　　　TTCAAGGACGACGGCAACTACAAGACCCGCGCCGAGGTGAAGTTCGAGGG
　　　　　CGACACCCTGGTGAACCGCATCGAGCTGAAGGGCATCGACTTCAAGGAGG
　　　　　ACGGCAACATCCTGGGGCACAAGCTGGAGTACAACTACAACAGCCACAAC
　　　　　GTCTATATCATGGCCGACAAGCAGAAGAACGGCATCAAGGTGAACTTCAA
　　　　　GATCCGCCACAACATCGAGGACGGCAGCGTGCAGCTCGCCGACCACTACC
　　　　　AGCAGAACACCCCCATCGGCGACGGCCCCGTGCTGCTGCCCGACAACCAC
　　　　　TACCTGAGCACCCAGTCCAAGCTGAGCAAAGACCCCAACGAGAAGCGCGA
　　　　　TCACATGGTCCTGCTGGAGTTCGTGACCGCCGCCGGGATCACTCTCGGCA
　　　　　TGGACGAGCTGTACAAG

EMX1　　　AATGGGGAGGACATCGATGTCACCTCCAATGACTAGGGTGGGCAACCACA

AAVS1　　 TCTGTCACCAATCCTGTCCCTAGTGGCCCCACTGTGGGGTGGAGGGGACA

Donor

At　　　　CCTGAAGTTCATCTGCACCACCGGCAAGCTGCCCGTGCCCTGGCCCACCC
(CR236)　 TCGTGACCACCCTGACGTACGGCGTGCAGTGCTTCAGCCGCTACCCCGAC
　　　　　CACATGAAGCAGCACGACTT

FIG. 17 (Cont.)

An
(CR237)
AAGTCGTGCTGCTTCATGTGGTCGGGGTAGCGGCTGAAGCACTGCACGCC
GTACGTCAGGGTGGTCACGAGGGTGGGCCAGGGCACGGGCAGCTTGCCGG
TGGTGCAGATGAACTTCAGG

Bt
(CR238)
CCCTCGTGACCACCCTGACGTACGGCGTGCAGTGCTTCAGCCGCTACCCC
GACCACATGA

Bn
(CR239)
TCATGTGGTCGGGGTAGCGGCTGAAGCACTGCACGCCGTACGTCAGGGTG
GTCACGAGGG

Ct
(CR254)
CCCTCGTGACCACCCTGACGTACGGCGTGCAGTGCTTCAGCCGCTACCCC
GACCACATGAAGCAGCACGACTT

Cn
(CR255)
AAGTCGTGCTGCTTCATGTGGTCGGGGTAGCGGCTGAAGCACTGCACGCC
GTACGTCAGGGTGGTCACGAGGG

Dt
(CR256)
CCCTCGTGACCACCCTGACGTACGGCGTGCAGTGCTTCAGCCGCTACCCC
GACCACATGAAGCAGCACGACTTCTTCAAGTCCGCCATGCCCGAAGGCTA
CGTCCAGGAGCGC

Dn
(CR257)
GCGCTCCTGGACGTAGCCTTCGGGCATGGCGGACTTGAAGAAGTCGTGCT
GCTTCATGTGGTCGGGGTAGCGGCTGAAGCACTGCACGCCGTACGTCAGG
GTGGTCACGAGGG

Et
(CR278)
CCTGAAGTTCATCTGCACCACCGGCAAGCTGCCCGTGCCCTGGCCCACCC
TCGTGACCACCCTGACGTACGGCGTGCAGTGCTTCAGCCGCTACCCC

En
(CR279)
GGGGTAGCGGCTGAAGCACTGCACGCCGTACGTCAGGGTGGTCACGAGGG
TGGGCCAGGGCACGGGCAGCTTGCCGGTGGTGCAGATGAACTTCAGG

Ft
(CR280)
CCTGAAGTTCATCTGCACCACCGGCAAGCTGCCCGTGCCCTGGCCCACCC
TCGTGACCACCCTGACGTACGGCGTGCAGTGCTTCAG

Fn
(CR281)
CTGAAGCACTGCACGCCGTACGTCAGGGTGGTCACGAGGGTGGGCCAGGG
CACGGGCAGCTTGCCGGTGGTGCAGATGAACTTCAGG

Gt
(CR252)
CCTGAAGTTCATCTGCACCACCGGCAAGCTGCCCGTGCCCTGGCCCACCC
TCGTGACCACCCTGACGTACGGCGTGCAGTGCTTCAGCCGCTACCCCGAC
CACATGA

Gn
(CR253)
TCATGTGGTCGGGGTAGCGGCTGAAGCACTGCACGCCGTACGTCAGGGTG
GTCACGAGGGTGGGCCAGGGCACGGGCAGCTTGCCGGTGGTGCAGATGAA
CTTCAGG

FIG. 17 (Cont.)

Ht (CR282)
GCCACCTACGGCAAGCTGACCCTGAAGTTCATCTGCACCACCGGCAAGCT
GCCCGTGCCCTGGCCCACCCTCGTGACCACCCTGACGTACGGCGTGCAGT
GCTTCAGCCGCTACCCCGACCACATGA

Hn (CR283)
TCATGTGGTCGGGGTAGCGGCTGAAGCACTGCACGCCGTACGTCAGGGTG
GTCACGAGGGTGGGCCAGGGCACGGGCAGCTTGCCGGTGGTGCAGATGAA
CTTCAGGGTCAGCTTGCCGTAGGTGGC

Tt (CR276)
TGTCCGGCGAGGGCGAGGGCGATGCCACCTACGGCAAGCTGACGCTGAAG
TTCATCTGCACCACCGGCAAGCTGCCGGTGCCCTGGCCCACCCTCGTGAC
CACCCTGACGTACGGCGTGCAGTGCTTCAGCCGCTACCCCGACGACATGA
AGCAGCACGACTTCTTCAAGTCCGCCATGCCCGAAGGCTACGTCCAG

Tn (CR277)
CTGGACGTAGCCTTCGGGCATGGCGGACTTGAAGAAGTCGTGCTGCTTCA
TGTCGTCGGGGTAGCGGCTGAAGCACTGCACGCCGTACGTCAGGGTGGTC
ACGAGGGTGGGCCAGGGCACCGGCAGCTTGCCGGTGGTGCAGATGAACTT
CAGCGTCAGCTTGCCGTAGGTGGCATCGCCCTCGCCCTCGCCGGACA

In (CR287)
AGGCCAATGGGGAGGACATCGATGTCACCTCCAATGacatgtGTGGGCAACC
ACAAACCCACGAGGGCAGAGTGCTGCTTGCTGCTGGCCAGGCCCCTGCGTGG
GCCCAAGCTGGACTCTGGCCACT It (CR288)
AGTGGCCAGAGTCCAGCTTGGGCCCACGCAGGGGCCTGGCCAGCAGCAAGCA
GCACTCTGCCCTCGTGGGTTTGTGGTTGCCCACacatgtCATTGGAGGTGAC
ATCGATGTCCTCCCCATTGGCCT Jn (CR289)
AGGCCAATGGGGAGGACATCGATGTCACCTCCAATGacatgtGTGGGCAACC
ACAAACCC Jt (CR290)
GGGTTTGTGGTTGCCCACacatgtCATTGGAGGTGACATCGATGTCCTCCCC
ATTGGCCT qPCR Primers
ACT1B-Fwd   CTGGAACGGTGAAGGTGACA
ACT1B-Rev   AAGGGACTTCCTGTAACAACGC AAVS1L-Fwd  CAGAAAAGCCCCATCCTTAGGC
AAVS1L-Rev  CGGGCAGGTCACGCATC
AAVS1R-Fwd  GCAGCAAACATGCTGTCCTG
AAVS1R-Rev  TTGCTTTCTTTGCCTGGACAC

FIG. 18 pCR1002 Sequence T7promoter-His10-MBP-TEV-Cas9
(T7 Promoter to T7 Terminator)

```
ATGAAATCTTCTCACCATCACCATCACCATCACCATCACCATGGTTCTTCTATGAAAAT
CGAAGAAGGTAAACTGGTAATCTGGATTAACGGCGATAAAGGCTATAACGGTCTCGCTG
AAGTCGGTAAGAAATTCGAGAAGATACCGGAATTAAAGTCACCGTTGAGCATCCGGAT
AAACTGGAAGAGAAATTCCCACAGGTTGCGGCAACTGGCGATGGCCCTGACATTATCTT
CTGGGCACACGACCGCTTTGGTGGCTACGCTCAATCTGGCCTGTTGGCTGAAATCACCC
CGGACAAAGCGTTCCAGGACAAGCTGTATCCGTTTACCTGGGATGCCGTACGTTACAAC
GGCAAGCTGATTGCTTACCCGATCGCTGTTGAAGCGTTATCGCTGATTTATAACAAAGA
TCTGCTGCCGAACCCGCCAAAAACCTGGGAAGAGATCCCGGCGCTGGATAAGAACTGA
AGCGAAAGGTAAGAGCGCGCTGATGTTCAACCTGCAAGAACCGTACTTCACCTGGCCG
CTGATTGCTGCTGACGGGGGTTATGCGTTCAAGTATGAAAACGGCAAGTACGACATTAA
AGACGTGGGCGTGGATAACGCTGGCGCGAAAGCGGGTCTGACCTTCCTGGTTGACCTGA
TTAAAAACAAACACATGAATGCAGACACCGATTACTCCATCGCAGAAGCTGCCTTTAAT
AAAGGCGAAACAGCGATGACCATCAACGGCCCGTGGGCATGGTCCAACATCGACACCAG
CAAAGTGAATTATGGTGTAACGGTACTGCCGACCTTCAAGGGTCAACCATCCAAACCGT
TCGTTGGCGTGCTGAGCGCAGGTATTAACGCCGCCAGTCCGAACAAAGAGCTGGCAAAA
GAGTTCCTCGAAAACTATCTGCTGACTGATGAAGGTCTGGAAGCGGTTAATAAAGACAA
ACCGCTGGGTGCCGTAGCGCTGAAGTCTTACGAGGAAGAGTTGGCGAAAGATCCACGTA
TTGCCGCCACTATGGAAAACGCCCAGAAAGGTGAAATCATGCCGAACATCCCGCAGATG
TCCGCTTTCTGGTATGCCGTGCGTACTGCGGTGATCAACGCCGCCAGCGGTCGTCAGAC
TGTCGATGAAGCCCTGAAAGACGCGCAGACTAATTCGAGCTCGAACAACAACAACAATA
ACAATAACAACAACCTCGGGATCGAGGAAAACCTGTACTTCCAATCCAATGCAATGGAT
AAGAAATACTCAATAGGCTTAGATATCGGCACAAATAGCGTCGGATGGGCGGTGATCAC
TGATGAATATAAGGTTCCGTCTAAAAAGTTCAAGGTTCTGGGAAATACAGACCGCCACA
GTATCAAAAAAATCTTATAGGGGCTCTTTTATTTGACAGTGGAGAGACAGCGGAAGCG
ACTCGTCTCAAACGGACAGCTCGTAGAAGGTATACACGTCGGAAGAATCGTATTTGTTA
TCTACAGGAGATTTTTTCAAATGAGATGGCGAAAGTAGATGATAGTTTCTTTCATCGAC
TTGAAGAGTCTTTTTTGGTGGAAGAAGACAAGAAGCATGAACGTCATCCTATTTTTGGA
AATATAGTAGATGAAGTTGCTTATCATGAGAAATATCCAACTATCTATCATCTGCGAAA
AAAATTGGTAGATTCTACTGATAAAGCGGATTTGCGCTTAATCTATTTGGCCTTAGCGC
ATATGATTAAGTTTCGTGGTCATTTTTTGATTGAGGGAGATTTAAATCCTGATAATAGT
GATGTGGACAAACTATTTATCCAGTTGGTACAAACCTACAATCAATTATTTGAAGAAAA
CCCTATTAACGCAAGTGGAGTAGATGCTAAAGCGATTCTTTCTGCACGATTGAGTAAAT
CAAGACGATTAGAAAATCTCATTGCTCAGCTCCCCGGTGAGAAGAAAATGGCTTATTT
GGGAATCTCATTGCTTTGTCATTGGGTTTGACCCCTAATTTTAAATCAAATTTTGATTT
GGCAGAAGATGCTAAATTACAGCTTTCAAAAGATACTTACGATGATGATTTAGATAATT
TATTGGCGCAAATTGGAGATCAATATGCTGATTTGTTTTTGGCAGCTAAGAATTTATCA
GATGCTATTTTACTTTCAGATATCCTAAGAGTAAATACTGAAATAACTAAGGCTCCCCT
ATCAGCTTCAATGATTAAACGCTACGATGAACATCATCAAGACTTGACTCTTTTAAAAG
CTTTAGTTCGACAACAACTTCCAGAAAAGTATAAAGAAATCTTTTTTGATCAATCAAAA
AACGGATATGCAGGTTATATTGATGGGGGAGCTAGCCAAGAAGAATTTTATAAATTTAT
CAAACCAATTTTAGAAAAAATGGATGGTACTGAGGAATTATTGGTGAAACTAAATCGTG
AAGATTTGCTGCGCAAGCAACGGACCTTTGACAACGGCTCTATTCCCCATCAAATTCAC
TTGGGTGAGCTGCATGCTATTTTGAGAAGACAAGAAGACTTTTATCCATTTTTAAAAGA
CAATCGTGAGAAGATTGAAAAAATCTTGACTTTTCGAATTCCTTATTATGTTGGTCCAT
```

FIG. 18 (Cont.)

TGGCGCGTGGCAATAGTCGTTTTGCATGGATGACTCGGAAGTCTGAAGAAACAATTACC
CCATGGAATTTTGAAGAAGTTGTCGATAAAGGTGCTTCAGCTCAATCATTTATTGAACG
CATGACAAACTTTGATAAAAATCTTCCAAATGAAAAGTACTACCAAAACATAGTTTGC
TTTATGAGTATTTTACGGTTTATAACGAATTGACAAAGGTCAAATATGTTACTGAAGGA
ATGCGAAAACCAGCATTTCTTTCAGGTGAACAGAAGAAAGCCATTGTTGATTTACTCTT
CAAAACAAATCGAAAGTAACCGTTAAGCAATTAAAAGAAGATTATTTCAAAAAAATAG
AATGTTTTGATAGTGTTGAAATTTCAGGAGTTGAAGATAGATTTAATGCTTCATTAGGT
ACCTACCATGATTTGCTAAAAATTATTAAAGATAAAGATTTTTTGGATAATGAAGAAAA
TGAAGATATCTTAGAGGATATTGTTTTAACATTGACCTTATTTGAAGATAGGGAGATGA
TTGAGGAAAGACTTAAAACATATGCTCACCTCTTTGATGATAAGGTGATGAAACAGCTT
AAACGTCGCCGTTATACTGGTTGGGACGTTTGTCTCGAAAATTGATTAATGGTATTAG
GGATAAGCAATCTGGCAAAACAATATTAGATTTTTGAAATCAGATGGTTTTGCCAATC
GCAATTTTATGCAGCTGATCCATGATGATAGTTTGACATTTAAAGAAGACATTCAAAAA
GCACAAGTGTCTGGACAAGGCGATAGTTTACATGAACATATTGCAAATTTAGCTGGTAG
CCCTGCTATTAAAAAAGGTATTTTACAGACTGTAAAAGTTGTTGATGAATTGGTCAAAG
TAATGGGGCGGCATAAGCCAGAAAATATCGTTATTGAAATGGCACGTGAAAATCAGACA
ACTCAAAAGGGCCAGAAAAATTCGCGAGAGCGTATGAAACGAATCGAAGAAGGTATCAA
AGAATTAGGAAGTCAGATTCTTAAAGAGCATCCTGTTGAAAATACTCAATTGCAAATG
AAAAGCTCTATCTCTATTATCTCCAAAATGGAAGAGACATGTATGTGGACCAAGAATTA
GATATTAATCGTTTAAGTGATTATGATGTCGATCACATTGTTCCACAAAGTTTCCTTAA
AGACGATTCAATAGACAATAAGGTCTTAACGCGTTCTGATAAAAATCGTGGTAAATCGG
ATAACGTTCCAAGTGAAGAAGTAGTCAAAAGATGAAAAACTATTGGAGACAACTTCTA
AACGCCAAGTTAATCACTCAACGTAAGTTTGATAATTTAACGAAAGCTGAACGTGGAGG
TTTGAGTGAACTTGATAAAGCTGGTTTTATCAAACGCCAATTGGTTGAAACTCGCCAAA
TCACTAAGCATGTGGCACAAATTTTGGATAGTCGCATGAATACTAAATACGATGAAAAT
GATAAACTTATTCGAGAGGTTAAAGTGATTACCTTAAAATCTAAATTAGTTTCTGACTT
CCGAAAAGATTTCCAATTCTATAAAGTACGTGAGATTAACAATTACCATCATGCCCATG
ATGCGTATCTAAATGCCGTCGTTGGAACTGCTTTGATTAAGAAATATCCAAAACTTGAA
TCGGAGTTTGTCTATGGTGATTATAAAGTTTATGATGTTCGTAAAATGATTGCTAAGTC
TGAGCAAGAAATAGGCAAAGCAACCGCAAAATATTTCTTTTACTCTAATATCATGAACT
TCTTCAAAACAGAAATTACACTTGCAAATGGAGAGATTCGCAAACGCCCTCTAATCGAA
ACTAATGGGGAAACTGGAGAAATTGTCTGGGATAAAGGGCGAGATTTTGCCACAGTGCG
CAAAGTATTGTCCATGCCCCAAGTCAATATTGTCAAGAAACAGAAGTACAGACAGGCG
GATTCTCCAAGGAGTCAATTTTACCAAAAGAAATTCGGACAAGCTTATTGCTCGTAAA
AAAGACTGGGATCCAAAAAAATATGGTGGTTTTGATAGTCCAACGGTAGCTTATTCAGT
CCTAGTGGTTGCTAAGGTGGAAAAAGGGAAATCGAAGAAGTTAAAATCCGTTAAAGAGT
TACTAGGGATCACAATTATGGAAAGAAGTTCCTTTGAAAAAATCCGATTGACTTTTTA
GAAGCTAAGGATATAAGGAAGTTAAAAAGACTTAATCATTAAACTACCTAAATATAG
TCTTTTTGAGTTAGAAACGGTCGTAAACGGATGCTGGCTAGTGCCGGAGAATTACAAA
AAGGAAATGAGCTGGCTCTGCCAAGCAAATATGTGAATTTTTATATTTAGCTAGTCAT
TATGAAAAGTTGAAGGGTAGTCCAGAAGATAACGAACAAAAACAATTGTTTGTGGAGCA
GCATAAGCATTATTTAGATGAGATTATTGAGCAAATCAGTGAATTTTCTAAGCGTGTTA
TTTTAGCAGATGCCAATTTAGATAAAGTTCTTAGTGCATATAACAAACATAGAGACAAA
CCAATACGTGAACAAGCAGAAAATATTATTCATTTATTTACGTTGACGAATCTTGGAGC
TCCCGCTGCTTTTAAATATTTTGATACAACAATTGATCGTAAACGATATACGTCTACAA
AAGAAGTTTTAGATGCCACTCTTATCCATCAATCCATCACTGGTCTTTATGAAACACGC
ATTGATTTGAGTCAGCTAGGAGGTGACTAATAACATTGGAAGTGGATAACGGATCCGCG
ATCGCGGCGCGCCACCTGGTGGCCGGCCGGTACCACGCGTGCGCGCTGATCCGGCTGCT

FIG. 18 (Cont.)

AACAAAGCCCGAAAGGAAGCTGAGTTGGCTGCTGCCACCGCTGAGCAATAACTAGCATA
ACCCCTTGGGGCCTCTAAACGGGTCTTGAGGGGTTTTTTG pCR1003 Sequence T7promoter-His10-MBP-TEV-dCas9
(T7 Promoter to T7 Terminator)
TAATACGACTCACTATAGGGAGACCACAACGGTTTCCCTCTAGTGCCGGCTCCGGAGAG
CTCTTTAATTAAGCGGCCGCCCTGCAGGACTCGAGTTCTAGAAATAATTTTGTTTAACT
TTAAGAAGGAGATATACATATGAAATCTTCTCACCATCACCATCACCATCACCATCACC
ATGGTTCTTCTATGAAAATCGAAGAAGGTAAACTGGTAATCTGGATTAACGGCGATAAA
GGCTATAACGGTCTCGCTGAAGTCGGTAAGAAATTCGAGAAAGATACCGGAATTAAAGT
CACCGTTGAGCATCCGGATAAACTGGAAGAGAAATTCCCACAGGTTGCGGCAACTGGCG
ATGGCCCTGACATTATCTTCTGGGCACACGACCGCTTTGGTGGCTACGCTCAATCTGGC
CTGTTGGCTGAAATCACCCCGGACAAAGCGTTCCAGGACAAGCTGTATCCGTTTACCTG
GGATGCCGTACGTTACAACGGCAAGCTGATTGCTTACCCGATCGCTGTTGAAGCGTTAT
CGCTGATTTATAACAAAGATCTGCTGCCGAACCCGCCAAAAACCTGGGAAGAGATCCCG
GCGCTGGATAAGAACTGAAAGCGAAGGTAAGAGCGCGCTGATGTTCAACCTGCAAGA
ACCGTACTTCACCTGGCCGCTGATTGCTGCTGACGGGGGTTATGCGTTCAAGTATGAAA
ACGGCAAGTACGACATTAAAGACGTGGGCGTGGATAACGCTGGCGCGAAAGCGGGTCTG
ACCTTCCTGGTTGACCTGATTAAAAACAAACACATGAATGCAGACACCGATTACTCCAT
CGCAGAAGCTGCCTTTAATAAAGGCGAAACAGCGATGACCATCAACGGCCCGTGGGCAT
GGTCCAACATCGACACCAGCAAAGTGAATTATGGTGTAACGGTACTGCCGACCTTCAAG
GGTCAACCATCCAAACCGTTCGTTGGCGTGCTGAGCGCAGGTATTAACGCCGCCAGTCC
GAACAAAGAGCTGGCAAAAGAGTTCCTCGAAAACTATCTGCTGACTGATGAAGGTCTGG
AAGCGGTTAATAAAGACAAACCGCTGGGTGCCGTAGCGCTGAAGTCTTACGAGGAAGAG
TTGGCGAAAGATCCACGTATTGCCGCCACTATGGAAAACGCCCAGAAAGGTGAAATCAT
GCCGAACATCCCGCAGATGTCCGCTTTCTGGTATGCCGTGCGTACTGCGGTGATCAACG
CCGCCAGCGGTCGTCAGACTGTCGATGAAGCCCTGAAAGACGCGCAGACTAATTCGAGC
TCGAACAACAACAACAATAACAATAACAACAACCTCGGGATCGAGGAAAACCTGTACTT
CCAATCCAATGCAATGGATAAGAAATACTCAATAGGCTTAGCTATCGGCACAAATAGCG
TCGGATGGGCGGTGATCACTGATGAATATAAGGTTCCGTCTAAAAAGTTCAAGGTTCTG
GGAAATACAGACCGCCACAGTATCAAAAAAATCTTATAGGGGCTCTTTTATTTGACAG
TGGAGAGACAGCGGAAGCGACTCGTCTCAAACGGACAGCTCGTAGAAGGTATACACGTC
GGAAGAATCGTATTTGTTATCTACAGGAGATTTTTCAAATGAGATGGCGAAAGTAGAT
GATAGTTTCTTTCATCGACTTGAAGAGTCTTTTTTGGTGGAAGAAGACAAGAAGCATGA
ACGTCATCCTATTTTTGGAAATATAGTAGATGAAGTTGCTTATCATGAGAAATATCCAA
CTATCTATCATCTGCGAAAAAATTGGTAGATTCTACTGATAAAGCGGATTTGCGCTTA
ATCTATTTGGCCTTAGCGCATATGATTAAGTTTCGTGGTCATTTTTGATTGAGGGAGA
TTTAAATCCTGATAATAGTGATGTGGACAAACTATTTATCCAGTTGGTACAAACCTACA
ATCAATTATTTGAAGAAAACCCTATTAACGCAAGTGGAGTAGATGCTAAAGCGATTCTT
TCTGCACGATTGAGTAAATCAAGACGATTAGAAAATCTCATTGCTCAGCTCCCCGGTGA
GAAGAAAATGGCTTATTTGGGAATCTCATTGCTTTGTCATTGGGTTTGACCCCTAATT
TTAAATCAAATTTTGATTTGGCAGAAGATGCTAAATTACAGCTTTCAAAAGATACTTAC
GATGATGATTTAGATAATTTATTGGCGCAAATTGGAGATCAATATGCTGATTTGTTTTT
GGCAGCTAAGAATTTATCAGATGCTATTTTACTTTCAGATATCCTAAGAGTAAATACTG
AAATAACTAAGGCTCCCCTATCAGCTTCAATGATTAAACGCTACGATGAACATCATCAA
GACTTGACTCTTTTAAAAGCTTTAGTTCGACAACAACTTCCAGAAAAGTATAAAGAAAT
CTTTTTTGATCAATCAAAAAACGGATATGCAGGTTATATTGATGGGGAGCTAGCCAAG
AAGAATTTTATAAATTTATCAAACCAATTTTAGAAAAAATGGATGGTACTGAGGAATTA

FIG. 18 (Cont.)

```
TTGGTGAAACTAAATCGTGAAGATTTGCTGCGCAAGCAACGGACCTTTGACAACGGCTC
TATTCCCCATCAAATTCACTTGGGTGAGCTGCATGCTATTTTGAAGACAAGAAGACT
TTTATCCATTTTTAAAAGACAATCGTGAGAAGATTGAAAAAATCTTGACTTTTCGAATT
CCTTATTATGTTGGTCCATTGGCGCGTGGCAATAGTCGTTTTGCATGGATGACTCGGAA
GTCTGAAGAAACAATTACCCCATGGAATTTTGAAGAAGTTGTCGATAAAGGTGCTTCAG
CTCAATCATTTATTGAACGCATGACAAACTTTGATAAAATCTTCCAAATGAAAAAGTA
CTACCAAAACATAGTTTGCTTTATGAGTATTTTACGGTTTATAACGAATTGACAAAGGT
CAAATATGTTACTGAAGGAATGCGAAAACCAGCATTTCTTTCAGGTGAACAGAAGAAAG
CCATTGTTGATTTACTCTTCAAAACAAATCGAAAAGTAACCGTTAAGCAATTAAAAGAA
GATTATTTCAAAAAATAGAATGTTTTGATAGTGTTGAAATTTCAGGAGTTGAAGATAG
ATTTAATGCTTCATTAGGTACCTACCATGATTTGCTAAAAATTATTAAAGATAAAGATT
TTTTGGATAATGAAGAAATGAAGATATCTTAGAGGATATTGTTTTAACATTGACCTTA
TTTGAAGATAGGGAGATGATTGAGGAAAGACTTAAAACATATGCTCACCTCTTTGATGA
TAAGGTGATGAAACAGCTTAAACGTCGCCGTTATACTGGTTGGGACGTTTGTCTCGAA
AATTGATTAATGGTATTAGGGATAAGCAATCTGGCAAAACAATATTAGATTTTTTGAAA
TCAGATGGTTTTGCCAATCGCAATTTTATGCAGCTGATCCATGATGATAGTTTGACATT
TAAAGAAGACATTCAAAAGCACAAGTGTCTGGACAAGGCGATAGTTTACATGAACATA
TTGCAAATTTAGCTGGTAGCCCTGCTATTAAAAAAGGTATTTTACAGACTGTAAAAGTT
GTTGATGAATTGGTCAAAGTAATGGGGCGGCATAAGCCAGAAAATATCGTTATTGAAAT
GGCACGTGAAAATCAGACAACTCAAAAGGGCCAGAAAAATTCGCGAGAGCGTATGAAAC
GAATCGAAGAAGGTATCAAAGAATTAGGAAGTCAGATTCTTAAAGAGCATCCTGTTGAA
AATACTCAATTGCAAAATGAAAAGCTCTATCTCTATTATCTCCAAAATGGAAGAGACAT
GTATGTGGACCAAGAATTAGATATTAATCGTTTAAGTGATTATGATGTCGATGCCATTG
TTCCACAAAGTTTCCTTAAAGACGATTCAATAGACAATAAGGTCTTAACGCGTTCTGAT
AAAAATCGTGGTAAATCGGATAACGTTCCAAGTGAAGAAGTAGTCAAAAGATGAAAAA
CTATTGGAGACAACTTCTAAACGCCAAGTTAATCACTCAACGTAAGTTTGATAATTTAA
CGAAAGCTGAACGTGGAGGTTTGAGTGAACTTGATAAAGCTGGTTTTATCAAACGCCAA
TTGGTTGAAACTCGCCAAATCACTAAGCATGTGGCACAAATTTTGGATAGTCGCATGAA
TACTAAATACGATGAAATGATAAACTTATTCGAGAGGTTAAAGTGATTACCTTAAAAT
CTAAATTAGTTTCTGACTTCCGAAAAGATTTCCAATTCTATAAAGTACGTGAGATTAAC
AATTACCATCATGCCCATGATGCGTATCTAAATGCCGTCGTTGGAACTGCTTTGATTAA
GAAATATCCAAAACTTGAATCGGAGTTTGTCTATGGTGATTATAAAGTTTATGATGTTC
GTAAAATGATTGCTAAGTCTGAGCAAGAAATAGGCAAAGCAACCGCAAAATATTTCTTT
TACTCTAATATCATGAACTTCTTCAAAACAGAAATTACACTTGCAAATGGAGAGATTCG
CAAACGCCCTCTAATCGAAACTAATGGGGAAACTGGAGAAATTGTCTGGGATAAAGGGC
GAGATTTTGCCACAGTGCGCAAAGTATTGTCCATGCCCCAAGTCAATATTGTCAAGAAA
ACAGAAGTACAGACAGGCGGATTCTCCAAGGAGTCAATTTTACCAAAAGAAATTCGGA
CAAGCTTATTGCTCGTAAAAAGACTGGGATCCAAAAAATATGGTGGTTTTGATAGTC
CAACGGTAGCTTATTCAGTCCTAGTGGTTGCTAAGGTGGAAAAAGGGAAATCGAAGAAG
TTAAAATCCGTTAAAGAGTTACTAGGGATCACAATTATGGAAGAAGTTCCTTTGAAAA
AAATCCGATTGACTTTTTAGAAGCTAAAGGATATAAGGAAGTTAAAAAAGACTTAATCA
TTAAACTACCTAAATATAGTCTTTTTGAGTTAGAAAACGGTCGTAAACGGATGCTGGCT
AGTGCCGGAGAATTACAAAAAGGAAATGAGCTGGCTCTGCCAAGCAAATATGTGAATTT
TTTATATTTAGCTAGTCATTATGAAAGTTGAAGGGTAGTCCAGAAGATAACGAACAAA
AACAATTGTTTGTGGAGCAGCATAAGCATTATTTAGATGAGATTATTGAGCAAATCAGT
GAATTTTCTAAGCGTGTTATTTTAGCAGATGCCAATTTAGATAAAGTTCTTAGTGCATA
TAACAAACATAGAGACAAACCAATACGTGAACAAGCAGAAAATATTATTCATTTATTTA
CGTTGACGAATCTTGGAGCTCCCGCTGCTTTTAAATATTTTGATACAACAATTGATCGT
```

FIG. 18 (Cont.)

AAACGATATACGTCTACAAAAGAAGTTTTAGATGCCACTCTTATCCATCAATCCATCAC
TGGTCTTTATGAAACACGCATTGATTTGAGTCAGCTAGGAGGTGACTAATAACATTGGA
AGTGGATAACGGATCCGCGATCGCGGCGCGCCACCTGGTGGCCGGCCGGTACCACGCGT
GCGCGCTGATCCGGCTGCTAACAAAGCCCGAAAGGAAGCTGAGTTGGCTGCTGCCACCG
CTGAGCAATAACTAGCATAACCCCTTGGGGCCTCTAAACGGGTCTTGAGGGGTTTTTTG pCR1053 Sequence T7promoter-His10-MBP-TEV-Cas9-2NLS
(T7 Promoter to T7 Terminator)
TAATACGACTCACTATAGGGAGACCACAACGGTTTCCCTCTAGTGCCGGCTCCGGAGAG
CTCTTTAATTAAGCGGCCGCCCTGCAGGACTCGAGTTCTAGAAATAATTTTGTTTAACT
TTAAGAAGGAGATATACATATGAAATCTTCTCACCATCACCATCACCATGGTTCTTCTA
TGAAAATCGAAGAAGGTAAACTGGTAATCTGGATTAACGGCGATAAAGGCTATAACGGT
CTCGCTGAAGTCGGTAAGAAATTCGAGAAAGATACCGGAATTAAAGTCACCGTTGAGCA
TCCGGATAAACTGGAAGAGAAATTCCCACAGGTTGCGGCAACTGGCGATGGCCCTGACA
TTATCTTCTGGGCACACGACCGCTTTGGTGGCTACGCTCAATCTGGCCTGTTGGCTGAA
ATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATA
CAAAGATCTGCTGCCGAACCCGCCAAAAACCTGGGAAGAGATCCCGGCGCTGGATAAA
GAACTGAAAGCGAAAGGTAAGAGCGCGCTGATGTTCAACCTGCAAGAACCGTACTTCAC
CTGGCCGCTGATTGCTGCTGACGGGGGTTATGCGTTCAAGTATGAAAACGGCAAGTACG
ACATTAAAGACGTGGGCGTGGATAACGCTGGCGCGAAAGCGGGTCTGACCTTCCTGGTT
GACCTGATTAAAAACAAACACATGAATGCAGACACCGATTACTCCATCGCAGAAGCTGC
CTTTAATAAAGGCGAAACAGCGATGACCATCAACGGCCCGTGGGCATGGTCCAACATCG
ACACCAGCAAAGTGAATTATGGTGTAACGGTACTGCCGACCTTCAAGGGTCAACCATCC
AAACCGTTCGTTGGCGTGCTGAGCGCAGGTATTAACGCCGCCAGTCCGAACAAAGAGCT
GGCAAAAGAGTTCCTCGAAAACTATCTGCTGACTGATGAAGGTCTGGAAGCGGTTAATA
AAGACAAACCGCTGGGTGCCGTAGCGCTGAAGTCTTACGAGGAAGAGTTGGCGAAAGAT
CCACGTATTGCCGCCACTATGGAAAACGCCCAGAAAGGTGAAATCATGCCGAACATCCC
GCAGATGTCCGCTTTCTGGTATGCCGTGCGTACTGCGGTGATCAACGCCGCCAGCGGTC
GTCAGACTGTCGATGAAGCCCTGAAAGACGCGCAGACTAATTCGAGCTCGAACAACAAC
AACAATAACAATAACAACAACCTCGGGATCGAGGAAAACCTGTACTTCCAATCCAATGC
CACCATGGATAAGAAATACTCAATAGGCTTAGATATCGGCACAAATAGCGTCGGATGGG
CGGTGATCACTGATGAATATAAGGTTCCGTCTAAAAAGTTCAAGGTTCTGGGAAATACA
GACCGCCACAGTATCAAAAAAAATCTTATAGGGGCTCTTTTATTTGACAGTGGAGAGAC
AGCGGAAGCGACTCGTCTCAAACGGACAGCTCGTAGAAGGTATACACGTCGGAAGAATC
GTATTTGTTATCTACAGGAGATTTTTTCAAATGAGATGGCGAAAGTAGATGATAGTTTC
TTTCATCGACTTGAAGAGTCTTTTTTGGTGGAAGAAGACAAGAAGCATGAACGTCATCC
TATTTTTGGAAATATAGTAGATGAAGTTGCTTATCATGAGAAATATCCAACTATCTATC
ATCTGCGAAAAAATTGGTAGATTCTACTGATAAAGCGGATTTGCGCTTAATCTATTTG
GCCTTAGCGCATATGATTAAGTTTCGTGGTCATTTTTGATTGAGGGAGATTTAAATCC
TGATAATAGTGATGTGGACAAACTATTTATCCAGTTGGTACAAACCTACAATCAATTAT
TTGAAGAAACCCTATTAACGCAAGTGGAGTAGATGCTAAAGCGATTCTTTCTGCACGA
TTGAGTAAATCAAGACGATTAGAAAATCTCATTGCTCAGCTCCCCGGTGAGAAGAAAAA
TGGCTTATTTGGGAATCTCATTGCTTTGTCATTGGGTTTGACCCCTAATTTTAAATCAA
ATTTTGATTTGGCAGAAGATGCTAAATTACAGCTTTCAAAAGATACTTACGATGATGAT
TTAGATAATTTATTGGCGCAAATTGGAGATCAATATGCTGATTTGTTTTTGGCAGCTAA
GAATTTATCAGATGCTATTTTACTTTCAGATATCCTAAGAGTAAATACTGAAATAACTA

FIG. 18 (Cont.)

```
AGGCTCCCCTATCAGCTTCAATGATTAAACGCTACGATGAACATCATCAAGACTTGACT
CTTTTAAAAGCTTTAGTTCGACAACAACTTCCAGAAAAGTATAAAGAAATCTTTTTTGA
TCAATCAAAAACGGATATGCAGGTTATATTGATGGGGGAGCTAGCCAAGAAGAATTTT
ATAAATTTATCAAACCAATTTTAGAAAAAATGGATGGTACTGAGGAATTATTGGTGAAA
CTAAATCGTGAAGATTTGCTGCGCAAGCAACGGACCTTTGACAACGGCTCTATTCCCCA
TCAAATTCACTTGGGTGAGCTGCATGCTATTTTGAGAAGACAAGAAGACTTTTATCCAT
TTTTAAAAGACAATCGTGAGAAGATTGAAAAAATCTTGACTTTTCGAATTCCTTATTAT
GTTGGTCCATTGGCGCGTGGCAATAGTCGTTTTGCATGGATGACTCGGAAGTCTGAAGA
AACAATTACCCCATGGAATTTTGAAGAAGTTGTCGATAAAGGTGCTTCAGCTCAATCAT
TTATTGAACGCATGACAAACTTTGATAAAAATCTTCCAAATGAAAAGTACTACCAAAA
CATAGTTTGCTTTATGAGTATTTTACGGTTTATAACGAATTGACAAAGGTCAAATATGT
TACTGAAGGAATGCGAAAACCAGCATTTCTTTCAGGTGAACAGAAGAAAGCCATTGTTG
ATTTACTCTTCAAAACAAATCGAAAAGTAACCGTTAAGCAATTAAAAGAAGATTATTTC
AAAAAAATAGAATGTTTTGATAGTGTTGAAATTTCAGGAGTTGAAGATAGATTTAATGC
TTCATTAGGTACCTACCATGATTTGCTAAAAATTATTAAAGATAAAGATTTTTTGGATA
ATGAAGAAATGAAGATATCTTAGAGGATATTGTTTTAACATTGACCTTATTTGAAGAT
AGGGAGATGATTGAGGAAAGACTTAAAACATATGCTCACCTCTTTGATGATAAGGTGAT
GAAACAGCTTAAACGTCGCCGTTATACTGGTTGGGGACGTTTGTCTCGAAAATTGATTA
ATGGTATTAGGGATAAGCAATCTGGCAAAACAATATTAGATTTTTTGAAATCAGATGGT
TTTGCCAATCGCAATTTTATGCAGCTGATCCATGATGATAGTTTGACATTTAAAGAAGA
CATTCAAAAGCACAAGTGTCTGGACAAGGCGATAGTTTACATGAACATATTGCAAATT
TAGCTGGTAGCCCTGCTATTAAAAAAGGTATTTTACAGACTGTAAAAGTTGTTGATGAA
TTGGTCAAAGTAATGGGGCGGCATAAGCCAGAAAATATCGTTATTGAAATGGCACGTGA
AAATCAGACAACTCAAAAGGGCCAGAAAAATTCGCGAGAGCGTATGAAACGAATCGAAG
AAGGTATCAAAGAATTAGGAAGTCAGATTCTTAAAGAGCATCCTGTTGAAAATACTCAA
TTGCAAAATGAAAGCTCTATCTCTATTATCTCCAAAATGGAAGAGACATGTATGTGGA
CCAAGAATTAGATATTAATCGTTTAAGTGATTATGATGTCGATCACATTGTTCCACAAA
GTTTCCTTAAAGACGATTCAATAGACAATAAGGTCTTAACGCGTTCTGATAAAAATCGT
GGTAAATCGGATAACGTTCCAAGTGAAGAAGTAGTCAAAAGATGAAAAACTATTGGAG
ACAACTTCTAAACGCCAAGTTAATCACTCAACGTAAGTTTGATAATTTAACGAAAGCTG
AACGTGGAGGTTTGAGTGAACTTGATAAAGCTGGTTTTATCAAACGCCAATTGGTTGAA
ACTCGCCAAATCACTAAGCATGTGGCACAAATTTTGGATAGTCGCATGAATACTAAATA
CGATGAAAATGATAAACTTATTCGAGAGGTTAAAGTGATTACCTTAAAATCTAAATTAG
TTTCTGACTTCCGAAAAGATTTCCAATTCTATAAAGTACGTGAGATTAACAATTACCAT
CATGCCCATGATGCGTATCTAAATGCCGTCGTTGGAACTGCTTTGATTAAGAAATATCC
AAAACTTGAATCGGAGTTTGTCTATGGTGATTATAAGTTTATGATGTTCGTAAAATGA
TTGCTAAGTCTGAGCAAGAAATAGGCAAAGCAACCGCAAAATATTTCTTTTACTCTAAT
ATCATGAACTTCTTCAAAACAGAAATTACACTTGCAAATGGAGAGATTCGCAAACGCCC
TCTAATCGAAACTAATGGGGAAACTGGAGAAATTGTCTGGGATAAAGGGCGAGATTTTG
CCACAGTGCGCAAAGTATTGTCCATGCCCCAAGTCAATATTGTCAAGAAAACAGAAGTA
CAGACAGGCGGATTCTCCAAGGAGTCAATTTTACCAAAAAGAAATTCGGACAAGCTTAT
TGCTCGTAAAAAGACTGGGATCCAAAAAAATATGGTGGTTTTGATAGTCCAACGGTAG
CTTATTCAGTCCTAGTGGTTGCTAAGGTGGAAAAAGGGAAATCGAAGAAGTTAAAATCC
GTTAAAGAGTTACTAGGGATCACAATTATGGAAAGAAGTTCCTTTGAAAAAAATCCGAT
TGACTTTTTAGAAGCTAAAGGATATAAGGAAGTTAAAAAAGACTTAATCATTAAACTAC
CTAAATATAGTCTTTTTGAGTTAGAAAACGGTCGTAAACGGATGCTGGCTAGTGCCGGA
GAATTACAAAAAGGAAATGAGCTGGCTCTGCCAAGCAAATATGTGAATTTTTTATATTT
AGCTAGTCATTATGAAAAGTTGAAGGGTAGTCCAGAAGATAACGAACAAAAACAATTGT
```

FIG. 18 (Cont.)

TTGTGGAGCAGCATAAGCATTATTTAGATGAGATTATTGAGCAAATCAGTGAATTTTCT
AAGCGTGTTATTTTAGCAGATGCCAATTTAGATAAAGTTCTTAGTGCATATAACAAACA
TAGAGACAAACCAATACGTGAACAAGCAGAAAATATTATTCATTTATTTACGTTGACGA
ATCTTGGAGCTCCCGCTGCTTTTAAATATTTTGATACAACAATTGATCGTAAACGATAT
ACGTCTACAAAAGAAGTTTTAGATGCCACTCTTATCCATCAATCCATCACTGGTCTTTA
TGAAACACGCATTGATTTGAGTCAGCTAGGAGGTGACGGGTCACCTAAGAAAAACGAA
AAGTTGAGGATCCTAAAAAGAAACGAAAAGTTGATTAATAACATTGGAAGTGGATAA pCR1054 Sequence T7promoter-His10-MBP-TEV-D10ACas9-2NLS
(T7 Promoter to T7 Terminator)
TAATACGACTCACTATAGGGAGACCACAACGGTTTCCCTCTAGTGCCGGCTCCGGAGAG
CTCTTTAATTAAGCGGCCGCCCTGCAGGACTCGAGTTCTAGAAATAATTTTGTTTAACT
TTAAGAAGGAGATATACATATGAAATCTTCTCACCATCACCATCACCATGGTTCTTCTA
TGAAAATCGAAGAAGGTAAACTGGTAATCTGGATTAACGGCGATAAAGGCTATAACGGT
CTCGCTGAAGTCGGTAAGAAATTCGAGAAAGATACCGGAATTAAAGTCACCGTTGAGCA
TCCGGATAAACTGGAAGAGAAATTCCCACAGGTTGCGGCAACTGGCGATGGCCCTGACA
TTATCTTCTGGGCACACGACCGCTTTGGTGGCTACGCTCAATCTGGCCTGTTGGCTGAA
ATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATA
ACAAAGATCTGCTGCCGAACCCGCCAAAAACCTGGGAAGAGATCCCGGCGCTGGATAAA
GAACTGAAAGCGAAAGGTAAGAGCGCGCTGATGTTCAACCTGCAAGAACCGTACTTCAC
CTGGCCGCTGATTGCTGCTGACGGGGTTATGCGTTCAAGTATGAAAACGGCAAGTACG
ACATTAAGACGTGGGCGTGGATAACGCTGGCGCGAAAGCGGGTCTGACCTTCCTGGTT
GACCTGATTAAAAACAAACACATGAATGCAGACACCGATTACTCCATCGCAGAAGCTGC
CTTTAATAAAGGCGAAACAGCGATGACCATCAACGGCCCGTGGGCATGGTCCAACATCG
ACACCAGCAAAGTGAATTATGGTGTAACGGTACTGCCGACCTTCAAGGGTCAACCATCC
AAACCGTTCGTTGGCGTGCTGAGCGCAGGTATTAACGCCGCCAGTCCGAACAAAGAGCT
GGCAAAAGAGTTCCTCGAAAACTATCTGCTGACTGATGAAGGTCTGGAAGCGGTTAATA
AAGACAAACCGCTGGGTGCCGTAGCGCTGAAGTCTTACGAGGAAGAGTTGGCGAAAGAT
CCACGTATTGCCGCCACTATGGAAAACGCCCAGAAAGGTGAAATCATGCCGAACATCCC
GCAGATGTCCGCTTTCTGGTATGCCGTGCGTACTGCGGTGATCAACGCCGCCAGCGGTC
GTCAGACTGTCGATGAAGCCCTGAAAGACGCGCAGACTAATTCGAGCTCGAACAACAAC
AACaataACaaTAacaacaacctcGggaTcgagGAAAACCTGTAcTTCCaAtcCAatGC
CaCcATGGATAAGAAATACTCAATAGGCTTAGCTATCGGCACAAATAGCGTCGGATGGG
CGGTGATCACTGATGAATATAAGGTTCCGTCTAAAAAGTTCAAGGTTCTGGGAAATACA
GACCGCCACAGTATCAAAAAAAATCTTATAGGGGCTCTTTTATTTGACAGTGGAGAGAC
AGCGGAAGCGACTCGTCTCAAACGGACAGCTCGTAGAAGGTATACACGTCGGAAGAATC
GTATTTGTTATCTACAGGAGATTTTTTCAAATGAGATGGCGAAAGTAGATGATAGTTTC
TTTCATCGACTTGAAGAGTCTTTTTTGGTGGAAGAAGACAAGAAGCATGAACGTCATCC
TATTTTTGGAAATATAGTAGATGAAGTTGCTTATCATGAGAAATATCCAACTATCTATC
ATCTGCGAAAAAATTGGTAGATTCTACTGATAAAGCGGATTTGCGCTTAATCTATTTG
GCCTTAGCGCATATGATTAAGTTTCGTGGTCATTTTTTGATTGAGGGAGATTTAAATCC
TGATAATAGTGATGTGGACAAACTATTTATCCAGTTGGTACAAACCTACAATCAATTAT
TTGAAGAAAACCCTATTAACGCAAGTGGAGTAGATGCTAAAGCGATTCTTTCTGCACGA
TTGAGTAAATCAAGACGATTAGAAAATCTCATTGCTCAGCTCCCCGGTGAGAAGAAAA
TGGCTTATTTGGGAATCTCATTGCTTTGTCATTGGGTTTGACCCCTAATTTTAAATCAA
ATTTTGATTTGGCAGAAGATGCTAAATTACAGCTTTCAAAAGATACTTACGATGATGAT
TTAGATAATTTATTGGCGCAAATTGGAGATCAATATGCTGATTTGTTTTTGGCAGCTAA

FIG. 18 (Cont.)

```
GAATTTATCAGATGCTATTTTACTTTCAGATATCCTAAGAGTAAATACTGAAATAACTA
AGGCTCCCCTATCAGCTTCAATGATTAAACGCTACGATGAACATCATCAAGACTTGACT
CTTTTAAAAGCTTTAGTTCGACAACAACTTCCAGAAAAGTATAAAGAAATCTTTTTTGA
TCAATCAAAAAACGGATATGCAGGTTATATTGATGGGGAGCTAGCCAAGAAGAATTTT
ATAAATTTATCAAACCAATTTTAGAAAAATGGATGGTACTGAGGAATTATTGGTGAAA
CTAAATCGTGAAGATTTGCTGCGCAAGCAACGGACCTTTGACAACGGCTCTATTCCCCA
TCAAATTCACTTGGGTGAGCTGCATGCTATTTTGAGAAGACAAGAAGACTTTTATCCAT
TTTTAAAAGACAATCGTGAGAAGATTGAAAAAATCTTGACTTTTCGAATTCCTTATTAT
GTTGGTCCATTGGCGCGTGGCAATAGTCGTTTTGCATGGATGACTCGGAAGTCTGAAGA
AACAATTACCCCATGGAATTTTGAAGAAGTTGTCGATAAAGGTGCTTCAGCTCAATCAT
TTATTGAACGCATGACAAACTTTGATAAAAATCTTCCAAATGAAAAGTACTACCAAAA
CATAGTTTGCTTTATGAGTATTTTACGGTTTATAACGAATTGACAAAGGTCAAATATGT
TACTGAAGGAATGCGAAAACCAGCATTTCTTTCAGGTGAACAGAAGAAAGCCATTGTTG
ATTTACTCTTCAAAACAAATCGAAAAGTAACCGTTAAGCAATTAAAAGAAGATTATTTC
AAAAAAATAGAATGTTTTGATAGTGTTGAAATTTCAGGAGTTGAAGATAGATTTAATGC
TTCATTAGGTACCTACCATGATTTGCTAAAAATTATTAAAGATAAAGATTTTTTGGATA
ATGAAGAAATGAAGATATCTTAGAGGATATTGTTTTAACATTGACCTTATTTGAAGAT
AGGGAGATGATTGAGGAAAGACTTAAAACATATGCTCACCTCTTTGATGATAAGGTGAT
GAAACAGCTTAAACGTCGCCGTTATACTGGTTGGGGACGTTTGTCTCGAAAATTGATTA
ATGGTATTAGGGATAAGCAATCTGGCAAAACAATATTAGATTTTTTGAAATCAGATGGT
TTTGCCAATCGCAATTTTATGCAGCTGATCCATGATGATAGTTTGACATTTAAAGAAGA
CATTCAAAAAGCACAAGTGTCTGGACAAGGCGATAGTTTACATGAACATATTGCAAATT
TAGCTGGTAGCCCTGCTATTAAAAAAGGTATTTTACAGACTGTAAAAGTTGTTGATGAA
TTGGTCAAAGTAATGGGGCGGCATAAGCCAGAAAATATCGTTATTGAAATGGCACGTGA
AAATCAGACAACTCAAAAGGGCCAGAAAAATTCGCGAGAGCGTATGAAACGAATCGAAG
AAGGTATCAAAGAATTAGGAAGTCAGATTCTTAAAGAGCATCCTGTTGAAATACTCAA
TTGCAAAATGAAAAGCTCTATCTCTATTATCTCCAAAATGGAAGAGACATGTATGTGGA
CCAAGAATTAGATATTAATCGTTTAAGTGATTATGATGTCGATCACATTGTTCCACAAA
GTTTCCTTAAAGACGATTCAATAGACAATAAGGTCTTAACGCGTTCTGATAAAAATCGT
GGTAAATCGGATAACGTTCCAAGTGAAGAAGTAGTCAAAAGATGAAAAACTATTGGAG
ACAACTTCTAAACGCCAAGTTAATCACTCAACGTAAGTTTGATAATTTAACGAAAGCTG
AACGTGGAGGTTTGAGTGAACTTGATAAAGCTGGTTTTATCAAACGCCAATTGGTTGAA
ACTCGCCAAATCACTAAGCATGTGGCACAAATTTTGGATAGTCGCATGAATACTAAATA
CGATGAAATGATAAACTTATTCGAGAGGTTAAAGTGATTACCTTAAAATCTAAATTAG
TTTCTGACTTCCGAAAAGATTTCCAATTCTATAAAGTACGTGAGATTAACAATTACCAT
CATGCCCATGATGCGTATCTAAATGCCGTCGTTGGAACTGCTTTGATTAAGAAATATCC
AAAACTTGAATCGGAGTTTGTCTATGGTGATTATAAAGTTTATGATGTTCGTAAAATGA
TTGCTAAGTCTGAGCAAGAAATAGGCAAAGCAACCGCAAAATATTTCTTTTACTCTAAT
ATCATGAACTTCTTCAAAACAGAAATTACACTTGCAAATGGAGAGATTCGCAAACGCCC
TCTAATCGAAACTAATGGGGAAACTGGAGAAATTGTCTGGGATAAAGGGCGAGATTTTG
CCACAGTGCGCAAAGTATTGTCCATGCCCCAAGTCAATATTGTCAAGAAAACAGAAGTA
CAGACAGGCGGATTCTCCAAGGAGTCAATTTTACCAAAAAGAAATTCGGACAAGCTTAT
TGCTCGTAAAAAGACTGGGATCCAAAAAAATATGGTGGTTTTGATAGTCCAACGGTAG
CTTATTCAGTCCTAGTGGTTGCTAAGGTGGAAAAGGGAAATCGAAGAAGTTAAAATCC
GTTAAAGAGTTACTAGGGATCACAATTATGGAAAGAAGTTCCTTTGAAAAAAATCCGAT
TGACTTTTTAGAAGCTAAAGGATATAAGGAAGTTAAAAAAGACTTAATCATTAAACTAC
CTAAATATAGTCTTTTTGAGTTAGAAAACGGTCGTAAACGGATGCTGGCTAGTGCCGGA
GAATTACAAAAAGGAAATGAGCTGGCTCTGCCAAGCAAATATGTGAATTTTTTATATTT
```

FIG. 18 (Cont.)

AGCTAGTCATTATGAAAAGTTGAAGGGTAGTCCAGAAGATAACGAACAAAAACAATTGT
TTGTGGAGCAGCATAAGCATTATTTAGATGAGATTATTGAGCAAATCAGTGAATTTTCT
AAGCGTGTTATTTTAGCAGATGCCAATTTAGATAAAGTTCTTAGTGCATATAACAAACA
TAGAGACAAACCAATACGTGAACAAGCAGAAAATATTATTCATTTATTTACGTTGACGA
ATCTTGGAGCTCCCGCTGCTTTTAAATATTTTGATACAACAATTGATCGTAAACGATAT
ACGTCTACAAAGAAGTTTTAGATGCCACTCTTATCCATCAATCCATCACTGGTCTTTA
TGAAACACGCATTGATTTGAGTCAGCTAGGAGGTGACGGGTCACCTAAGAAAAACGAA
AAGTTGAGGATCCTAAAAAGAAACGAAAGTTGATTAATAACATTGGAAGTGGATAA pCR1055 Sequence T7promoter-His10-MBP-TEV-H840ACas9-2NLS
(T7 Promoter to T7 Terminator)
TAATACGACTCACTATAGGGAGACCACAACGGTTTCCCTCTAGTGCCGGCTCCGGAGAG
CTCTTTAATTAAGCGGCCGCCCTGCAGGACTCGAGTTCTAGAAATAATTTTGTTTAACT
TTAAGAAGGAGATATACATATGAAATCTTCTCACCATCACCATCACCATGGTTCTTCTA
TGAAAATCGAAGAAGGTAAACTGGTAATCTGGATTAACGGCGATAAAGGCTATAACGGT
CTCGCTGAAGTCGGTAAGAAATTCGAGAAAGATACCGGAATTAAAGTCACCGTTGAGCA
TCCGGATAAACTGGAAGAGAAATTCCCACAGGTTGCGGCAACTGGCGATGGCCCTGACA
TTATCTTCTGGGCACACGACCGCTTTGGTGGCTACGCTAATCTGGCCTGTTGGCTGAA
ATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATA
ACAAAGATCTGCTGCCGAACCCGCCAAAAACCTGGGAAGAGATCCCGGCGCTGGATAAA
GAACTGAAAGCGAAAGGTAAGAGCGCGCTGATGTTCAACCTGCAAGAACCGTACTTCAC
CTGGCCGCTGATTGCTGCTGACGGGGGTTATGCGTTCAAGTATGAAAACGGCAAGTACG
ACATTAAAGACGTGGGCGTGGATAACGCTGGCGCGAAAGCGGGTCTGACCTTCCTGGTT
GACCTGATTAAAAACAAACACATGAATGCAGACACCGATTACTCCATCGCAGAAGCTGC
CTTTAATAAAGGCGAAACAGCGATGACCATCAACGGCCCGTGGGCATGGTCCAACATCG
ACACCAGCAAAGTGAATTATGGTGTAACGGTACTGCCGACCTTCAAGGGTCAACCATCC
AAACCGTTCGTTGGCGTGCTGAGCGCAGGTATTAACGCCGCCAGTCCGAACAAAGAGCT
GGCAAAAGAGTTCCTCGAAAACTATCTGCTGACTGATGAAGGTCTGGAAGCGGTTAATA
AAGACAAACCGCTGGGTGCCGTAGCGCTGAAGTCTTACGAGGAAGAGTTGGCGAAAGAT
CCACGTATTGCCGCCACTATGGAAAACGCCCAGAAAGGTGAAATCATGCCGAACATCCC
GCAGATGTCCGCTTTCTGGTATGCCGTGCGTACTGCGGTGATCAACGCCGCCAGCGGTC
GTCAGACTGTCGATGAAGCCCTGAAAGACGCGCAGACTAATTCGAGCTCAACAACAAC
AACaataACaaTAacaacaacctcGggaTcgagGAAAACCTGTAcTTCCaAtcCAatGC
CaCcATGGATAAGAAATACTCAATAGGCTTAGATATCGGCACAAATAGCGTCGGATGGG
CGGTGATCACTGATGAATATAAGGTTCCGTCTAAAAAGTTCAAGGTTCTGGGAAATACA
GACCGCCACAGTATCAAAAAAATCTTATAGGGGCTCTTTTATTTGACAGTGGAGAGAC
AGCGGAAGCGACTCGTCTCAAACGGACAGCTCGTAGAAGGTATACACGTCGGAAGAATC
GTATTTGTTATCTACAGGAGATTTTTCAAATGAGATGGCGAAAGTAGATGATAGTTTC
TTTCATCGACTTGAAGAGTCTTTTTGGTGGAAGAAGACAAGAAGCATGAACGTCATCC
TATTTTTGGAAATATAGTAGATGAAGTTGCTTATCATGAGAAATATCCAACTATCTATC
ATCTGCGAAAAAATTGGTAGATTCTACTGATAAAGCGGATTTGCGCTTAATCTATTTG
GCCTTAGCGCATATGATTAAGTTTCGTGGTCATTTTTTGATTGAGGGAGATTTAAATCC
TGATAATAGTGATGTGGACAAACTATTTATCCAGTTGGTACAAACCTACAATCAATTAT
TTGAAGAAAACCCTATTAACGCAAGTGGAGTAGATGCTAAAGCGATTCTTTCTGCACGA
TTGAGTAAATCAAGACGATTAGAAAATCTCATTGCTCAGCTCCCCGGTGAGAAGAAAA
TGGCTTATTTGGGAATCTCATTGCTTTGTCATTGGGTTTGACCCCTAATTTTAAATCAA
ATTTTGATTTGGCAGAAGATGCTAAATTACAGCTTTCAAAAGATACTTACGATGATGAT

FIG. 18 (Cont.)

```
TTAGATAATTTATTGGCGCAAATTGGAGATCAATATGCTGATTTGTTTTTGGCAGCTAA
GAATTTATCAGATGCTATTTTACTTTCAGATATCCTAAGAGTAAATACTGAAATAACTA
AGGCTCCCCTATCAGCTTCAATGATTAAACGCTACGATGAACATCATCAAGACTTGACT
CTTTTAAAGCTTTAGTTCGACAACAACTTCCAGAAAAGTATAAAGAAATCTTTTTTGA
TCAATCAAAAACGGATATGCAGGTTATATTGATGGGGAGCTAGCCAAGAAGAATTTT
ATAAATTTATCAAACCAATTTTAGAAAAATGGATGGTACTGAGGAATTATTGGTGAAA
CTAAATCGTGAAGATTTGCTGCGCAAGCAACGGACCTTTGACAACGGCTCTATTCCCCA
TCAAATTCACTTGGGTGAGCTGCATGCTATTTTGAAGACAAGAAGACTTTTATCCAT
TTTTAAAAGACAATCGTGAGAAGATTGAAAAAATCTTGACTTTTCGAATTCCTTATTAT
GTTGGTCCATTGGCGCGTGGCAATAGTCGTTTTGCATGGATGACTCGGAAGTCTGAAGA
AACAATTACCCCATGGAATTTTGAAGAAGTTGTCGATAAAGGTGCTTCAGCTCAATCAT
TTATTGAACGCATGACAAACTTTGATAAAAATCTTCCAAATGAAAAGTACTACCAAAA
CATAGTTTGCTTTATGAGTATTTTACGGTTTATAACGAATTGACAAAGGTCAAATATGT
TACTGAAGGAATGCGAAAACCAGCATTTCTTTCAGGTGAACAGAAGAAAGCCATTGTTG
ATTTACTCTTCAAAACAAATCGAAAAGTAACCGTTAAGCAATTAAAAGAAGATTATTTC
AAAAAAATAGAATGTTTTGATAGTGTTGAAATTTCAGGAGTTGAAGATAGATTTAATGC
TTCATTAGGTACCTACCATGATTTGCTAAAAATTATTAAAGATAAAGATTTTTTGGATA
ATGAAGAAATGAAGATATCTTAGAGGATATTGTTTTAACATTGACCTTATTTGAAGAT
AGGGAGATGATTGAGGAAAGACTTAAAACATATGCTCACCTCTTTGATGATAAGGTGAT
GAAACAGCTTAAACGTCGCCGTTATACTGGTTGGGGACGTTTGTCTCGAAAATTGATTA
ATGGTATTAGGGATAAGCAATCTGGCAAAACAATATTAGATTTTTTGAAATCAGATGGT
TTTGCCAATCGCAATTTTATGCAGCTGATCCATGATGATAGTTTGACATTTAAAGAAGA
CATTCAAAAAGCACAAGTGTCTGGACAAGGCGATAGTTTACATGAACATATTGCAAATT
TAGCTGGTAGCCCTGCTATTAAAAAAGGTATTTTACAGACTGTAAAAGTTGTTGATGAA
TTGGTCAAAGTAATGGGGCGGCATAAGCCAGAAAATATCGTTATTGAAATGGCACGTGA
AAATCAGACAACTCAAAAGGGCCAGAAAAATTCGCGAGAGCGTATGAAACGAATCGAAG
AAGGTATCAAAGAATTAGGAAGTCAGATTCTTAAAGAGCATCCTGTTGAAAATACTCAA
TTGCAAAATGAAAAGCTCTATCTCTATTATCTCCAAAATGGAAGAGACATGTATGTGGA
CCAAGAATTAGATATTAATCGTTTAAGTGATTATGATGTCGATGCCATTGTTCCACAAA
GTTTCCTTAAAGACGATTCAATAGACAATAAGGTCTTAACGCGTTCTGATAAAAATCGT
GGTAAATCGGATAACGTTCCAAGTGAAGAAGTAGTCAAAAGATGAAAAACTATTGGAG
ACAACTTCTAAACGCCAAGTTAATCACTCAACGTAAGTTTGATAATTTAACGAAAGCTG
AACGTGGAGGTTTGAGTGAACTTGATAAAGCTGGTTTTATCAAACGCCAATTGGTTGAA
ACTCGCCAAATCACTAAGCATGTGGCACAAATTTTGGATAGTCGCATGAATACTAAATA
CGATGAAAATGATAAACTTATTCGAGAGGTTAAAGTGATTACCTTAAAATCTAAATTAG
TTTCTGACTTCCGAAAAGATTTCCAATTCTATAAAGTACGTGAGATTAACAATTACCAT
CATGCCCATGATGCGTATCTAAATGCCGTCGTTGGAACTGCTTTGATTAAGAAATATCC
AAAACTTGAATCGGAGTTTGTCTATGGTGATTATAAAGTTTATGATGTTCGTAAAATGA
TTGCTAAGTCTGAGCAAGAAATAGGCAAAGCAACCGCAAAATATTTCTTTTACTCTAAT
ATCATGAACTTCTTCAAAACAGAAATTACACTTGCAAATGGAGAGATTCGCAAACGCCC
TCTAATCGAAACTAATGGGGAAACTGGAGAAATTGTCTGGGATAAAGGGCGAGATTTTG
CCACAGTGCGCAAAGTATTGTCCATGCCCCAAGTCAATATTGTCAAGAAAACAGAAGTA
CAGACAGGCGGATTCTCCAAGGAGTCAATTTTACCAAAAAGAAATTCGGACAAGCTTAT
TGCTCGTAAAAAGACTGGGATCCAAAAAATATGGTGGTTTTGATAGTCCAACGGTAG
CTTATTCAGTCCTAGTGGTTGCTAAGGTGGAAAAAGGGAAATCGAAGAAGTTAAAATCC
GTTAAAGAGTTACTAGGGATCACAATTATGGAAAGAAGTTCCTTTGAAAAAAATCCGAT
TGACTTTTTAGAAGCTAAAGGATATAAGGAAGTTAAAAAAGACTTAATCATTAAACTAC
CTAAATATAGTCTTTTTGAGTTAGAAAACGGTCGTAAACGGATGCTGGCTAGTGCCGGA
```

FIG. 18 (Cont.)

GAATTACAAAAAGGAAATGAGCTGGCTCTGCCAAGCAAATATGTGAATTTTTTATATTT
AGCTAGTCATTATGAAAAGTTGAAGGGTAGTCCAGAAGATAACGAACAAAAACAATTGT
TTGTGGAGCAGCATAAGCATTATTTAGATGAGATTATTGAGCAAATCAGTGAATTTTCT
AAGCGTGTTATTTTAGCAGATGCCAATTTAGATAAAGTTCTTAGTGCATATAACAAACA
TAGAGACAAACCAATACGTGAACAAGCAGAAATATTATTCATTTATTTACGTTGACGA
ATCTTGGAGCTCCCGCTGCTTTTAAATATTTTGATACAACAATTGATCGTAAACGATAT
ACGTCTACAAAAGAAGTTTTAGATGCCACTCTTATCCATCAATCCATCACTGGTCTTTA
TGAAACACGCATTGATTTGAGTCAGCTAGGAGGTGACGGGTCACCTAAGAAAAACGAA
AAGTTGAGGATCCTAAAAAGAAACGAAAAGTTGATTAATAACATTGGAAGTGGATAA pCR1056 Sequence T7promoter-His10-MBP-TEV-dCas9-2NLS
(T7 Promoter to T7 Terminator)
TAATACGACTCACTATAGGGAGACCACAACGGTTTCCCTCTAGTGCCGGCTCCGGAGAG
CTCTTTAATTAAGCGGCCGCCCTGCAGGACTCGAGTTCTAGAAATAATTTTGTTTAACT
TTAAGAAGGAGATATACATATGAAATCTTCTCACCATCACCATCACCATGGTTCTTCTA
TGAAAATCGAAGAAGGTAAACTGGTAATCTGGATTAACGGCGATAAAGGCTATAACGGT
CTCGCTGAAGTCGGTAAGAAATTCGAGAAAGATACCGGAATTAAAGTCACCGTTGAGCA
TCCGGATAAACTGGAAGAGAAATTCCCACAGGTTGCGGCAACTGGCGATGGCCCTGACA
TTATCTTCTGGGCACACGACCGCTTTGGTGGCTACGCTCAATCTGGCCTGTTGGCTGAA
ATCACCCCGGACAAAGCGTTCCAGGACAAGCTGTATCCGTTTACCTGGGATGCCGTACG
TTACAACGGCAAGCTGATTGCTTACCCGATCGCTGTTGAAGCGTTATCGCTGATTTATA
ACAAAGATCTGCTGCCGAACCCGCCAAAAACCTGGGAAGAGATCCCGGCGCTGGATAAA
GAACTGAAAGCGAAAGGTAAGAGCGCGCTGATGTTCAACCTGCAAGAACCGTACTTCAC
CTGGCCGCTGATTGCTGCTGACGGGGTTATGCGTTCAAGTATGAAAACGGCAAGTACG
ACATTAAAGACGTGGGCGTGGATAACGCTGGCGCGAAAGCGGGTCTGACCTTCCTGGTT
GACCTGATTAAAAACAAACACATGAATGCAGACACCGATTACTCCATCGCAGAAGCTGC
CTTTAATAAAGGCGAAACAGCGATGACCATCAACGGCCCGTGGGCATGGTCCAACATCG
ACACCAGCAAAGTGAATTATGGTGTAACGGTACTGCCGACCTTCAAGGGTCAACCATCC
AAACCGTTCGTTGGCGTGCTGAGCGCAGGTATTAACGCCGCCAGTCCGAACAAAGAGCT
GGCAAAAGAGTTCCTCGAAAACTATCTGCTGACTGATGAAGGTCTGGAAGCGGTTAATA
AAGACAAACCGCTGGGTGCCGTAGCGCTGAAGTCTTACGAGGAAGAGTTGGCGAAAGAT
CCACGTATTGCCGCCACTATGGAAAACGCCCAGAAAGGTGAAATCATGCCGAACATCCC
GCAGATGTCCGCTTTCTGGTATGCCGTGCGTACTGCGGTGATCAACGCCGCCAGCGGTC
GTCAGACTGTCGATGAAGCCCTGAAAGACGCGCAGACTAATTCGAGCTCGAACAACAAC
AACaataaCaaTaacaacaacctcGggaTcgagGAAAACCTGTAcTTCCaAtcCAatGC
CaCcATGGATAAGAAATACTCAATAGGCTTAGCTATCGGCACAAATAGCGTCGGATGGG
CGGTGATCACTGATGAATATAAGGTTCCGTCTAAAAAGTTCAAGGTTCTGGGAAATACA
GACCGCCACAGTATCAAAAAAATCTTATAGGGGCTCTTTTATTTGACAGTGGAGAGAC
AGCGGAAGCGACTCGTCTCAAACGGACAGCTCGTAGAAGGTATACACGTCGGAAGAATC
GTATTTGTTATCTACAGGAGATTTTTTCAAATGAGATGGCGAAAGTAGATGATAGTTTC
TTTCATCGACTTGAAGAGTCTTTTTTGGTGGAAGAAGACAAGAAGCATGAACGTCATCC
TATTTTTGGAAATATAGTAGATGAAGTTGCTTATCATGAGAAATATCCAACTATCTATC
ATCTGCGAAAAAATTGGTAGATTCTACTGATAAAGCGGATTTGCGCTTAATCTATTTG
GCCTTAGCGCATATGATTAAGTTTCGTGGTCATTTTTTGATTGAGGGAGATTTAAATCC
TGATAATAGTGATGTGGACAAACTATTTATCCAGTTGGTACAAACCTACAATCAATTAT
TTGAAGAAACCCTATTAACGCAAGTGGAGTAGATGCTAAAGCGATTCTTTCTGCACGA
TTGAGTAAATCAAGACGATTAGAAAATCTCATTGCTCAGCTCCCCGGTGAGAAGAAAA
TGGCTTATTTGGGAATCTCATTGCTTTGTCATTGGGTTTGACCCCTAATTTTAAATCAA

FIG. 18 (Cont.)

```
ATTTTGATTTGGCAGAAGATGCTAAATTACAGCTTTCAAAAGATACTTACGATGATGAT
TTAGATAATTTATTGGCGCAAATTGGAGATCAATATGCTGATTTGTTTTGGCAGCTAA
GAATTTATCAGATGCTATTTTACTTTCAGATATCCTAAGAGTAAATACTGAAATAACTA
AGGCTCCCCTATCAGCTTCAATGATTAAACGCTACGATGAACATCATCAAGACTTGACT
CTTTTAAAAGCTTTAGTTCGACAACAACTTCCAGAAAAGTATAAAGAAATCTTTTTTGA
TCAATCAAAAACGGATATGCAGGTTATATTGATGGGGAGCTAGCCAAGAAGAATTTT
ATAAATTTATCAAACCAATTTTAGAAAAATGGATGGTACTGAGGAATTATTGGTGAAA
CTAAATCGTGAAGATTTGCTGCGCAAGCAACGGACCTTTGACAACGGCTCTATTCCCCA
TCAAATTCACTTGGGTGAGCTGCATGCTATTTTGAGAAGACAAGAAGACTTTTATCCAT
TTTTAAAAGACAATCGTGAGAAGATTGAAAAAATCTTGACTTTTCGAATTCCTTATTAT
GTTGGTCCATTGGCGCGTGGCAATAGTCGTTTTGCATGGATGACTCGGAAGTCTGAAGA
AACAATTACCCCATGGAATTTTGAAGAAGTTGTCGATAAAGGTGCTTCAGCTCAATCAT
TTATTGAACGCATGACAAACTTTGATAAAAATCTTCCAAATGAAAAGTACTACCAAAA
CATAGTTTGCTTTATGAGTATTTTACGGTTTATAACGAATTGACAAAGGTCAAATATGT
TACTGAAGGAATGCGAAACCAGCATTTCTTTCAGGTGAACAGAAGAAAGCCATTGTTG
ATTTACTCTTCAAAACAAATCGAAAAGTAACCGTTAAGCAATTAAAAGAAGATTATTTC
AAAAAAATAGAATGTTTTGATAGTGTTGAAATTTCAGGAGTTGAAGATAGATTTAATGC
TTCATTAGGTACCTACCATGATTTGCTAAAAATTATTAAAGATAAAGATTTTTTGGATA
ATGAAGAAATGAAGATATCTTAGAGGATATTGTTTTAACATTGACCTTATTTGAAGAT
AGGGAGATGATTGAGGAAAGACTTAAAACATATGCTCACCTCTTTGATGATAAGGTGAT
GAAACAGCTTAAACGTCGCCGTTATACTGGTTGGGGACGTTTGTCTCGAAAATTGATTA
ATGGTATTAGGGATAAGCAATCTGGCAAAACAATATTAGATTTTTTGAAATCAGATGGT
TTTGCCAATCGCAATTTTATGCAGCTGATCCATGATGATAGTTTGACATTTAAAGAAGA
CATTCAAAAAGCACAAGTGTCTGGACAAGGCGATAGTTTACATGAACATATTGCAAATT
TAGCTGGTAGCCCTGCTATTAAAAAAGGTATTTTACAGACTGTAAAAGTTGTTGATGAA
TTGGTCAAAGTAATGGGGCGGCATAAGCCAGAAAATATCGTTATTGAAATGGCACGTGA
AAATCAGACAACTCAAAAGGGCCAGAAAAATTCGCGAGAGCGTATGAAACGAATCGAAG
AAGGTATCAAAGAATTAGGAAGTCAGATTCTTAAAGAGCATCCTGTTGAAAATACTCAA
TTGCAAAATGAAAAGCTCTATCTCTATTATCTCCAAAATGGAAGAGACATGTATGTGGA
CCAAGAATTAGATATTAATCGTTTAAGTGATTATGATGTCGATGCCATTGTTCCACAAA
GTTTCCTTAAAGACGATTCAATAGACAATAAGGTCTTAACGCGTTCTGATAAAAATCGT
GGTAAATCGGATAACGTTCCAAGTGAAGAAGTAGTCAAAAGATGAAAAACTATTGGAG
ACAACTTCTAAACGCCAAGTTAATCACTCAACGTAAGTTTGATAATTTAACGAAAGCTG
AACGTGGAGGTTTGAGTGAACTTGATAAAGCTGGTTTTATCAAACGCCAATTGGTTGAA
ACTCGCCAAATCACTAAGCATGTGGCACAAATTTTGGATAGTCGCATGAATACTAAATA
CGATGAAAATGATAAACTTATTCGAGAGGTTAAAGTGATTACCTTAAAATCTAAATTAG
TTTCTGACTTCCGAAAAGATTTCCAATTCTATAAAGTACGTGAGATTAACAATTACCAT
CATGCCCATGATGCGTATCTAAATGCCGTCGTTGGAACTGCTTTGATTAAGAAATATCC
AAAACTTGAATCGGAGTTTGTCTATGGTGATTATAAAGTTTATGATGTTCGTAAAATGA
TTGCTAAGTCTGAGCAAGAAATAGGCAAAGCAACCGCAAAATATTTCTTTTACTCTAAT
ATCATGAACTTCTTCAAAACAGAAATTACACTTGCAAATGGAGAGATTCGCAAACGCCC
TCTAATCGAAACTAATGGGGAAACTGGAGAAATTGTCTGGGATAAAGGGCGAGATTTTG
CCACAGTGCGCAAAGTATTGTCCATGCCCCAAGTCAATATTGTCAAGAAACAGAAGTA
CAGACAGGCGGATTCTCCAAGGAGTCAATTTTACCAAAAAGAAATTCGGACAAGCTTAT
TGCTCGTAAAAAGACTGGGATCCAAAAAATATGGTGGTTTTGATAGTCCAACGGTAG
CTTATTCAGTCCTAGTGGTTGCTAAGGTGGAAAAAGGGAAATCGAAGAAGTTAAAATCC
GTTAAAGAGTTACTAGGGATCACAATTATGGAAAGAAGTTCCTTTGAAAAAAATCCGAT
TGACTTTTTAGAAGCTAAAGGATATAAGGAAGTTAAAAAAGACTTAATCATTAAACTAC
```

FIG. 18 (Cont.)

CTAAATATAGTCTTTTTGAGTTAGAAAACGGTCGTAAACGGATGCTGGCTAGTGCCGGA
GAATTACAAAAAGGAAATGAGCTGGCTCTGCCAAGCAAATATGTGAATTTTTTATATTT
AGCTAGTCATTATGAAAAGTTGAAGGGTAGTCCAGAAGATAACGAACAAAAACAATTGT
TTGTGGAGCAGCATAAGCATTATTTAGATGAGATTATTGAGCAAATCAGTGAATTTTCT
AAGCGTGTTATTTTAGCAGATGCCAATTTAGATAAAGTTCTTAGTGCATATAACAAACA
TAGAGACAAACCAATACGTGAACAAGCAGAAAATATTATTCATTTATTTACGTTGACGA
ATCTTGGAGCTCCCGCTGCTTTTAAATATTTTGATACAACAATTGATCGTAAACGATAT
ACGTCTACAAAAGAAGTTTTAGATGCCACTCTTATCCATCAATCCATCACTGGTCTTTA
TGAAACACGCATTGATTTGAGTCAGCTAGGAGGTGACGGGTCACCTAAGAAAAACGAA
AAGTTGAGGATCCTAAAAAGAAACGAAAAGTTGATTAATAACATTGGAAGTGGATAA

BFP Destination Clone (EF1alpha promoter to terminator)
ggctccggtgcccgtcagtgggcagagcgcacatcgcccacagtccccgagaagttggg
gggagggtcggcaattgaaccggtgcctagagaaggtggcgcggggtaaactgggaaa
gtgatgtcgtgtactggctccgccttttccgagggtgggggagaaccgtatataagt
gcagtagtcgccgtgaacgttcttttcgcaacgggtttgccgccagaacacaggtaag
tgccgtgtgtggttcccgcgggcctggcctctttacgggttatggcccttgcgtgcctt
gaattacttccacctggctgcagtacgtgattcttgatcccgagcttcgggttggaagt
gggtgggagagttcgaggccttgcgcttaaggagccccttcgcctcgtgcttgagttga
ggcctggcctgggcgctgggccgccgcgtgcgaatctggtggcaccttcgcgcctgtc
tcgctgctttcgataagtctctagccatttaaaattttgatgacctgctgcgacgctt
ttttctggcaagatagtcttgtaaatgcgggccaagatctgcacactggtatttcggt
ttttggggccgcgggcggcgacggggcccgtgcgtcccagcgcacatgttcggcgaggc
ggggcctgcgagcgcggccaccgagaatcggacggggtagtctcaagctggccggcct
gctctggtgcctggcctcgcgccgccgtgtatcgcccgccctgggcggcaaggctggc
ccggtcggcaccagttgcgtgagcggaaagatggccgcttccggccctgctgcaggga
gctcaaaatggaggacgcggcgctcgggagagcgggcgggtgagtcacccacacaaagg
aaaagggccttttccgtcctcagccgtcgcttcatgtgactccacggagtaccgggcgcc
gtccaggcacctcgattagttctcgagcttttggagtacgtcgtctttaggttgggggg
aggggttttatgcgatggagtttccccacactgagtgggtggagactgaagttaggcca
gcttggcacttgatgtaattctccttggaatttgccttttttgagtttggatcttggtt
cattctcaagcctcagacagtggttcaaagtttttttcttccatttcaggtgtcgtgag
gaatTAGCTTGGTACTAATACGACTCACTATAGGGAGACCCAAGCTGGCTAGGTAAGCT
TGGTACCGAGCTCGGATCCGGTACCgccaccATGGTGAGCAAGGGCGAGGAGCTGTTCA
CCGGGGTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTCATCTG
CACCACCGGCAAGCTGCCCGTGCCCTGGCCCACCCTCGTGACCACCCTGACCCATggcg
tgcagtgcttcagccgctaccccgaccacatgaagcagcacgacttcttcaagtccgcc
atgcccgaaggctacgtccaggagcgcaccatcttcttcaaggacgacggcaactacaa
gacccgcgccgaggtgaagttcgagggcgacaccctggtgaaccgcatcgagctgaagg
gcatcgacttcaaggaggacggcaacatcctggggcacaagctggagtacaactacaac
agccacaacgtctatatcatggccgacaagcagaagaacggcatcaaggtgaacttcaa
gatccgccacaacatcgaggacggcagcgtgcagctcgccgaccactaccagcagaaca
cccccatcggcgacggccccgtgctgctgcccgacaaccactacctgagcacccagtcc
AAGctgagcaaagaccccaacgagaagcgcgatcacatggtcctgctggagttcgtgac
cgccgccgggatcactctcggcatggacgagctgtacaagCTCGAGATATCTAGACCCA
GCTTTCTTGTACAAAGTGGTTGA

COMPOSITIONS AND METHODS FOR MODIFYING A TARGET NUCLEIC ACID

CROSS-REFERENCE

This application is a national stage application under 35 U.S.C. § 371 of PCT/US2016/064419, filed Dec. 1, 2016, which claims the benefit of U.S. Provisional Patent Application No. 62/262,189, filed Dec. 2, 2015, which application is incorporated herein by reference in its entirety.

INCORPORATION BY REFERENCE OF SEQUENCE LISTING PROVIDED AS A TEXT FILE

A Sequence Listing is provided herewith as a text file, "BERK-305_Seq_List_ST25.txt" created on Dec. 1, 2015 and having a size of 7,639 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In Type II CRISPR-Cas systems, Cas9 functions as an RNA-guided endonuclease that uses a dual-guide RNA consisting of crRNA and trans-activating crRNA (tracrRNA) for target recognition and cleavage by a mechanism involving two nuclease active sites that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, which are repaired either by non-homologous end joining (NHEJ) or homology-directed recombination (HDR).

SUMMARY

The present disclosure provides a system for editing genomic DNA, the system comprising an asymmetric donor DNA template; and methods of editing genomic DNA involving use of an asymmetric donor DNA template. The present disclosure provides a system for editing genomic DNA, the system comprising a Cas9 polypeptide with reduced enzymatic activity; and methods of editing genomic DNA involving use of a Cas9 polypeptide with reduced enzymatic activity.

The present disclosure provides a method of editing genomic DNA of a eukaryotic cell, wherein the genomic DNA comprises a target strand and a non-target strand, the method comprising introducing into the cell: (a) a Cas9 guide RNA, or one or more nucleic acids encoding said Cas9 guide RNA, wherein the Cas9 guide RNA hybridizes to a target sequence of the target strand of the genomic DNA; (b) an asymmetric double stranded or single stranded donor DNA molecule comprising a 5' homology arm and a 3' homology arm, wherein the 3' homology arm is 20 to 50 nucleotides in length (e.g., 20 nucleotides (nt) to 25 nt, 25 nt to 30 nt, 30 nt to 35 nt, 35 nt to 40 nt, 40 nt to 45 nt, or 45 nt to 50 nt in length), is shorter than the 5' homology arm, and comprises at least 10 consecutive nucleotides of said target sequence; and (c) a Cas9 protein or a nucleic acid encoding said Cas9 protein, wherein (i) the Cas9 protein forms a complex with the Cas9 guide RNA thereby guiding the Cas9 protein to said target sequence, (ii) the 3' homology arm of the donor DNA molecule hybridizes to the non-target strand of the genomic DNA, and (iii) a nucleotide sequence of the donor DNA molecule is incorporated into the genomic DNA. In some cases, the Cas9 protein comprises a functional RuvC domain and cleaves at least the non-target strand of genomic DNA. In some cases, the Cas9 protein comprises a functional HNH domain and cleaves at least the target strand of genomic DNA. In some cases, the donor DNA molecule is single stranded. In some cases, the 5' homology arm of the donor DNA molecule is 40 to 200 nucleotides in length (e.g., 40 nucleotides (nt) to 50 nt, 50 nt to 75 nt, 75 nt to 100 nt, 100 nt to 125 nt, 125 nt to 150 nt, 150 nt to 175 nt, or 175 nt to 200 nt in length). In some cases, the donor DNA molecule comprises a heterologous nucleotide sequence, between the 5' and 3' homology arms, that is incorporated into the genomic DNA. In some cases, the donor DNA molecule comprises one or more synthetic modifications selected from: a base modification, a sugar modification, and a backbone modification. In some cases, the donor DNA molecule comprises a phosphorothioate linkage.

The present disclosure provides a system for editing genomic DNA in a eukaryotic cell, the system comprising: (a) a Cas9 guide RNA, or one or more nucleic acids encoding said Cas9 guide RNA, wherein the Cas9 guide RNA comprises a guide sequence that is complementary to a target sequence of a target strand of genomic DNA of a eukaryotic cell; and (b) an asymmetric double stranded or single stranded donor DNA molecule comprising a 5' homology arm and a 3' homology arm, wherein the 3' homology arm is 20 to 50 nucleotides in length (e.g., 20 nucleotides (nt) to 25 nt, 25 nt to 30 nt, 30 nt to 35 nt, 35 nt to 40 nt, 40 nt to 45 nt, or 45 nt to 50 nt in length), is shorter than the 5' homology arm, and comprises at least 10 consecutive nucleotides of said target sequence. In some cases, the system comprises a Cas9 protein or a nucleic acid encoding said Cas9 protein. In some cases, the Cas9 protein comprises a functional RuvC domain. In some cases, the Cas9 protein comprises a functional HNH domain. In some cases, the donor DNA molecule is single stranded. In some cases, the 5' homology arm of the donor DNA molecule is 40 to 200 nucleotides in length (e.g., 40 nucleotides (nt) to 50 nt, 50 nt to 75 nt, 75 nt to 100 nt, 100 nt to 125 nt, 125 nt to 150 nt, 150 nt to 175 nt, or 175 nt to 200 nt in length). In some cases, the donor DNA molecule comprises nucleotide sequence, between the 5' and 3' homology arms, that is heterologous to said genomic DNA. In some cases, the donor DNA molecule comprises one or more synthetic modifications selected from: a base modification, a sugar modification, and a backbone modification. In some cases, the donor DNA molecule comprises a phosphorothioate linkage.

The present disclosure provides a method of editing a target genomic DNA of a eukaryotic cell, the method comprising introducing into the eukaryotic cell: (a) a dead Cas9 (dCas9) protein, or a nucleic acid encoding said dCas9 protein, wherein the dCas9 protein does not cleave the target genomic DNA; (b) a Cas9 guide RNA, or one or more nucleic acids encoding said Cas9 guide RNA, wherein the Cas9 guide RNA hybridizes to a target sequence of the target genomic DNA; and (c) a corresponding double stranded or single stranded donor DNA template molecule comprising at least 10 consecutive nucleotides of said target sequence, wherein the dCas9 protein forms a complex with the Cas9 guide RNA thereby guiding the dCas9 protein to said target sequence, and wherein a nucleotide sequence of the donor DNA molecule is incorporated into the genomic DNA. In some cases, the donor DNA template molecule is an asymmetric donor DNA molecule comprising a 5' homology arm and a 3' homology arm, wherein the 3' homology arm is 20 to 50 nucleotides in length (e.g., 20 nucleotides (nt) to 25 nt, 25 nt to 30 nt, 30 nt to 35 nt, 35 nt to 40 nt, 40 nt to 45 nt, or 45 nt to 50 nt in length), is shorter than the 5' homology arm, and comprises at least 10 consecutive nucleotides of said target sequence. In some cases, the 5' homology arm is 40 to 200 nucleotides in length (e.g., 40 nucleotides (nt) to 50 nt, 50 nt to 75 nt, 75 nt to 100 nt, 100 nt to 125 nt, 125 nt to 150 nt, 150 nt to 175 nt, or 175 nt to 200 nt in length). In some cases, the donor DNA template molecule is single stranded. In some cases, the donor DNA template molecule comprises a heterologous nucleotide sequence that is incorporated into the genomic DNA. In some cases, said introducing comprises introducing into the cell two or more Cas9 guide RNAs, or one or more nucleic acids encoding said two or more Cas9 guide RNAs, wherein the two or more Cas9 guide RNAs hybridize to target sequences that do not overlap with one another and are each separated from one another by 1-100 nucleotides (e.g., by 1 nucleotide to 10 nucleotides (nt), 10 nt to 20 nt, 20 nt to 30 nt, 30 nt to 40 nt, 40 nt to 50 nt, 50 nt to 60 nt, 60 nt to 70 nt, 70 nt to 80 nt, 80 nt to 90 nt, or 90 nt to 100 nt). In some cases, the two or more Cas9 guide RNAs hybridize to target sequences that overlap with the donor DNA template molecule. In some cases, said introducing comprises introducing into the cell three or more Cas9 guide RNAs, or one or more nucleic acids encoding said three or more Cas9 guide RNAs, wherein the three or more Cas9 guide RNAs hybridize to target sequences that do not overlap with one another and are each separated from one another by 1-100 nucleotides (e.g., by 1 nucleotide to 10 nucleotides (nt), 10 nt to 20 nt, 20 nt to 30 nt, 30 nt to 40 nt, 40 nt to 50 nt, 50 nt to 60 nt, 60 nt to 70 nt, 70 nt to 80 nt, 80 nt to 90 nt, or 90 nt to 100 nt). In some cases, the three or more Cas9 guide RNAs hybridize to target sequences that overlap with the donor DNA template molecule. In some cases, said introducing comprises introducing into the cell four or more Cas9 guide RNAs, or one or more nucleic acids encoding said four or more Cas9 guide RNAs, wherein the four or more Cas9 guide RNAs hybridize to target sequences that do not overlap with one another and are each separated from one another by 1-100 nucleotides (e.g., by 1 nucleotide to 10 nucleotides (nt), 10 nt to 20 nt, 20 nt to 30 nt, 30 nt to 40 nt, 40 nt to 50 nt, 50 nt to 60 nt, 60 nt to 70 nt, 70 nt to 80 nt, 80 nt to 90 nt, or 90 nt to 100 nt). In some cases, the four or more Cas9 guide RNAs hybridize to target sequences that overlap with the donor DNA template molecule. In some cases, the donor DNA molecule comprises one or more synthetic modifications selected from: a base modification, a sugar modification, and a backbone modification. In some cases, the donor DNA molecule comprises a phosphorothioate linkage.

The present disclosure provides a system for editing genomic DNA in a eukaryotic cell, the system comprising: (a) a dead Cas9 (dCas9) protein, or a nucleic acid encoding said dCas9 protein, wherein the dCas9 protein lacks catalytically active RuvC and HNH domains; (b) a Cas9 guide RNA, or one or more nucleic acids encoding said Cas9 guide RNA, wherein the Cas9 guide RNA comprises a guide sequence that is complementary to a target sequence of a target genomic DNA of a eukaryotic cell; and (c) a corresponding double stranded or single stranded donor DNA template molecule comprising at least 10 consecutive nucleotides of said target sequence. In some cases, the donor DNA template molecule is an asymmetric donor DNA molecule comprising a 5' homology arm and a 3' homology arm, wherein the 3' homology arm is 20 to 50 nucleotides in length (e.g., 20 nucleotides (nt) to 25 nt, 25 nt to 30 nt, 30 nt to 35 nt, 35 nt to 40 nt, 40 nt to 45 nt, or 45 nt to 50 nt in length), is shorter than the 5' homology arm, and comprises the at least 10 consecutive nucleotides of said target sequence. In some cases, the 5' homology arm of the donor DNA molecule is 40 to 200 nucleotides in length (e.g., 40 nucleotides (nt) to 50 nt, 50 nt to 75 nt, 75 nt to 100 nt, 100 nt to 125 nt, 125 nt to 150 nt, 150 nt to 175 nt, or 175 nt to 200 nt in length). In some cases, the donor DNA template molecule is single stranded. In some cases, the donor DNA template molecule comprises a nucleotide sequence that is a heterologous to said target genomic DNA. In some cases, the system comprises two or more Cas9 guide RNAs, or one or more nucleic acids encoding said two or more Cas9 guide RNAs, wherein the guide sequences of the two or more Cas9 guide RNAs are complementary to target sequences that do not overlap with one another and are each separated from one another by 1-100 nucleotides (e.g., by 1 nucleotide to 10 nucleotides (nt), 10 nt to 20 nt, 20 nt to 30 nt, 30 nt to 40 nt, 40 nt to 50 nt, 50 nt to 60 nt, 60 nt to 70 nt, 70 nt to 80 nt, 80 nt to 90 nt, or 90 nt to 100 nt). In some cases, the two or more Cas9 guide RNAs are complementary to target sequences that overlap with the donor DNA template molecule. In some cases, the system comprises three or more Cas9 guide RNAs, or one or more nucleic acids encoding said three or more Cas9 guide RNAs, wherein the guide sequences of the three or more Cas9 guide RNAs are complementary to target sequences that do not overlap with one another and are each separated from one another by 1-100 nucleotides (e.g., by 1 nucleotide to 10 nucleotides (nt), 10 nt to 20 nt, 20 nt to 30 nt, 30 nt to 40 nt, 40 nt to 50 nt, 50 nt to 60 nt, 60 nt to 70 nt, 70 nt to 80 nt, 80 nt to 90 nt, or 90 nt to 100 nt). In some cases, the three or more Cas9 guide RNAs are complementary to target sequences that overlap with the donor DNA template molecule. In some cases, the system comprises four or more Cas9 guide RNAs, or one or more nucleic acids encoding said four or more Cas9 guide RNAs, wherein the guide sequences of the four or more Cas9 guide RNAs are complementary to target sequences that do not overlap with one another and are each separated from one another by 1-100 nucleotides (e.g., by 1 nucleotide to 10 nucleotides (nt), 10 nt to 20 nt, 20 nt to 30 nt, 30 nt to 40 nt, 40 nt to 50 nt, 50 nt to 60 nt, 60 nt to 70 nt, 70 nt to 80 nt, 80 nt to 90 nt, or 90 nt to 100 nt). In some cases, the four or more Cas9 guide RNAs are complementary to target sequences that overlap with the donor DNA template molecule. In some cases, the donor DNA molecule comprises one or more synthetic modifications selected from: a base modification, a sugar modification, and a backbone modification. In some cases, the donor DNA molecule comprises a phosphorothioate linkage. In some cases, the system comprises a eukaryotic cell comprising said target genomic DNA.

BRIEF DESCRIPTION OF THE DRAWINGS

FIG. 10A-10B depicts flow cytometry data corresponding to data in FIG. 3.

(FIG. 16A) Dual guide RNA associated with a Cas9 protein and with a target nucleic acid. (FIG. 16B) Single guide RNA associated with a Cas9 protein and with a target nucleic acid. (FIG. 16C) Schematic of one possible single guide RNA. The depicted guide RNA is a single guide RNA with a targeter covalently linked to an activator via 4 linker nucleotides. The nucleotides are 5' to 3' from left to right. SEQ ID NO: 1089.

FIG. 17 presents the sequences of the sgRNA templates, DNA substrates, and donor DNAs used in the examples. Top to bottom: SEQ ID NOs: 1090-1133.

FIG. 18 presents the sequences of the expressed Cas9 clones used in the examples. Top to bottom: SEQ ID NOs: 1134-1140.

DEFINITIONS

Figure 1A:
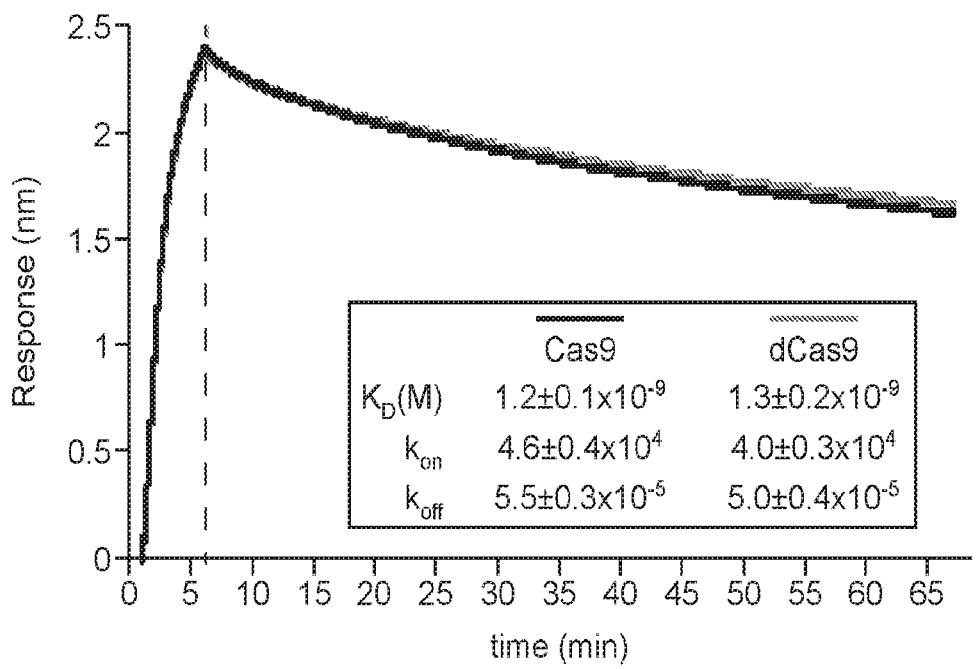
FIG. 1A-1B depicts association and dissociation of Cas9 from substrate DNA.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with an RNA guide nucleic acid, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a protein-binding segment (dsRNA duplex) of a subject guide nucleic acid molecule; of a target nucleic acid base pairing with a guide nucleic acid, etc.) is considered complementary to both a uracil (U) and to an adenine (A). For example, when a G/U base-pair can be made at a given nucleotide position of a protein-binding segment (e.g., dsRNA duplex) of a subject guide nucleic acid molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a subject Cas9/guide nucleic acid complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-1}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, microRNA (miRNA), a "non-coding" RNA (ncRNA), a guide nucleic acid, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide nucleic acid) or a coding sequence (e.g., Cas9 polypeptide, or Cas9 polypeptide) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

The term "chimeric" as used herein as applied to a nucleic acid or polypeptide refers to two components that are defined by structures derived from different sources. For example, where "chimeric" is used in the context of a chimeric polypeptide (e.g., a chimeric Cas9 protein), the chimeric polypeptide includes amino acid sequences that are derived from different polypeptides. A chimeric polypeptide may comprise either modified or naturally-occurring polypeptide sequences (e.g., a first amino acid sequence from a modified or unmodified Cas9 protein; and a second amino acid sequence other than the Cas9 protein). Similarly, "chimeric" in the context of a polynucleotide encoding a chimeric polypeptide includes nucleotide sequences derived from different coding regions (e.g., a first nucleotide sequence encoding a modified or unmodified Cas9 protein; and a second nucleotide sequence encoding a polypeptide other than a Cas9 protein).

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

"Heterologous," as used herein, means a nucleotide or polypeptide sequence that is not found in the native nucleic acid or protein, respectively. For example, in a chimeric Cas9 protein, the RNA-binding domain of a naturally-occurring bacterial Cas9 polypeptide (or a variant thereof) may be fused to a heterologous polypeptide sequence (i.e. a polypeptide sequence from a protein other than Cas9 or a polypeptide sequence from another organism). The heterologous polypeptide sequence may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 polypeptide, a variant Cas9 polypeptide may be fused to a heterologous polypeptide (i.e. a polypeptide other than Cas9), which exhibits an activity that will also be exhibited by the fusion variant Cas9 polypeptide. A heterologous nucleic acid sequence may be linked to a variant Cas9 polypeptide (e.g., by genetic engineering) to generate a nucleotide sequence encoding a fusion variant polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide nucleic acid) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., DNA such as genomic DNA) that includes a "target site" or "target sequence." The terms "target site" or "target sequence" are used interchangeably herein to refer to a nucleic acid sequence present in a target nucleic acid to which a targeting segment of a subject guide nucleic acid (e.g., Cas9 guide RNA) will bind (e.g., see FIG. 14A-14B, FIG. 15A-15B, FIG. 16A-16C), provided sufficient conditions for binding exist. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide nucleic acid is referred to as the "complementary strand"; while the strand of the target nucleic acid that is complementary to the "complementary strand" (and is therefore not complementary to the guide nucleic acid) is referred to as the "non-complementary strand" or "non-complementary strand". In cases where the target nucleic acid is a single stranded target nucleic acid (e.g., single stranded DNA (ssDNA), single stranded RNA (ssRNA)), the guide nucleic acid is complementary to and hybridizes with single stranded target nucleic acid.

By "Cas9 polypeptide" or "Cas9 protein" or "site-directed polypeptide" or "site-directed Cas9 polypeptide" it is meant a polypeptide that binds RNA (e.g., the protein binding segment of a guide nucleic acid) and is targeted to a specific sequence (a target site) in a target nucleic acid. A Cas9 polypeptide as described herein is targeted to a target site by the guide nucleic acid (e.g., Cas9 guide RNA) to which it is bound. The guide nucleic acid comprises a sequence that is complementary to a target sequence within the target nucleic acid, thus targeting the bound Cas9 polypeptide to a specific location within the target nucleic acid (the target sequence) (e.g., stabilizing the interaction of Cas9 with the target nucleic acid). In some cases, the Cas9 polypeptide is a naturally-occurring polypeptide (e.g., naturally occurs in bacterial and/or archaeal cells). In other cases, the Cas9 polypeptide is not a naturally-occurring polypeptide (e.g., the Cas9 polypeptide is a variant Cas9 polypeptide, a chimeric polypeptide as discussed below, and the like).

Exemplary Cas9 polypeptides are set forth in SEQ ID NOs: 5-816 as a non-limiting and non-exhaustive list. Naturally occurring Cas9 polypeptides bind a guide nucleic acid, are thereby directed to a specific sequence within a target nucleic acid (a target site), and cleave the target nucleic acid (e.g., cleave dsDNA to generate a double strand break, cleave ssDNA, cleave ssRNA, etc.). A subject Cas9 polypeptide comprises two portions, an RNA-binding portion and an activity portion. An RNA-binding portion interacts with a subject guide nucleic acid. An activity portion exhibits site-directed enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases, the activity portion exhibits reduced nuclease activity relative to the corresponding portion of a wild type Cas9 polypeptide. In some cases, the activity portion is enzymatically inactive.

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In certain embodiments, a complex comprising a guide nucleic acid and a Cas9 polypeptide is used for targeted cleavage of a single stranded target nucleic acid (e.g., ssRNA, ssDNA).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

A nucleic acid molecule that binds to the Cas9 polypeptide (Cas9 protein) and targets the polypeptide to a specific location within the target nucleic acid is referred to herein as a "guide nucleic acid". When the guide nucleic acid is an RNA molecule, it can be referred to as a "guide RNA" or a "gRNA" (e.g., a "Cas9 guide RNA"). A subject guide nucleic acid comprises two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule. For example, in some cases the protein-binding segment (described below) of a guide nucleic acid is one nucleic acid molecule (e.g., one RNA molecule) and the protein-binding segment therefore comprises a region of that one molecule. In other cases, the protein-binding segment (described below) of a guide nucleic acid comprises two separate molecules that are hybridized along a region of complementarity. As an illustrative, non-limiting example, a protein-binding segment of a guide nucleic acid that comprises two separate molecules can comprise (i) base pairs 40-75 of a first molecule (e.g., RNA molecule, DNA/RNA hybrid molecule) that is 100 base pairs in length; and (ii) base pairs 10-25 of a second molecule (e.g., RNA molecule) that is 50 base pairs in length. The definition of "segment," unless otherwise specifically defined in a particular context, is not limited to a specific number of total base pairs, is not limited to any particular number of base pairs from a given nucleic acid molecule, is not limited to a particular number of separate molecules within a complex, and may include regions of nucleic acid molecules that are of any total length and may or may not include regions with complementarity to other molecules.

The first segment (targeting segment) of a guide nucleic acid comprises a nucleotide sequence (a targeting sequence, also referred to as a "guide sequence") that is complementary to a specific sequence (a target site) within a target nucleic acid (e.g, a target ssRNA, a target ssDNA, the complementary strand of a double stranded target DNA, etc.). A second segment is the protein-binding segment (or "protein-binding sequence"), which interacts with (binds to) a Cas9 polypeptide. Site-specific binding and/or cleavage of the target nucleic acid can occur at locations determined by base-pairing complementarity between the guide nucleic acid and the target nucleic acid. The protein-binding segment of a subject guide nucleic acid comprises two complementary stretches of nucleotides that hybridize to one another to form a double stranded RNA duplex (dsRNA duplex).

In some embodiments, a subject nucleic acid (e.g., a guide nucleic acid, a nucleic acid comprising a nucleotide sequence encoding a guide nucleic acid (guide RNA); a nucleic acid encoding a Cas9 polypeptide; etc.) comprises a modification or sequence (e.g., an additional segment at the 5' and/or 3' end) that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a ribozyme sequence (e.g. to allow for self-cleavage and release of a mature molecule in a regulated fashion); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the nucleic acid to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA and/or RNA, including transcriptional activators, transcriptional repressors, DNA methyltransferases, DNA demethylases, histone acetyltransferases, histone deacetylases, and the like); and combinations thereof.

A subject guide nucleic acid (e.g., a Cas9 guide RNA) and a subject Cas9 polypeptide form a complex (i.e., bind via non-covalent interactions). The guide nucleic acid provides target specificity to the complex by comprising a nucleotide sequence (a "targeting sequence"/"guide sequence") that is complementary to a sequence of a target nucleic acid. The Cas9 polypeptide of the complex provides the site-specific activity (e.g., nuclease activity). In other words, the Cas9 polypeptide is guided to a target nucleic acid sequence (e.g. a target sequence in a chromosomal nucleic acid; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; etc.) by virtue of its association with the protein-binding segment of the guide nucleic acid.

In some embodiments, a subject guide nucleic acid comprises two separate nucleic acid molecules: an "activator" and a "targeter" (see below) and is referred to herein as a "dual guide nucleic acid", a "double-molecule guide nucleic acid", or a "two-molecule guide nucleic acid." If both molecules of a dual guide nucleic acid are RNA molecules, the dual guide nucleic acid can be referred to as a "dual guide RNA" or a "dgRNA." In some embodiments, the subject guide nucleic acid (Cas9 guide RNA) is a single nucleic acid molecule (single polynucleotide) and is referred to herein as a "single guide nucleic acid", a "single-molecule guide nucleic acid," or a "one-molecule guide nucleic acid." If a single guide nucleic acid is an RNA molecule, it can be referred to as a "single guide RNA" or an "sgRNA." The term "guide nucleic acid" is inclusive, referring to both dual guide nucleic acids and to single guide nucleic acids (e.g., dgRNAs, sgRNAs, etc.).

An dual guide nucleic acid comprises a crRNA-like ("CRISPR RNA" or "targeter" or "targeter RNA" or "crRNA" or "crRNA repeat") molecule and a corresponding tracrRNA-like ("trans-acting CRISPR RNA" or "activator" or "activator RNA" or "tracrRNA") molecule. In a single guide RNA, the targeter RNA and activator RNA are linked together, e.g., with intervening nucleotides.

A crRNA-like molecule (targeter RNA) comprises both the targeting segment (single stranded) of the guide nucleic acid and a stretch ("duplex-forming segment") of nucleotides that forms one half of the dsRNA duplex of the protein-binding segment of the guide nucleic acid (Cas9 guide RNA). A corresponding tracrRNA-like molecule (activator RNA) comprises a stretch of nucleotides (duplex-forming segment) that forms the other half of the dsRNA duplex of the protein-binding segment of the guide nucleic acid (guide RNA). In other words, a stretch of nucleotides of a crRNA-like molecule are complementary to and hybridize with a stretch of nucleotides of a tracrRNA-like molecule to form the dsRNA duplex of the protein-binding domain of the guide nucleic acid (Cas9 guide RNA). As such, each crRNA-like molecule can be said to have a corresponding tracrRNA-like molecule. The crRNA-like molecule additionally provides the single stranded targeting segment. Thus, a crRNA-like and a tracrRNA-like molecule (as a corresponding pair) hybridize to form a dual guide nucleic acid (or a single guide nucleic acid when the activator RNA and targeter RNA are linked together, e.g., by intervening nucleotides).

The exact sequence of a given crRNA or tracrRNA molecule is characteristic of the species in which the RNA molecules are found. A subject Cas9 dual guide RNA or Cas9 single guide RNA can include any corresponding activator and targeter pair. A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs: 827-1075, or complements thereof. For example, in some cases, sequences from SEQ ID NOs: 827-957 (which are from tracrRNAs) or complements thereof, can pair with sequences from SEQ ID NOs: 962-

1075 (which are from crRNAs), or complements thereof, to form a dsRNA duplex of a protein binding segment.

The term "activator" or "activator RNA" is used herein to mean a tracrRNA-like molecule of a dual guide nucleic acid (and of a single guide nucleic acid when the "activator RNA" and the "targeter RNA" are linked together, e.g., by intervening nucleic acids). The term "targeter" is used herein to mean a crRNA-like molecule of a dual guide nucleic acid (and of a single guide nucleic acid when the "activator" and the "targeter" are linked together by intervening nucleic acids). The term "duplex-forming segment" is used herein to mean the stretch of nucleotides of an activator or a targeter that contributes to the formation of the dsRNA duplex by hybridizing to a stretch of nucleotides of a corresponding activator or targeter molecule. In other words, an activator (activator RNA) comprises a duplex-forming segment that is complementary to the duplex-forming segment of the corresponding targeter (targeter RNA). As such, an activator comprises a duplex-forming segment while a targeter comprises both a duplex-forming segment and the targeting segment of the guide nucleic acid. A subject single guide nucleic acid can comprise an "activator" and a "targeter" where the "activator" and the "targeter" are covalently linked (e.g., by intervening nucleotides). Therefore, a subject dual guide nucleic acid can be comprised of any corresponding activator and targeter pair.

A "host cell" or "target cell" as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684;

Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

In some instances, a component (e.g., a nucleic acid component (e.g., a Cas9 guide RNA); a protein component (e.g., a Cas9 polypeptide, a variant Cas9 polypeptide); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels)(e.g., a fluorescent label) and indirectly detectable labels (indirect labels)(e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Cas9-guide RNA complex" includes a plurality of such complexes and reference to "the target nucleic acid" includes reference to one or more target nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a system for editing genomic DNA, the system comprising an asymmetric donor DNA template; and methods of editing genomic DNA involving use of an asymmetric donor DNA template. The present disclosure provides a system for editing genomic DNA, the system comprising a Cas9 polypeptide with reduced enzymatic activity; and methods of editing genomic DNA involving use of a Cas9 polypeptide with reduced enzymatic activity.

System Comprising an Asymmetric Donor DNA

The present disclosure provides a system for editing genomic DNA ("target genomic DNA"). The system comprises: a) a Cas9 guide RNA, or one or more nucleic acids comprising nucleotide sequences encoding the Cas9 guide RNA; and b) an asymmetric double-stranded or single-stranded donor DNA (also referred to as a "donor DNA template" or a "donor DNA molecule"). In some cases, the system comprises: a) a Cas9 guide RNA, or one or more nucleic acids comprising nucleotide sequences encoding the Cas9 guide RNA; b) an asymmetric double-stranded or single-stranded donor DNA (also referred to as a "donor DNA template" or a "donor DNA molecule"); and c) a Cas9 polypeptide or a nucleic acid comprising a nucleotide sequence encoding the Cas9 polypeptide. In some cases, the donor DNA is single stranded. In some cases, the donor DNA is double stranded. For simplicity, a system of the present disclosure that comprises an asymmetric donor DNA can be referred to as an "asymmetric donor DNA system."

In some cases, an asymmetric donor DNA system of the present disclosure comprises: a) a Cas9 guide RNA, or one or more nucleic acids encoding the Cas9 guide RNA, where the Cas9 guide RNA comprises a guide sequence that is complementary to a target sequence of a target strand of genomic DNA of a eukaryotic cell; and b) an asymmetric double stranded or single stranded donor DNA molecule comprising a 5' homology arm and a 3' homology arm, wherein the 3' homology arm is 20 to 50 nucleotides in length, is shorter than the 5' homology arm, and comprises at least 10 consecutive nucleotides of the target sequence.

Donor DNA

An asymmetric donor DNA suitable for inclusion in a system of the present disclosure is in some cases single stranded, and in other cases double stranded. An asymmetric donor DNA suitable for inclusion in a system of the present disclosure comprises a 5' homology arm (also referred to herein as a "long homology arm" or as "homology arm 2") and a 3' homology arm (also referred to herein as a "short homology arm" or as "homology arm 1")). See, e.g., FIG. 14A-14B.

5' Homology Arm

The 5' homology arm of an asymmetric donor DNA of the present disclosure has a length of from about 40 nucleotides (nt) to about 200 nt, e.g., from 40 nt to 45 nt, from 45 nt to 50 nt, from 50 nt to 55 nt, from 55 nt to 60 nt, from 60 nt to 65 nt, from 65 nt to 70 nt, from 70 nt to 75 nt, from 75 nt to 80 nt, from 80 nt to 85 nt, from 85 nt, to 90 nt, from 90 nt to 95 nt, from 95 nt to 100 nt, from 100 nt to 105 nt, from 105 nt to 110 nt, from 110 nt to 115 nt, from 115 nt to 120 nt, from 120 nt to 125 nt, from 125 nt to 130 nt, from 130 nt to 135 nt, from 135 nt to 140 nt, from 140 nt to 145 nt, from 145 nt to 150 nt, from 150 nt to 155 nt, from 155 nt to 160 nt, from 160 nt to 165 nt, from 165 nt to 170 nt, from 170 nt to 175 nt, from 175 nt to 180 nt, from 180 nt to 185 nt, from 185 nt to 190 nt, from 190 nt to 195 nt, or from 195 nt to 200 nt.

In some cases, the 5' homology arm of an asymmetric donor DNA of the present disclosure has a length of from 45 nt to 50 nt, e.g., the 5' homology arm of an asymmetric donor DNA of the present disclosure can have a length of 45 nt, 46 nt, 47 nt, 48 nt, 49 nt, or 50 nt.

In some cases, the 5' homology arm of an asymmetric donor DNA of the present disclosure has a length of from 50 nt to 55 nt, e.g., the 5' homology arm of an asymmetric donor DNA of the present disclosure can have a length of 50 nt, 51 nt, 52 nt, 53 nt, 54 nt, or 55 nt.

In some cases, the 5' homology arm of an asymmetric donor DNA of the present disclosure has a length of from 55 nt to 60 nt, e.g., the 5' homology arm of an asymmetric donor DNA of the present disclosure can have a length of 55 nt, 56 nt, 57 nt, 58 nt, 59 nt, or 60 nt.

In some cases, the 5' homology arm of an asymmetric donor DNA of the present disclosure has a length of from 65 nt to 70 nt, e.g., the 5' homology arm of an asymmetric donor DNA of the present disclosure can have a length of 65 nt, 66 nt, 67 nt, 68 nt, 69 nt, or 70 nt.

In some cases, the 5' homology arm of an asymmetric donor DNA of the present disclosure has a length of from 70 nt to 75 nt, e.g., the 5' homology arm of an asymmetric donor DNA of the present disclosure can have a length of 70 nt, 71 nt, 72 nt, 73 nt, 74 nt, or 75 nt.

In some cases, the 5' homology arm of an asymmetric donor DNA of the present disclosure has a length of from 75 nt to 80 nt, e.g., the 5' homology arm of an asymmetric donor DNA of the present disclosure can have a length of 75 nt, 76 nt, 77 nt, 78 nt, 79 nt, or 80 nt.

In some cases, the 5' homology arm of an asymmetric donor DNA of the present disclosure has a length of from 80 nt to 85 nt, e.g., the 5' homology arm of an asymmetric donor DNA of the present disclosure can have a length of 80 nt, 81 nt, 82 nt, 83 nt, 84 nt, or 85 nt.

In some cases, the 5' homology arm of an asymmetric donor DNA of the present disclosure has a length of from 85 nt to 90 nt, e.g., the 5' homology arm of an asymmetric donor DNA of the present disclosure can have a length of 85 nt, 86 nt, 87 nt 88 nt, 89 nt, or 90 nt.

In some cases, the 5' homology arm of an asymmetric donor DNA of the present disclosure has a length of from 90 nt to 95 nt, e.g., the 5' homology arm of an asymmetric donor DNA of the present disclosure can have a length of 90 nt, 91 nt, 92 nt, 93 nt, 94 nt, or 95 nt.

In some cases, the 5' homology arm of an asymmetric donor DNA of the present disclosure has a length of from 95 nt to 100 nt, e.g., the 5' homology arm of an asymmetric donor DNA of the present disclosure can have a length of 95 nt, 96 nt, 97 nt, 98 nt, 99 nt, or 100 nt.

In some cases, the 5' homology arm of an asymmetric donor DNA of the present disclosure has a length of from 100 nt to 105 nt, e.g., the 5' homology arm of an asymmetric donor DNA of the present disclosure can have a length of 100 nt, 101 nt, 102 nt, 103 nt, 104 nt, or 105 nt.

In some cases, the 5' homology arm of an asymmetric donor DNA of the present disclosure has a length of from 105 nt to 115 nt, e.g., the 5' homology arm of an asymmetric donor DNA of the present disclosure can have a length of 105 nt, 106 nt, 107 nt, 108 nt, 109 nt, 110 nt, 111 nt, 112 nt, 113 nt, 114 nt, or 115 nt.

In some cases, the 5' homology arm of an asymmetric donor DNA of the present disclosure has a length of from 115 nt to 125 nt, e.g., the 5' homology arm of an asymmetric donor DNA of the present disclosure can have a length of 115 nt, 116 nt, 117 nt, 118 nt, 119 nt, 120 nt, 121 nt, 122 nt, 123 nt, 124 nt, or 125 nt.

In some cases, the 5' homology arm of an asymmetric donor DNA of the present disclosure has a length of from 115 nt to 120 nt. In some cases, the 5' homology arm of an asymmetric donor DNA of the present disclosure has a length of from 120 nt to 125 nt. In some cases, the 5' homology arm of an asymmetric donor DNA of the present disclosure has a length of from 125 nt to 135 nt. In some cases, the 5' homology arm of an asymmetric donor DNA of the present disclosure has a length of from 135 nt to 140 nt. In some cases, the 5' homology arm of an asymmetric donor DNA of the present disclosure has a length of from 140 nt to 145 nt. In some cases, the 5' homology arm of an asymmetric donor DNA of the present disclosure has a length of from 145 nt to 150 nt. In some cases, the 5' homology arm of an asymmetric donor DNA of the present disclosure has a length of from 150 nt to 155 nt. In some cases, the 5' homology arm of an asymmetric donor DNA of the present disclosure has a length of from 155 nt to 160 nt. In some cases, the 5' homology arm of an asymmetric donor DNA of the present disclosure has a length of from 160 nt to 165 nt. In some cases, the 5' homology arm of an asymmetric donor DNA of the present disclosure has a length of from 165 nt to 170 nt. In some cases, the 5' homology arm of an asymmetric donor DNA of the present disclosure has a length of from 175 nt to 180 nt. In some cases, the 5' homology arm of an asymmetric donor DNA of the present disclosure has a length of from 180 nt to 185 nt. In some cases, the 5' homology arm of an asymmetric donor DNA of the present disclosure has a length of from 185 nt to 190 nt. In some cases, the 5' homology arm of an asymmetric donor DNA of the present disclosure has a length of from 190 nt to 195 nt. In some cases, the 5' homology arm of an asymmetric donor DNA of the present disclosure has a length of from 195 nt to 200 nt.

3' Homology Arm

As noted above, in some cases, an asymmetric donor DNA system of the present disclosure comprises: a) a Cas9 guide RNA, or one or more nucleic acids encoding the Cas9 guide RNA, where the Cas9 guide RNA comprises a guide sequence that is complementary to a target sequence of a target strand of genomic DNA of a eukaryotic cell; and b) an asymmetric double stranded or single stranded donor DNA molecule comprising a 5' homology arm and a 3' homology arm, wherein the 3' homology arm is 20 nucleotides to 50 nucleotides in length, is shorter than the 5' homology arm, and comprises at least 10 consecutive nucleotides of the target sequence.

The 3' homology arm of an asymmetric donor DNA of the present disclosure can have a length of from about 20 nucleotides (nt) to 50 nt, e.g., from 20 nt to 25 nt, from 25 nt to 30 nt, from 30 nt to 35 nt, from 35 nt to 40 nt, from 40 nt to 45 nt, or from 45 nt to 50 nt.

In some cases, the 3' homology arm of an asymmetric donor DNA of the present disclosure has a length of from 20 nt to 25 nt, e.g., the 3' homology arm of an asymmetric donor DNA of the present disclosure can have a length of 20 nt, 21 nt, 22 nt, 23 nt, 24 nt, or 25 nt.

In some cases, the 3' homology arm of an asymmetric donor DNA of the present disclosure has a length of from 25 nt to 30 nt, e.g., the 3' homology arm of an asymmetric donor DNA of the present disclosure can have a length of 25 nt, 26 nt, 27 nt, 28 nt, 29 nt, or 30 nt.

In some cases, the 3' homology arm of an asymmetric donor DNA of the present disclosure has a length of from 30 nt to 35 nt, e.g., the 3' homology arm of an asymmetric donor DNA of the present disclosure can have a length of 30 nt, 31 nt, 32 nt, 33 nt, 34 nt, or 35 nt.

In some cases, the 3' homology arm of an asymmetric donor DNA of the present disclosure has a length of from 35 nt to 40 nt, e.g., the 3' homology arm of an asymmetric donor DNA of the present disclosure can have a length of 35 nt, 36 nt, 37 nt, 38 nt, 39 nt, or 40 nt.

In some cases, the 3' homology arm of an asymmetric donor DNA of the present disclosure has a length of from 40 nt to 45 nt, e.g., the 3' homology arm of an asymmetric donor DNA of the present disclosure can have a length of 40 nt, 41 nt, 42 nt, 43 nt, 44 nt, or 45 nt.

In some cases, the 3' homology arm of an asymmetric donor DNA of the present disclosure has a length of from 45 nt to 50 nt, e.g., the 3' homology arm of an asymmetric donor DNA of the present disclosure can have a length of 45 nt, 46 nt, 47 nt, 48 nt, 49 nt, or 50 nt.

The '3 homology arm of an asymmetric donor DNA suitable for inclusion in a asymmetric donor DNA system of the present disclosure is shorter than the 5' homology arm. For example, in some cases, the ratio of the length of the 5' homology arm to the 3' homology arm of an asymmetric donor DNA of the present disclosure ranges from 1.5:1 to 5:1, e.g., from 1.5:1 to 2:1, from 2:1 to 2.5:1, from 2.5:1 to 3:1, from 3:1 to 3.5:1, from 3.5:1 to 4:1, from 4:1 to 4.5:1, or from 4.5:1 to 5:1. In some cases, the ratio of the length of the 5' homology arm to the 3' homology arm of an asymmetric donor DNA of the present disclosure is from 2:1 to 3:1. In some cases, the ratio of the length of the 5' homology arm to the 3' homology arm of an asymmetric donor DNA of the present disclosure is from 2.5:1 to 3:1.

In some cases, the ratio of the length of the 5' homology arm to the 3' homology arm of an asymmetric donor DNA of the present disclosure ranges from 5:1 to 10:1, e.g., from 5:1 to 6:1, from 6:1 to 7:1, from 7:1 to 8:1, from 8:1 to 9:1, or from 9:1 to 10:1.

As noted above, in some cases, an asymmetric donor DNA system of the present disclosure comprises: a) a Cas9 guide RNA, or one or more nucleic acids encoding the Cas9 guide RNA, where the Cas9 guide RNA comprises a guide sequence that is complementary to a target sequence of a target strand of genomic DNA of a eukaryotic cell; and b) an asymmetric double stranded or single stranded donor DNA molecule comprising a 5' homology arm and a 3' homology arm, wherein the 3' homology arm is 20 to 50 nucleotides in length, is shorter than the 5' homology arm, and comprises at least 10 consecutive nucleotides of the target sequence.

Figure 14A:
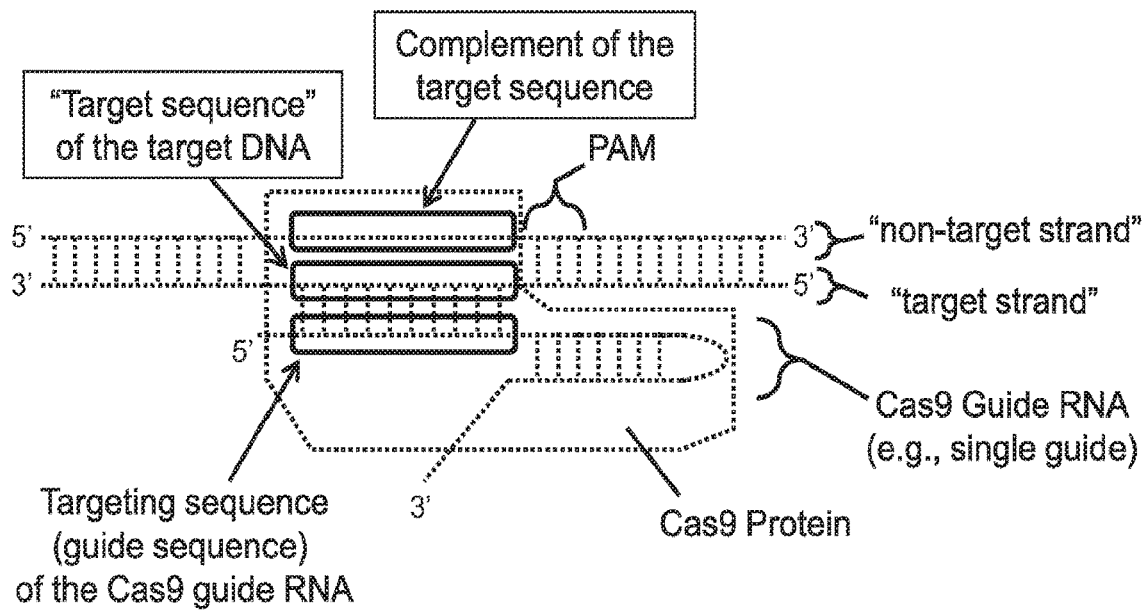
FIG. 14A-14B depict schematically a target nucleic acid, a guide RNA, and a Cas9 protein (FIG. 14A) and binding of an asymmetric donor DNA to the non-target strand of a target nucleic acid (FIG. 14B).
Figure 14B:
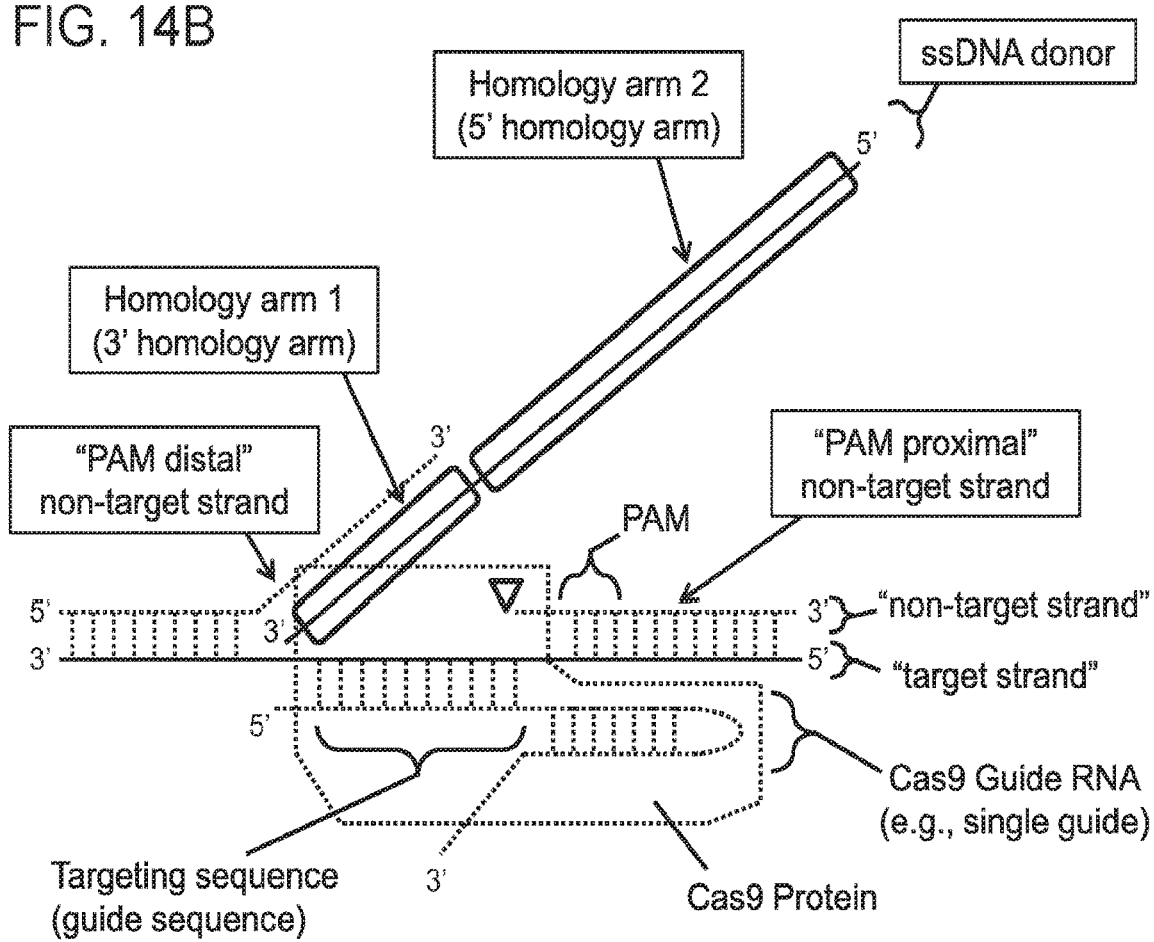
Figure 15A:
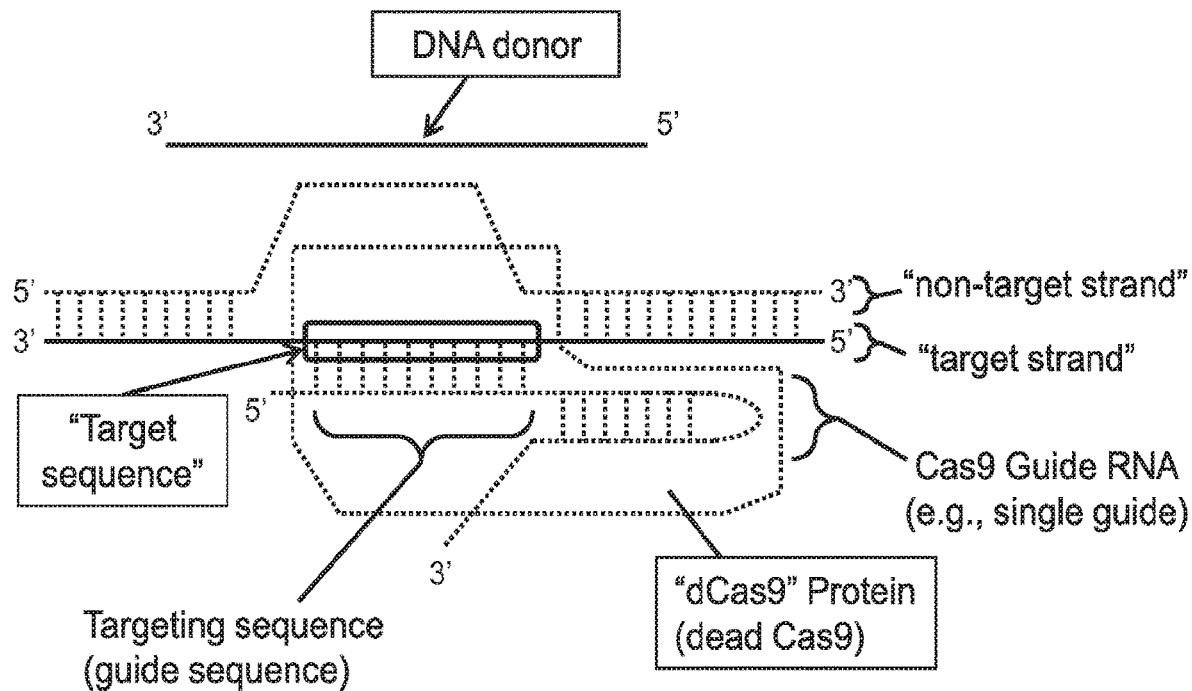
FIG. 15A-15B depict schematically the interaction of a Cas9 polypeptide with reduced enzymatic activity ("dead Cas9" or "dCas9") with a guide RNA and a target nucleic acid.
Figure 15B:
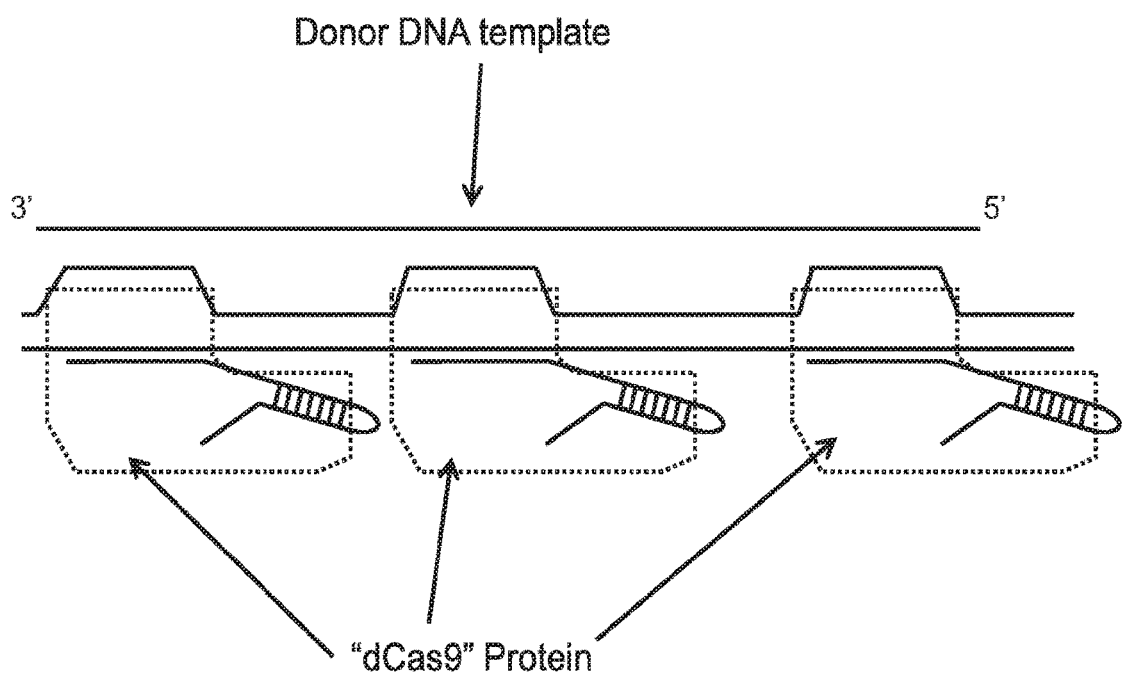

Throughout this disclosure (e.g., in the paragraphs below), as is depicted in FIG. 14B, when referring to a 3' homology arm of a subject asymmetric donor DNA (or symmetric donor DNA), the phrase "can comprise [x] consecutive nucleotides that are identical to the same number of consecutive nucleotides of the target sequence in the target strand" as used herein can be used interchangeably with the phrase "can comprise [x] consecutive nucleotides that are 100% complementary to the same number of consecutive nucleotides of the guide sequence (targeting sequence) of the Cas9 guide RNA." Thus, the description of the 3' homology arm of a subject asymmetric (or symmetric) donor DNA can be phrased to have identity with the target strand of the target DNA, or can instead be phrased to have complementarity with (or be complementary to) the guide sequence (targeting sequence) of the Cas9 guide RNA. This is because (i) both the donor DNA and the target strand of the target DNA have complementarity with (are complementary to) the non-target strand of the target DNA; and (ii) both the guide sequence (targeting sequence) of the Cas9 guide RNA and the non-target strand of the target DNA have complementarity with (are complementary to) the target strand of the target DNA.

To the contrary, in some cases, the 5' homology arm of a subject asymmetric donor DNA does not "comprise [x] consecutive nucleotides that are identical to the same number of consecutive nucleotides of the target sequence in the target strand" (e.g., does not "comprise [x] consecutive nucleotides that are 100% complementary to the same number of consecutive nucleotides of the guide sequence (targeting sequence) of the Cas9 guide RNA).

Another way throughout this disclosure to describe the above feature of the 3' homology arm of a subject asymmetric donor DNA (e.g., as is depicted in FIG. 14B) is to say that the 3' homology arm of a subject asymmetric donor DNA (after the non-target strand of the target DNA is cleaved into a PAM distal non-target DNA strand and a PAM proximal non-target DNA strand) hybridizes to (i.e., has "complementarity with", is "complementary to") the PAM distal non-target DNA strand. Thus, this phrasing can be substituted for either of the phrases (i) "can comprise [x] consecutive nucleotides that are identical to the same number of consecutive nucleotides of the target sequence in the target strand" or (ii) "can comprise [x] consecutive nucleotides that are 100% complementary to the same number of consecutive nucleotides of the guide sequence (targeting sequence) of the Cas9 guide RNA." In other words, a 3' homology arm can be described as such: "can comprise [x] consecutive nucleotides that are 100% complementary to the same number of consecutive nucleotides of the PAM distal non-target DNA strand."

To the contrary, in some cases, the 5' homology arm of a subject asymmetric donor DNA (after the non-target strand of the target DNA is cleaved into a PAM distal non-target DNA strand and a PAM proximal non-target DNA strand) does not hybridize to (i.e., does not have "complementarity with", is not "complementary to") the PAM distal non-target DNA strand (it instead has complementarity with the PAM proximal non-target strand).

The 3' homology arm of an asymmetric donor DNA suitable for inclusion in an asymmetric donor DNA system of the present disclosure can comprise from 5 consecutive nucleotides to 50 consecutive nucleotides that are identical to the same number of consecutive nucleotides of the target sequence in the target strand. For example, the 3' homology arm of an asymmetric donor DNA suitable for inclusion in an asymmetric donor DNA system of the present disclosure can comprise from 5 consecutive nucleotides to 10 consecutive nucleotides, from 10 consecutive nucleotides to 15 consecutive nucleotides, from 15 consecutive nucleotides to 20 consecutive nucleotides, from 20 consecutive nucleotides to 25 consecutive nucleotides, from 25 consecutive nucleotides to 30 consecutive nucleotides, from 30 consecutive nucleotides to 35 consecutive nucleotides, from 35 consecutive nucleotides to 40 consecutive nucleotides, from 40 consecutive nucleotides to 45 consecutive nucleotides, from 10 consecutive nucleotides to 30 consecutive nucleotides, from 15 consecutive nucleotides to 30 consecutive nucleotides, from 18 consecutive nucleotides to 30 consecutive nucleotides, from 20 consecutive nucleotides to 30 consecutive nucleotides, from 10 consecutive nucleotides to 25 consecutive nucleotides, from 15 consecutive nucleotides to 25 consecutive nucleotides, from 18 consecutive nucleotides to 25 consecutive nucleotides, from 20 consecutive nucleotides to 25 consecutive nucleotides, or from 45 consecutive nucleotides to 50 consecutive nucleotides that are identical to the same number of consecutive nucleotides of the target sequence in the target strand.

In some cases, the 3' homology arm of an asymmetric donor DNA suitable for inclusion in an asymmetric donor DNA system of the present disclosure comprises at least 5 consecutive nucleotides that are identical to 5 consecutive nucleotides of the target sequence in the target strand. In some cases, the 3' homology arm of an asymmetric donor DNA suitable for inclusion in an asymmetric donor DNA system of the present disclosure comprises at least 10 consecutive nucleotides that are identical to 10 consecutive nucleotides of the target sequence in the target strand. In some cases, the 3' homology arm of an asymmetric donor DNA suitable for inclusion in an asymmetric donor DNA system of the present disclosure comprises at least 15 consecutive nucleotides that are identical to 15 consecutive nucleotides of the target sequence in the target strand. In some cases, the 3' homology arm of an asymmetric donor DNA suitable for inclusion in an asymmetric donor DNA system of the present disclosure comprises at least 20 consecutive nucleotides that are identical to 20 consecutive nucleotides of the target sequence in the target strand. In some cases, the 3' homology arm of an asymmetric donor DNA suitable for inclusion in a asymmetric donor DNA system of the present disclosure comprises at least 25 consecutive nucleotides that are identical to 25 consecutive nucleotides of the target sequence in the target strand. In some cases, the 3' homology arm of an asymmetric donor DNA suitable for inclusion in an asymmetric donor DNA system of the present disclosure comprises at least 30 consecutive nucleotides that are identical to 30 consecutive nucleotides of the target sequence in the target strand. In some cases, the 3' homology arm of an asymmetric donor DNA suitable for inclusion in an asymmetric donor DNA system of the present disclosure comprises at least 35 consecutive nucleotides that are identical to 35 consecutive nucleotides of the target sequence in the target strand. In some cases, the 3' homology arm of an asymmetric donor DNA suitable for inclusion in an asymmetric donor DNA system of the present disclosure comprises at least 40 consecutive nucleotides that are identical to 40 consecutive nucleotides of the target sequence in the target strand. In some cases, the 3' homology arm of an asymmetric donor DNA suitable for inclusion in a asymmetric donor DNA system of the present disclosure comprises at least 45 consecutive nucleotides that are identical to 45 consecutive nucleotides of the target sequence in the target strand. In some cases, the 3' homology arm of an asymmetric donor DNA suitable for inclusion in an asymmetric donor DNA system of the present disclosure comprises 50 consecutive nucleotides that are identical to 50 consecutive nucleotides of the target sequence in the target strand.

An asymmetric donor DNA suitable for inclusion in an asymmetric donor DNA system of the present disclosure can include: a) a 5' homology arm having a length of from 85 nt to 95 nt; and b) a 3' homology arm having a length of from 20 nt to 50 nt, where the 3' homology arm comprises at least 5 consecutive nucleotides that are identical to 5 consecutive nucleotides of the target sequence of a target strand of genomic DNA. An asymmetric donor DNA suitable for inclusion in an asymmetric donor DNA system of the present disclosure can include: a) a 5' homology arm having a length of from 85 nt to 95 nt; and b) a 3' homology arm having a length of from 20 nt to 50 nt, where the 3' homology arm comprises at least 10 consecutive nucleotides that are identical to 10 consecutive nucleotides of the target sequence of a target strand of genomic DNA. An asymmetric donor DNA suitable for inclusion in an asymmetric donor DNA system of the present disclosure can include: a) a 5' homology arm having a length of from 85 nt to 95 nt; and b) a 3' homology arm having a length of from 20 nt to 50 nt, where the 3' homology arm comprises at least 20 consecutive nucleotides that are identical to 20 consecutive nucleotides of the target sequence of a target strand of genomic DNA.

An asymmetric donor DNA suitable for inclusion in an asymmetric donor DNA system of the present disclosure can include: a) a 5' homology arm having a length of from 85 nt to 95 nt; and b) a 3' homology arm having a length of from 25 nt to 40 nt, where the 3' homology arm comprises at least 5 consecutive nucleotides that are identical to 5 consecutive nucleotides of the target sequence of a target strand of genomic DNA. An asymmetric donor DNA suitable for inclusion in an asymmetric donor DNA system of the present disclosure can include: a) a 5' homology arm having a length of from 85 nt to 95 nt; and b) a 3' homology arm having a length of from 25 nt to 40 nt, where the 3' homology arm comprises at least 10 consecutive nucleotides that are identical to 10 consecutive nucleotides of the target sequence of a target strand of genomic DNA. An asymmetric donor DNA suitable for inclusion in an asymmetric donor DNA system of the present disclosure can include: a) a 5' homology arm having a length of from 85 nt to 95 nt; and b) a 3' homology arm having a length of from 25 nt to 40 nt, where the 3' homology arm comprises at least 20 consecutive nucleotides that are identical to 20 consecutive nucleotides of the target sequence of a target strand of genomic DNA.

An asymmetric donor DNA suitable for inclusion in an asymmetric donor DNA system of the present disclosure can include: a) a 5' homology arm having a length of from 90 nt to 100 nt; and b) a 3' homology arm having a length of from 25 nt to 40 nt, where the 3' homology arm comprises at least 5 consecutive nucleotides that are identical to 5 consecutive nucleotides of the target sequence of a target strand of genomic DNA. An asymmetric donor DNA suitable for inclusion in an asymmetric donor DNA system of the present disclosure can include: a) a 5' homology arm having a length of from 90 nt to 100 nt; and b) a 3' homology arm having a length of from 25 nt to 40 nt, where the 3' homology arm comprises at least 10 consecutive nucleotides that are identical to 10 consecutive nucleotides of the target sequence of a target strand of genomic DNA. An asymmetric donor DNA suitable for inclusion in an asymmetric donor DNA system of the present disclosure can include: a) a 5' homology arm having a length of from 90 nt to 100 nt; and b) a 3' homology arm having a length of from 25 nt to 40 nt, where the 3' homology arm comprises at least 20 consecutive nucleotides that are identical to 20 consecutive nucleotides of the target sequence of a target strand of genomic DNA.

In some cases, an asymmetric donor DNA of the present disclosure does not include any nucleotides between the 5' and 3' homology arms; in other words, in some cases, the 3' homology arm is contiguous with and immediately adjacent to the 5' homology arm.

In some cases, an asymmetric donor DNA of the present disclosure includes one or more nucleotides (e.g., a stretch of nucleotides) between the 5' and 3' homology arms, where the stretch of nucleotides is heterologous to the target DNA being edited. For example, in some cases, an asymmetric donor DNA of the present disclosure includes a stretch of nucleotides between the 5' and 3' homology arms, where the stretch of nucleotides is heterologous to the target DNA being edited, and where the stretch of nucleotides has a length of from 1 nucleotide (nt) to 500 nt, e.g., from 1 nt to 5 nt, from 5 nt to 10 nt, from 10 nt to 25 nt, from 25 nt to 50 nt, from 50 nt to 100 nt, from 100 nt to 250 nt, or from 250 nt to 500 nt.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the target genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

Nucleic Acid Modifications

An asymmetric donor DNA of the present disclosure (for inclusion in an asymmetric donor DNA system of the present disclosure) can include one or more modifications, e.g., a base modification, a backbone modification, etc., to provide the nucleic acid with a new or enhanced feature (e.g., improved stability, improved in vivo half life, etc.). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include nucleoside modifications, sugar modifications, modified internucleoside linkages, and backbone modifications.

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —$CH_2$—NH—O—$CH_2$—, —$CH_2$—N($CH_3$)—O—$CH_2$-(known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that is suitable for use is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($—CH_2—$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630). LNAs and preparation thereof are also described in WO 98/39352 and WO 99/14226, as well as U.S. applications 20120165514, 20100216983, 20090041809, 20060117410, 20040014959, 20020094555, and 20020086998.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2 ON(CH_3)_2$ group, also known as 2'-DMAOE, as described in examples hereinbelow, and 2'-dimethylamino-ethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2CH_2CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Guide Nucleic Acid

A guide nucleic acid suitable for inclusion in a system of the present disclosure (e.g., an asymmetric donor DNA system of the present disclosure) directs the activities of an associated polypeptide (e.g., a Cas9 polypeptide) to a specific target sequence within a target nucleic acid. A suitable guide nucleic acid comprises: a first segment (also referred to herein as a "nucleic acid targeting segment", or simply a "targeting segment"); and a second segment (also referred to herein as a "protein-binding segment").

As noted above, in some embodiments, a subject guide nucleic acid (e.g., a Cas9 guide RNA) comprises two separate nucleic acid molecules: an "activator" and a "targeter" and is referred to herein as a "dual guide nucleic acid", a "double-molecule guide nucleic acid", or a "two-molecule guide nucleic acid." If both molecules of a dual guide nucleic acid are RNA molecules, the dual guide nucleic acid can be referred to as a "dual guide RNA" or a "dgRNA." In some embodiments, the subject guide nucleic acid (Cas9 guide RNA) is a single nucleic acid molecule (single polynucleotide) and is referred to herein as a "single guide nucleic acid", a "single-molecule guide nucleic acid," or a "one-molecule guide nucleic acid." If a single guide nucleic acid is an RNA molecule, it can be referred to as a "single guide RNA" or an "sgRNA" (e.g., a Cas9 single guide RNA). The terms "guide nucleic acid" and "guide RNA" are inclusive, referring to both dual guide nucleic acids and to single guide nucleic acids (e.g., dgRNAs and sgRNAs).

A dual guide nucleic acid comprises a crRNA-like ("CRISPR RNA" or "targeter" or "targeter RNA" or "crRNA" or "crRNA repeat") molecule and a corresponding tracrRNA-like ("trans-acting CRISPR RNA" or "activator" or "activator RNA" or "tracrRNA") molecule. In a single guide RNA, the targeter RNA and activator RNA are linked together, e.g., with intervening nucleotides.

In some cases, a guide nucleic acid suitable for inclusion in a system of the present disclosure (e.g., an asymmetric donor DNA system of the present disclosure) includes a nucleic acid modification. Suitable nucleic acid modifications include nucleoside modifications, sugar modifications, modified internucleoside linkages, and backbone modifications. Examples of suitable nucleic acid modifications are as described above for the asymmetric donor DNA.

First Segment: Targeting Segment

The first segment of a guide nucleic acid comprises a nucleotide sequence that is complementary to a sequence (a target site) in a target nucleic acid. In other words, the targeting segment of a subject guide nucleic acid can interact with a target nucleic acid (e.g., hybridizes with the target strand of the double stranded genomic DNA) in a sequence-specific manner via hybridization (i.e., base pairing) (e.g., see FIGS. 14A-14B and 15A-15B). As such, the nucleotide sequence of the targeting segment may vary and can determine the location within the target nucleic acid that the guide nucleic acid and the target nucleic acid will interact. The targeting segment of a guide nucleic acid can be modified (e.g., by genetic engineering) to hybridize to any desired sequence (target site) within a target nucleic acid.

The targeting segment can have a length of from about 12 nucleotides to about 100 nucleotides. For example, the targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence (the targeting sequence) of the targeting segment that is complementary to a nucleotide sequence (target site) of the target nucleic acid can have a length of 12 nt or more. For example, the targeting sequence of the targeting segment that is complementary to a target site of the target nucleic acid can have a length of 12 nt or more, 15 nt or more, 18 nt or more, 19 nt or more, 20 nt or more, 25 nt or more, 30 nt or more, 35 nt or more or 40 nt. For example, the targeting sequence of the targeting segment that is complementary to a target sequence of the target nucleic acid can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. The nucleotide sequence (the targeting sequence) of the targeting segment that is complementary to a nucleotide sequence (target site) of the target nucleic acid can have a length of 12 nt or more.

In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

Second Segment: Protein-Binding Segment

The protein-binding segment of a guide nucleic acid (e.g., Cas9 guide RNA) interacts with a Cas9 polypeptide. A guide nucleic acid guides the bound polypeptide to a specific nucleotide sequence within target nucleic acid via the above mentioned targeting segment. The protein-binding segment of a suitable guide nucleic acid (e.g., Cas9 guide RNA) comprises two stretches of nucleotides that are complementary to one another. The complementary nucleotides of the protein-binding segment hybridize to form a double stranded RNA duplex (dsRNA) (e.g., see FIG. 16A-16C).

A subject dual guide nucleic acid (e.g., Cas9 dual guide RNA) comprises two separate nucleic acid molecules. Each of the two molecules of a subject dual guide nucleic acid comprises a stretch of nucleotides that are complementary to one another such that the complementary nucleotides of the two molecules hybridize to form the double stranded RNA duplex of the protein-binding segment (e.g., see FIG. 16A). A subject single guide nucleic acid (e.g., Cas9 single guide RNA) includes two stretches of nucleotides (corresponding to the activator RNA and the targeter RNA of a dual guide RNA) that each include a region (a duplex-forming segment) that is complementary to one another such that the complementary nucleotides of the two duplex-forming segments hybridize to form the double stranded RNA duplex of the protein-binding segment (e.g., see FIG. 16B and FIG. 16C, e.g., this region is sometimes referred to as the "stem loop").

Figure 16A:
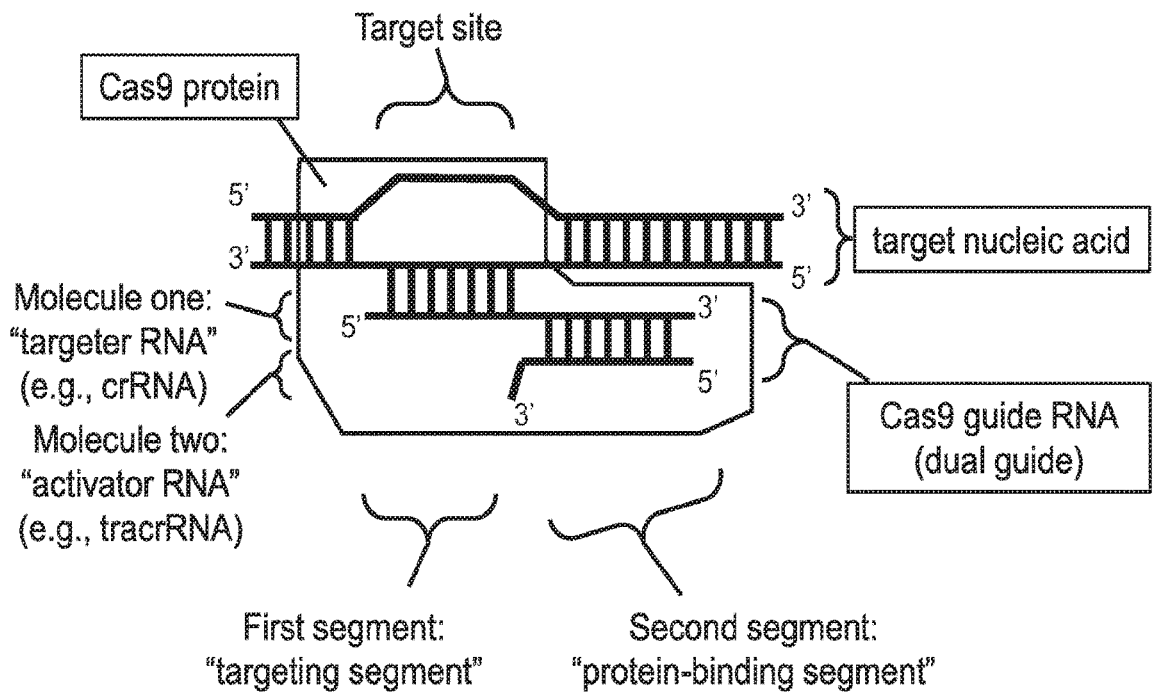
FIG. 16A-16C schematically depict two different types of Cas9 guide RNAs.
Figure 16B:
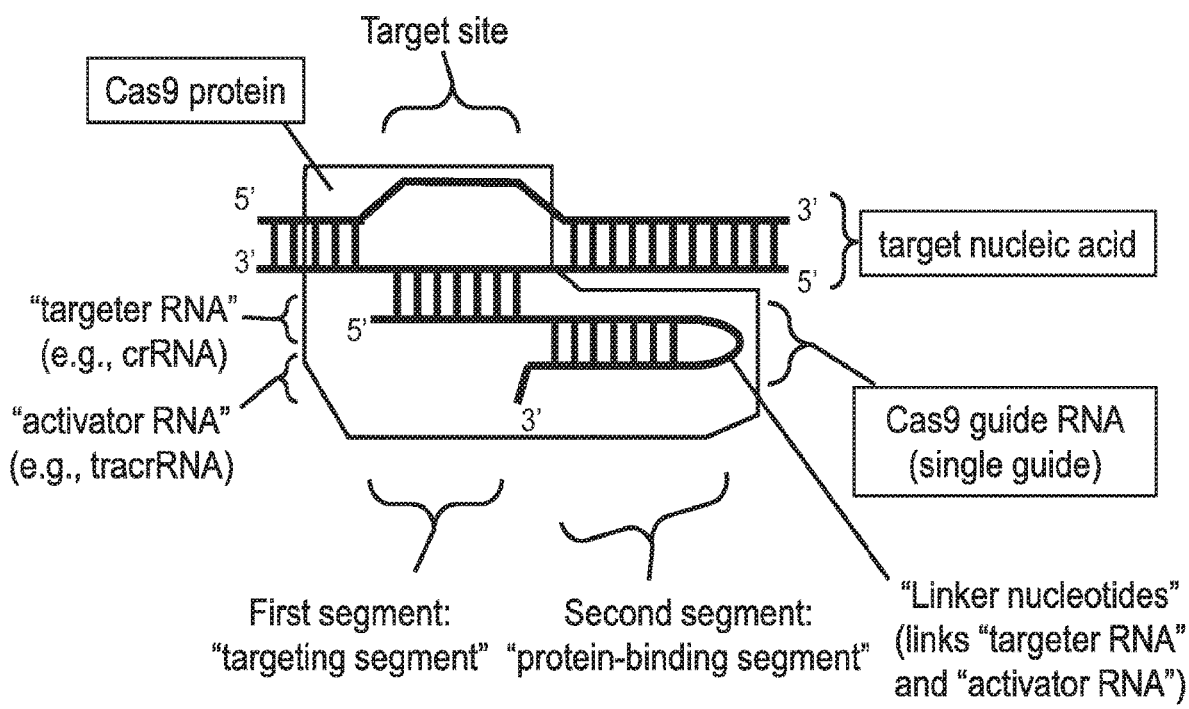
Figure 16C:
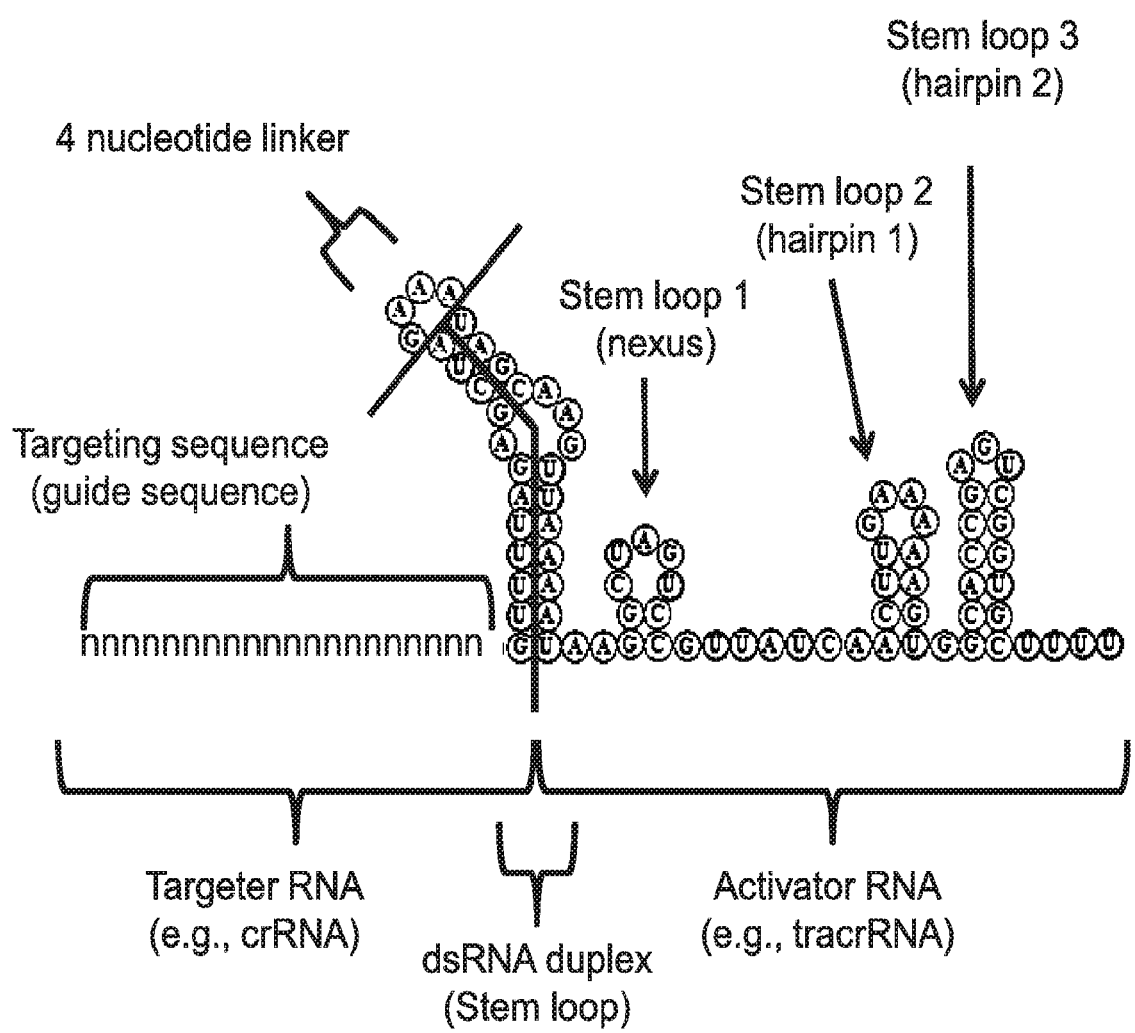

In some cases, the protein-binding segment includes stem loop 1 (the "nexus") of a Cas9 guide RNA (e.g., see FIG. 16C). For example, in some cases, the activator RNA of a Cas9 guide RNA (dgRNA or sgRNA) includes (i) a duplex forming segment that contributes to the dsRNA duplex of the protein-binding segment; and (ii) nucleotides 3' of the duplex forming segment, e.g., that form stem loop 1 (the "nexus"). For example, in some cases, the protein-binding segment includes stem loop 1 (the "nexus") of a Cas9 guide RNA. In some cases, a Cas9 guide RNA includes 5 or more nucleotides (nt) (e.g., 6 or more, 7 or more, 8 or more, 9 or more, 10 or more, 11 or more, 12 or more, 15 or more, 20 or more, 30 or more, 40 or more, 50 or more, 60 or more, 70 or more, 75 or more, or 80 or more nt) (e.g., of wild type tracr sequence) 3' of the dsRNA duplex (where 3' is relative to the duplex-forming segment of the activator sequence).

The dsRNA duplex of the guide RNA (sgRNA or dgRNA) that forms between the activator and targeter is sometimes referred to herein as the "stem loop". In addition, the activator (activator RNA, tracrRNA) of many naturally existing Cas9 guide RNAs (e.g., S. pyogenes guide RNAs) has 3 stem loops (3 hairpins) that are 3' of the duplex-forming segment of the activator. The closest stem loop to the duplex-forming segment of the activator (3' of the duplex forming segment) is called "stem loop 1" (and is also referred to herein as the "nexus"); the next stem loop is called "stem loop 2" (and is also referred to herein as the "hairpin 1"); and the next stem loop is called "stem loop 3" (and is also referred to herein as the "hairpin 2"). For example, see FIG. 16C for clarification of the nomenclature.

In some cases, an activator RNA (of a Cas9 guide RNA) has stem loop 1, but does not have stem loop 2 and does not have stem loop 3. In some cases, an activator (of a Cas9 guide RNA) has stem loop 1 and stem loop 2, but does not have stem loop 3. In some cases, an activator (of a Cas9 guide RNA) has stem loops 1, 2, and 3.

In some cases, the activator RNA (e.g., tracr sequence) of a Cas9 guide RNA (dgRNA or sgRNA) includes (i) a duplex forming segment that contributes to the dsRNA duplex of the protein-binding segment; and (ii) nucleotides 3' of the duplex forming segment (and therefore the Cas9 guide RNA includes (ii)). In some cases, the additional nucleotides 3' of the duplex forming segment form stem loop 1. In some cases, the activator (e.g., tracr sequence) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) (e.g., in some cases having wild type tracr sequence) 3' of the duplex forming segment (and therefore the Cas9 guide RNA includes (ii)). In some cases, the activator RNA of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) (e.g., in some cases having wild type tracr sequence) 3' of the duplex forming segment (and therefore the Cas9 guide RNA includes (ii)).

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) (e.g., in some cases having wild type tracr sequence) 3' of the duplex forming segment (and therefore the Cas9 guide RNA includes (ii)).

In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases the stretch is wild type tracr sequence.

Non-limiting examples of nucleotide sequences that can be included in a dual or single guide nucleic acid (e.g., dual guide RNA or single guide RNA) include either of the sequences set forth in SEQ ID NOs: 827-957, or complements thereof pairing with any sequences set forth in SEQ ID NOs: 962-1075, or complements thereof that can hybridize to form a protein binding segment.

A subject single guide nucleic acid comprises two stretches of nucleotides (much like a "targeter" and an "activator" of a dual guide nucleic acid) that are complementary to one another, hybridize to form the double stranded RNA duplex (dsRNA duplex) of the protein-binding segment (thus resulting in a stem-loop structure), and are covalently linked (e.g., by intervening nucleotides—"linkers" or "linker nucleotides"). Thus, a subject single guide nucleic acid (e.g., a single guide RNA) can comprise a targeter and an activator, each having a duplex-forming segment, where the duplex-forming segments of the targeter and the activator hybridize with one another to form a dsRNA duplex. The targeter and the activator can be covalently linked via the 3' end of the targeter and the 5' end of the activator (e.g., see FIG. 16B and FIG. 16C). Alternatively, targeter and the activator can be covalently linked via the 5' end of the targeter and the 3' end of the activator.

A linker of a single guide nucleic acid can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single guide nucleic acid is 4 nt.

An example single guide nucleic acid comprises two complementary stretches of nucleotides that hybridize to form a dsRNA duplex. In some embodiments, one of the two complementary stretches of nucleotides of the single guide nucleic acid (or the DNA encoding the stretch) is 60% or more identical to one of the activator (tracrRNA) molecules set forth in SEQ ID NOs: 827-957 (which are from tracrRNAs), or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide nucleic acid (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (or the DNA encoding the stretch) is 60% or more identical to one of the targeter (crRNA) sequences set forth in SEQ ID NOs: 962-1075 (which are from crRNAs), or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the single guide nucleic acid (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (or the DNA encoding the stretch) is 60% or more identical to one of the targeter (crRNA) sequences set forth in SEQ ID NOs: 962-1075 (which are from crRNAs), or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) and the other of the two complementary stretches of nucleotides of the single guide nucleic acid (or the DNA encoding the stretch) is 60% or more identical to one of the activator (tracrRNA) molecules set forth in SEQ ID NOs: 827-957 (which are from tracrRNAs), or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, in some cases, one of the two complementary stretches of nucleotides of the single guide nucleic acid (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) and the other of the two complementary stretches of nucleotides of the single guide nucleic acid (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

Appropriate cognate pairs of targeters and activators can be routinely determined for SEQ ID NOs: 827-957 and 962-1075 by taking into account the species name and base-pairing (for the dsRNA duplex of the protein-binding domain). Any activator/targeter pair can be used as part of subject dual guide nucleic acid or as part of a subject single guide nucleic acid.

In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 60% or more sequence identity (e.g., 65% or more, 70% or more, 75% or more, 80% or more, 85% or more, 90% or more, 95% or more, 98% or more, or 100% sequence identity) with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 70% or more sequence identity with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 75% or more sequence identity with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 80% or more sequence identity with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 85% or more sequence identity with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 90% or more sequence identity with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 95% or more sequence identity with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 98% or more sequence identity with an activator (tracrRNA) molecule set forth in any one of SEQ ID NOs: 827-957, or a complement thereof. In some cases, an activator (e.g., a trRNA, trRNA-like molecule, etc.) of a dual guide nucleic acid (e.g., a dual guide RNA) or a single guide nucleic acid (e.g., a single guide RNA) includes a stretch of nucleotides with 100% sequence identity with an activator (tracrRNA) molecule set forth in any one of SEQ ID NOs: 827-957, or a complement thereof.

In some embodiments, the duplex-forming segment of the activator (of a dual guide RNA or a single guide RNA) is 60% or more identical to one of the activator (tracrRNA) molecules set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, the duplex-forming segment of the activator (or the DNA encoding the duplex-forming segment of the activator) can be 65% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 70% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 75% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 80% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 85% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 90% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 95% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 98% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 99% or more identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) (of a dual guide RNA or a single guide RNA) can be 100% identical to one of the tracrRNA sequences set forth in SEQ ID NOs: 827-957, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, the duplex-forming segment of the targeter (or the DNA encoding the duplex-forming segment of the targeter) (of a dual guide RNA or a single guide RNA) is 60% or more identical to one of the targeter (crRNA) sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, the duplex-forming segment of the targeter (or the DNA encoding the duplex-forming segment of the targeter) (of a dual guide RNA or a single guide RNA) can be 65% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) can be 70% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 75% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 80% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 85% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 90% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 95% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 98% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 99% or more identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the targeter (or the DNA encoding the duplex-forming segment of the targeter) (of a dual guide RNA or a single guide RNA) can be 100% identical to one of the crRNA sequences set forth in SEQ ID NOs: 962-1075, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some cases, an activator (e.g., a trRNA, trRNA-like molecule, etc.) of a dual guide nucleic acid (e.g., a dual guide RNA) or a single guide nucleic acid (e.g., a single guide RNA) includes 30 or more nucleotides (nt) (e.g., 40 or more, 50 or more, 60 or more, 70 or more, 75 or more nt) (e.g., of a wild type Cas9 guide RNA). In some cases, an activator (e.g., a trRNA, trRNA-like molecule, etc.) of a dual guide nucleic acid (e.g., a dual guide RNA) or a single guide nucleic acid (e.g., a single guide RNA) has a length in a range of from 30 to 200 nucleotides (nt) (e.g., 40 to 200 nucleotides, 50 to 200 nucleotides, 60 to 200 nucleotides, 65 to 200 nucleotides, 70 to 200 nucleotides, 75 to 200 nucleotides, 40 to 150 nucleotides, 50 to 150 nucleotides, 60 to 150 nucleotides, 65 to 150 nucleotides, 70 to 150 nucleotides, 75 to 150 nucleotides, 40 to 100 nucleotides, 50 to 100 nucleotides, 60 to 100 nucleotides, 65 to 100 nucleotides, 70 to 100 nucleotides, or 75 to 100 nucleotides).

With regard to both a single guide nucleic acid and to a dual guide nucleic acid, the dsRNA duplex of the protein-binding segment can have a length from about 6 base pairs (bp) to about 50 bp. For example, the dsRNA duplex of the protein-binding segment can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the protein-binding segment can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the protein-binding segment has a length of 36 base pairs. The percent complementarity between the nucleotide sequences that hybridize to form the dsRNA duplex of the protein-binding segment can be 60% or more. For example, the percent complementarity between the nucleotide sequences that hybridize to form the dsRNA duplex of the protein-binding segment can be 65% or more, 70% or more, 75% or more, 80% or more, 85% or more, 90% or more, 95% or more, 98% or more, or 99% or more. In some cases, the percent complementarity between the nucleotide sequences that hybridize to form the dsRNA duplex of the protein-binding segment is 100%.

Stability Control Sequence (e.g., Transcriptional Terminator Segment)

In some embodiments, a guide nucleic acid comprises a stability control sequence. A stability control sequence influences the stability of a nucleic acid (e.g., a guide nucleic acid, a targeter, an activator, etc.). One example of a suitable stability control sequence for use with an RNA is a transcriptional terminator segment (i.e., a transcription termination sequence). A transcriptional terminator segment of a subject guide nucleic acid can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

In some cases, the nucleotide sequence that can be included in a stability control sequence (e.g., transcriptional termination segment, or in any segment of the guide nucleic acid to provide for increased stability) includes:

5'-UAAUCCCACAGCCGCCAGUUCCGCUGGCGGCAUUUU-5' (SEQ ID NO: 1088 (a Rho-independent trp termination site).

Additional Sequences

In some embodiments, a guide nucleic acid comprises an additional segment or segments (in some cases at the 5' end, in some cases the 3' end, in some cases at either the 5' or 3' end, in some cases embedded within the sequence (i.e., not at the 5' and/or 3' end), in some cases at both the 5' end and the 3' end, in some cases embedded and at the 5' end and/or the 3' end, etc.). For example, a suitable additional segment can comprise a 5' cap (e.g., a 7-methylguanylate cap ($m^7G$)); a 3' polyadenylated tail (i.e., a 3' poly(A) tail); a ribozyme sequence (e.g. to allow for self-cleavage of a guide nucleic acid (or component of a guide nucleic acid, e.g., a targeter, an activator, etc.)); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., a direct label (e.g., direct conjugation to a fluorescent molecule (i.e., fluorescent dye)), conjugation to a moiety that facilitates fluorescent detection, a sequence that allows for fluorescent detection; a modification or sequence that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptamers), labeled proteins, fluorescently labeled proteins, and the like); a modification or sequence that provides for increased, decreased, and/or controllable stability; and combinations thereof.

A dual guide nucleic acid can be designed to allow for controlled (i.e., conditional) binding of a targeter with an activator. Because a dual guide nucleic acid is not functional unless both the activator and the targeter are bound in a functional complex with Cas9, a dual guide nucleic acid can be inducible (e.g., drug inducible) by rendering the binding between the activator and the targeter to be inducible. As one non-limiting example, RNA aptamers can be used to regulate (i.e., control) the binding of the activator with the targeter. Accordingly, the activator and/or the targeter can include an RNA aptamer sequence.

Aptamers (e.g., RNA aptamers) are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin), which specifically binds a particular drug (e.g., a small molecule). Binding of the drug causes a structural change in the folding of the RNA, which changes a feature of the nucleic acid of which the aptamer is a part. As non-limiting examples: (i) an activator with an aptamer may not be able to bind to the cognate targeter unless the aptamer is bound by the appropriate drug; (ii) a targeter with an aptamer may not be able to bind to the cognate activator unless the aptamer is bound by the appropriate drug; and (iii) a targeter and an activator, each comprising a different aptamer that binds a different drug, may not be able to bind to each other unless both drugs are present. As illustrated by these examples, a dual guide nucleic acid can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley Interdiscip Rev RNA. 2012 May-June; 3(3):369-84; all of which are herein incorporated by reference in their entirety.

Examples of various guide RNAs (and Cas9 proteins) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Cas9 Polypeptides

As noted above, in some cases, a system of the present disclosure comprises: a) a Cas9 guide RNA, or one or more nucleic acids comprising nucleotide sequences encoding the Cas9 guide RNA; b) an asymmetric double-stranded or single-stranded donor DNA (also referred to as a "donor DNA template" or a "donor DNA molecule"); and c) a Cas9 polypeptide or a nucleic acid comprising a nucleotide sequence encoding the Cas9 polypeptide. The guide nucleic acid provides target specificity to the complex by comprising a nucleotide sequence that is complementary to a sequence (the target site) of a target nucleic acid (as noted above). The Cas9 polypeptide of the complex provides the site-specific activity. In other words, the Cas9 polypeptide is guided to a target site within a target nucleic acid sequence (e.g. a chromosomal sequence or an extrachromosomal sequence, e.g. an episomal sequence, a minicircle sequence, a mitochondrial sequence, a chloroplast sequence, etc.) by virtue of its association with the protein-binding segment of the guide nucleic acid (described above).

A suitable Cas9 polypeptide can bind and/or modify (e.g., cleave, methylate, demethylate, etc.) a target nucleic acid and/or a polypeptide associated with target nucleic acid (e.g., methylation or acetylation of a histone tail). A Cas9 polypeptide is also referred to herein as a "site-directed polypeptide."

In some cases, the Cas9 polypeptide is a naturally-occurring polypeptide (e.g., naturally occurs in bacterial and/or archaeal cells). In other cases, the Cas9 polypeptide is not a naturally-occurring polypeptide (e.g., the Cas9 polypeptide is a variant Cas9 polypeptide, a chimeric polypeptide as discussed below, and the like).

Exemplary Cas9 polypeptides are set forth in SEQ ID NOs: 5-816 as a non-limiting and non-exhaustive list of Cas9 proteins. Naturally occurring Cas9 polypeptides bind a guide nucleic acid (e.g., a Cas9 guide RNA), are thereby directed to a specific sequence within a target nucleic acid (a target site), and cleave the target nucleic acid (e.g., cleave dsDNA to generate a double strand break. A Cas9 polypeptide comprises two portions, an RNA-binding portion and an activity portion. An RNA-binding portion interacts with a guide nucleic acid. An activity portion exhibits site-directed activity (e.g., enzymatic activity such as nuclease activity). In some cases, e.g., when the Cas9 protein is a chimeric Cas9 polypeptide, the activity portion can exhibit a site-directed activity (e.g., enzymatic activity) such as DNA and/or RNA methylation activity, DNA and/or RNA cleavage activity, histone acetylation activity, histone methylation activity, etc.). In some cases, the activity portion exhibits reduced nuclease activity relative to the corresponding portion of a wild type Cas9 polypeptide (e.g., the Cas9 protein can include one or more mutations in a naturally occurring catalytic site such as in the RuvC and/or HNH domains).

Assays to determine whether a protein has an RNA-binding portion interacts with a subject guide nucleic acid can be any convenient binding assay that tests for binding between a protein and a nucleic acid. Suitable include binding assays (e.g., gel shift assays) that include adding a guide nucleic acid and a Cas9 polypeptide to a target nucleic acid. Assays to determine whether a protein has an activity portion (e.g., to determine if the polypeptide has nuclease activity that cleave a target nucleic acid) can be any convenient nucleic acid cleavage assay that tests for nucleic acid cleavage. Suitable cleavage assays that include adding a guide nucleic acid and a Cas9 polypeptide to a target nucleic acid.

Many Cas9 orthologs from a wide variety of species have been identified and the proteins share only a few identical amino acids. All identified Cas9 orthologs have the same domain architecture with a central HNH endonuclease domain and a split RuvC/RNaseH domain (e.g., see Table 1). For example, a Cas9 protein can have 3 different regions (sometimes referred to as RuvC-I, RuvC-II, and RucC-III, that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 presents motifs that can be used to help determine whether a given protein is a Cas9 protein.

TABLE 1

Table 1 lists 4 motifs that are present in Cas9 sequences from various species. The amino acids listed here are from the Cas9 from *S. pyogenes* (SEQ ID NO: 5).

| Motif # | Motif | Amino acids (residue #s) | Highly conserved |
|---|---|---|---|
| 1 | RuvC-like I | IGLDIGTNSVGWAVI (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDDSIDNKVLTRSDKN (837-863) (SEQ ID NO: 3) | H840, N854, N863 |
| 4 | RuvC-like III | HHAHDAYL (982-989) (SEQ ID NO: 4) | H982, H983, A984, D986, A987 |

In some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-816.

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable Cas9 polypeptide comprises an amino acid sequence having 4 motifs, each of motifs 1-4 having 60% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 70% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 75% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 80% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 85% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 90% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 95% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 99% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable Cas9 polypeptide comprises an amino acid sequence having 4 motifs, each of motifs 1-4 having 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. Any Cas9 protein as defined above can be used as a Cas9 polypeptide or as part of a chimeric Cas9 polypeptide of the subject methods.

In some cases, a suitable Cas9 polypeptide comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable Cas9 polypeptide comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 polypeptide comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a Cas9 polypeptide or as part of a chimeric Cas9 polypeptide of the subject methods.

In some cases, a suitable Cas9 polypeptide comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-816.

In some cases, a suitable Cas9 polypeptide comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable Cas9 polypeptide comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable Cas9 polypeptide comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable Cas9 polypeptide comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable Cas9 polypeptide comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable Cas9 polypeptide comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable Cas9 polypeptide comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable Cas9 polypeptide comprises an amino acid sequence having 99% or more amino acid sequence identity to the Cas9 amino acid sequence set forth in SEQ ID NO: 5, or to any of the amino acid sequences set forth as SEQ ID NOs: 6-816. Any Cas9 protein as defined above can be used as a Cas9 polypeptide or as part of a chimeric Cas9 polypeptide of the subject methods. In some cases, a suitable Cas9 polypeptide comprises an amino acid sequence having 100% amino acid sequence identity to the Cas9 amino acid sequence set forth in SEQ ID NO: 5, or to any of the amino acid sequences set forth as SEQ ID NOs: 6-816.

As used herein, the term "Cas9 polypeptide" encompasses the term "variant Cas9 polypeptide"; and the term "variant Cas9 polypeptide" encompasses the term "chimeric Cas9 polypeptide."

Variant Cas9 Polypeptides

In some cases, a suitable Cas9 polypeptide is a variant Cas9 polypeptide. A variant Cas9 polypeptide has an amino acid sequence that is different by one amino acid (e.g., has a deletion, insertion, substitution, fusion) (i.e., different by at least one amino acid) when compared to the amino acid sequence of a wild type Cas9 polypeptide. In some instances, the variant Cas9 polypeptide has an amino acid change (e.g., deletion, insertion, or substitution) that reduces the nuclease activity of the Cas9 polypeptide. For example, in some instances, the variant Cas9 polypeptide has less than 50%, less than 40%, less than 30%, less than 20%, less than 10%, less than 5%, or less than 1% of the nuclease activity of the corresponding wild-type Cas9 polypeptide. In some cases, the variant Cas9 polypeptide has no substantial nuclease activity. When a subject Cas9 polypeptide is a variant Cas9 polypeptide that has no substantial nuclease activity, it can be referred to as "dead Cas9" or "dCas9."

In some cases, a variant Cas9 polypeptide has reduced nuclease activity (e.g., a variant Cas9 protein can include a mutation in one or more catalytic domains). In some cases, a variant Cas9 polypeptide can cleave the complementary strand of a target nucleic acid but has reduced ability to cleave the non-complementary strand of a double stranded target nucleic acid. For example, the variant Cas9 polypeptide can have a mutation (amino acid substitution) that reduces the function of the RuvC domain (a catalytic domain). As a non-limiting example, in some embodiments, a variant Cas9 polypeptide has a mutation at position D10 (e.g., D10A; aspartate to alanine at amino acid position 10) of SEQ ID NO: 5 (or the corresponding position of any of the proteins presented in SEQ ID NOs: 6-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 polypeptide cleaves a double stranded target nucleic acid) (see, for example, Jinek et al., Science. 2012 Aug. 17; 337(6096):816-21).

In some cases, a variant Cas9 polypeptide can cleave the non-complementary strand of a double stranded target nucleic acid but has reduced ability to cleave the complementary strand of the target nucleic acid. For example, the variant Cas9 polypeptide can have a mutation (amino acid substitution) that reduces the function of the HNH domain (a catalytic domain). As a non-limiting example, in some embodiments, a variant Cas9 polypeptide has a mutation at position H840 (e.g., H840A; histidine to alanine at amino acid position 840) of SEQ ID NO: 5 (or the corresponding position of any of the proteins presented in SEQ ID NOs: 6-816) and can therefore cleave the non-complementary strand of the target nucleic acid but has reduced ability to cleave the complementary strand of the target nucleic acid (thus resulting in a SSB instead of a DSB when the variant Cas9 polypeptide cleaves a double stranded target nucleic acid). Such a Cas9 polypeptide has a reduced ability to cleave a target nucleic acid (e.g., a single stranded target nucleic acid) but retains the ability to bind a target nucleic acid (e.g., a single stranded target nucleic acid).

In some cases, a variant Cas9 polypeptide has a reduced ability to cleave both the complementary and the non-complementary strands of a double stranded target nucleic acid. As a non-limiting example, in some cases, the variant Cas9 polypeptide harbors mutations in both the RuvC and HNH domains (e.g., mutations at both the D10 and H840 positions, e.g., both the D10A and the H840A mutations, or the corresponding mutations of any of the proteins set forth as SEQ ID NOs: 5-816) such that the polypeptide has a reduced ability to cleave both the complementary and the non-complementary strands of a double stranded target nucleic acid. Such a Cas9 polypeptide can have a reduced ability to cleave a target nucleic acid but retain the ability to bind a target nucleic acid.

Other residues can be mutated to achieve the above effects (i.e. inactivate one or the other nuclease domains). As non-limiting examples, residues D10, G12, G17, E762, H840, N854, N863, H982, H983, A984, D986, and/or A987 of the Cas9 protein set forth in SEQ ID NO: 5 (or the corresponding residues of any of the proteins set forth as SEQ ID NOs: 6-816) can be altered (i.e., substituted) (e.g., see Table 1 for more information regarding the conservation of Cas9 amino acid residues, e.g., those that are highly conserved and are included in the motifs listed in Table 1). Also, mutations other than alanine substitutions are suitable.

In some embodiments, a variant Cas9 polypeptide that has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the variant Cas9 polypeptide can still bind to target nucleic acid in a site-specific manner (because it is still guided to a target nucleic acid sequence by a guide nucleic acid) as long as it retains the ability to interact with the guide nucleic acid.

In addition to the above, a variant Cas9 protein can have the same parameters for sequence identity as described above for Cas9 polypeptides. Thus, in some cases, a suitable variant Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of a Cas9 protein, e.g., as set forth in SEQ ID NOs: 1-4, respectively, as depicted in Table 1, or to the corresponding portions in any of the amino acid sequences set forth in SEQ ID NOs: 5-816.

For example, in some cases, a suitable variant Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable variant Cas9 polypeptide comprises an amino acid sequence having 4 motifs, each of motifs 1-4 having 60% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 70% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 75% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 80% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 85% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 90% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 95% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 99% or more amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. In some cases, a suitable variant Cas9 polypeptide comprises an amino acid sequence having 4 motifs, each of motifs 1-4 having 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 polypeptide comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a variant Cas9 polypeptide or as part of a chimeric variant Cas9 polypeptide of the subject methods. In some cases, a suitable variant Cas9 polypeptide comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 polypeptide comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 polypeptide comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 polypeptide comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 polypeptide comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 polypeptide comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 polypeptide comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 polypeptide comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a variant Cas9 polypeptide or as part of a chimeric variant Cas9 polypeptide of the subject methods.

In some cases, a suitable variant Cas9 polypeptide comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-816.

In some cases, a suitable variant Cas9 polypeptide comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable variant Cas9 polypeptide comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable variant Cas9 polypeptide comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable variant Cas9 polypeptide comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable variant Cas9 polypeptide comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable variant Cas9 polypeptide comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable variant Cas9 polypeptide comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable variant Cas9 polypeptide comprises an amino acid sequence having 99% or more amino acid sequence identity to the Cas9 amino acid sequence set forth in SEQ ID NO: 5, or to any of the amino acid sequences set forth as SEQ ID NOs: 6-816. Any Cas9 protein as defined above can be used as a variant Cas9 polypeptide or as part of a chimeric variant Cas9 polypeptide of the subject methods. In some cases, a suitable variant Cas9 polypeptide (e.g., a chimeric Cas9 protein, i.e., a Cas9 fusion protein) comprises an amino acid sequence having 100% amino acid sequence identity to the Cas9 amino acid sequence set forth in SEQ ID NO: 5, or to any of the amino acid sequences set forth as SEQ ID NOs: 6-816.

Chimeric Polypeptides (Fusion Polypeptides)

In some embodiments, a variant Cas9 polypeptide is a chimeric Cas9 polypeptide (also referred to herein as a fusion polypeptide, e.g., a "Cas9 fusion polypeptide"). A Cas9 fusion polypeptide can bind and/or modify a target nucleic acid (e.g., cleave, methylate, demethylate, etc.) and/or a polypeptide associated with target nucleic acid (e.g., methylation, acetylation, etc., of, for example, a histone tail).

A Cas9 fusion polypeptide is a variant Cas9 polypeptide by virtue of differing in sequence from a wild type Cas9 polypeptide. A Cas9 fusion polypeptide is a Cas9 polypeptide (e.g., a wild type Cas9 polypeptide, a variant Cas9 polypeptide, a variant Cas9 polypeptide with reduced nuclease activity (as described above), and the like) fused to a covalently linked heterologous polypeptide (also referred to as a "fusion partner"). In some cases, a Cas9 fusion polypeptide is a variant Cas9 polypeptide with reduced nuclease activity (e.g., a nickase Cas9 protein (i.e., a Cas9 protein without catalytic function of one of the RuvC or HNH domains), a dCas9, etc.) fused to a covalently linked heterologous polypeptide. In some cases, the heterologous polypeptide exhibits (and therefore provides for) an activity (e.g., an enzymatic activity) that will also be exhibited by the Cas9 fusion polypeptide (e.g., methyltransferase activity, acetyltransferase activity, kinase activity, ubiquitinating activity, etc.). In some such cases, a method of binding, e.g., where the Cas9 polypeptide is a variant Cas9 polypeptide having a fusion partner (i.e., having a heterologous polypeptide) with an activity (e.g., an enzymatic activity) that modifies the target nucleic acid, the method can also be considered to be a method of modifying the target nucleic acid. In some cases, a method of binding a target nucleic acid (e.g., a single stranded target nucleic acid) can result in modification of the target nucleic acid. Thus, in some cases, a method of binding a target nucleic acid (e.g., a single stranded target nucleic acid) can be a method of modifying the target nucleic acid.

In some cases, the heterologous sequence provides for subcellular localization, i.e., the heterologous sequence is a subcellular localization sequence (e.g., one or more nuclear localization signals (NLSs) for targeting to the nucleus, two or more NLSs, three or more NLSs, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a variant Cas9 does not include a NLS so that the protein is not targeted to the nucleus. In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

In some cases, a Cas9 fusion polypeptide may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 826). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

In some cases, a Cas9 fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., a Cas9 fusion polypeptide). In some embodiments, a PTD is covalently linked to the carboxyl terminus of a polypeptide (e.g., a Cas9 fusion polypeptide). In some cases, the PTD is inserted internally in the Cas9 fusion polypeptide (i.e., is not at the N- or C-terminus of the Cas9 fusion polypeptide) at a suitable insertion site, as described herein. In some cases, a subject Cas9 fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a Cas9 fusion polypeptide includes one or more NLSs (e.g., 2 or more, 3 or more, 4 or more, or 5 or more NLSs). In some embodiments, a PTD is covalently linked to a nucleic acid (e.g., a Cas9 guide nucleic acid, a polynucleotide encoding a Cas9 guide nucleic acid, a polynucleotide encoding a Cas9 fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO: 1076); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSK-LMKR (SEQ ID NO:1077); Transportan GWTLN-SAGYLLGKINLKALAALAKKIL (SEQ ID NO:1078); KALAWEAKLAKALAKALAKHLAKALAKALKCEA (SEQ ID NO:1079); and RQIKIWFQNRRMKWKK (SEQ ID NO: 1080). Exemplary PTDs include but are not limited to, YGRKKRRQRRR (SEQ ID NO:1081), RKKRRQRRR (SEQ ID NO: 1082); an arginine homopolymer of from 3 arginine residues to 50 arginine residues; Exemplary PTD domain amino acid sequences include, but are not limited to, any of the following: YGRKKRRQRRR (SEQ ID NO:1083); RKKRRQRR (SEQ ID NO:1084); YARAAAR-QARA (SEQ ID NO:1085); THRLPRRRRRR (SEQ ID NO:1086); and GGRRARRRRRR (SEQ ID NO:1087). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

A subject Cas9 fusion polypeptide (Cas9 fusion protein) can have multiple (1 or more, 2 or more, 3 or more, etc.) fusion partners in any combination of the above. As an illustrative example, a Cas9 fusion protein can have a heterologous sequence that provides an activity (e.g., for transcription modulation, target modification, modification of a protein associated with a target nucleic acid, etc.) and can also have a subcellular localization sequence. In some cases, such a Cas9 fusion protein might also have a tag for ease of tracking and/or purification (e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). As another illustrative example, a Cas9 protein can have one or more NLSs (e.g., two or more, three or more, four or more, five or more, 1, 2, 3, 4, or 5 NLSs). In some cases a fusion partner (or multiple fusion partners) (e.g., an NLS, a tag, a fusion partner providing an activity, etc.) is located at or near the C-terminus of Cas9. In some cases a fusion partner (or multiple fusion partners) (e.g., an NLS, a tag, a fusion partner providing an activity, etc.) is located at the N-terminus of Cas9. In some cases a Cas9 has a fusion partner (or multiple fusion partners)(e.g., an NLS, a tag, a fusion partner providing an activity, etc.) at both the N-terminus and C-terminus.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some cases, a suitable degron is constitutive such that the degron exerts its influence on protein stability independent of experimental control (i.e., the degron is not drug inducible, temperature inducible, etc.) In some cases, the degron provides the variant Cas9 polypeptide with controllable stability such that the variant Cas9 polypeptide can be turned "on" (i.e., stable) or "off" (i.e., unstable, degraded) depending on the desired conditions. For example, if the degron is a temperature sensitive degron, the variant Cas9 polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 January 18; 33(1): Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals. Thus, fusing Cas9 (e.g., wild type Cas9; variant Cas9; variant Cas9 with reduced nuclease activity, e.g., dCas9; and the like) to a degron sequence produces a "tunable" and "inducible" Cas9 polypeptide. Any of the fusion partners described herein can be used in any desirable combination. As one non-limiting example to illustrate this point, a Cas9 fusion protein (i.e., a chimeric Cas9 polypeptide) can comprise a YFP sequence for detection, a degron sequence for stability, and transcription activator sequence to increase transcription of the target nucleic acid. A suitable reporter protein for use as a fusion partner for a Cas9 polypeptide (e.g., wild type Cas9, variant Cas9, variant Cas9 with reduced nuclease function, etc.), includes, but is not limited to, the following exemplary proteins (or functional fragment thereof): his3, (3-galatosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a Cas9 fusion protein is unlimited. In some cases, a Cas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Examples of various additional suitable fusion partners (or fragments thereof) for a subject variant Cas9 polypeptide include, but are not limited to those described in the PCT patent applications: WO2010075303, WO2012068627, and WO2013155555 which are hereby incorporated by reference in their entirety.

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription include transcription activator and transcription repressor domains (e.g., the Krüppel associated box (KRAB or SKD); the Mad mSIN3 interaction domain (SID); the ERF repressor domain (ERD), etc.). In some such cases, a Cas9 fusion protein is targeted by the guide nucleic acid to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

In some embodiments, the heterologous sequence can be fused to the C-terminus of the Cas9 polypeptide. In some embodiments, the heterologous sequence can be fused to the N-terminus of the Cas9 polypeptide. In some embodiments, the heterologous sequence can be fused to an internal portion (i.e., a portion other than the N- or C-terminus) of the Cas9 polypeptide.

In some embodiments, a Cas9 polypeptide (e.g., a wild type Cas9, a variant Cas9, a variant Cas9 with reduced nuclease activity, a nickase Cas9, etc.) can be linked to a fusion partner via a peptide spacer (e.g., a linker). Exemplary linker polypeptides include glycine polymers $(G)_n$, glycine-serine polymers (including, for example, $(GS)_n$, $GSGGS_n$ (SEQ ID NO: 817), $GGSGGS_n$ (SEQ ID NO: 818), and GGGS$_n$ (SEQ ID NO: 819), where n is an integer of at least one), glycine-alanine polymers, alanine-serine polymers. Exemplary linkers can comprise amino acid sequences including, but not limited to, GGSG (SEQ ID NO: 820), GGSGG (SEQ ID NO: 821), GSGSG (SEQ ID NO: 822), GSGGG (SEQ ID NO: 823), GGGSG (SEQ ID NO: 824), GSSSG (SEQ ID NO: 825), and the like. The ordinarily skilled artisan will recognize that design of a peptide conjugated to any elements described above can include linkers that are all or partially flexible, such that the linker can include a flexible linker as well as one or more portions that confer less flexible structure.

Examples of various Cas9 proteins (and guide RNAs) (e.g., including variant Cas9 proteins, chimeric Cas9 proteins, i.e., Cas9 fusion proteins) can be found in the art, for example, see Jinek et al., Science. 2012 Aug. 17; 337(6096): 816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

A Cas9 protein (e.g., a variant Cas9, a dCas9, a nickase Cas9, a chimeric Cas9, etc.) can be introduced into a cell using any convenient method. For example, the protein can be introduced as a nucleic acid (e.g., DNA or RNA) (e.g., an mRNA, an expression vector, a plasmid, a virus, etc.) encoding the Cas9 protein or can be introduced into a cell directly as protein (e.g., in some cases already complexed with a guide RNA to form a ribonucleoprotein complex, sometimes referred to as an RNP). Thus, for example, a Cas9 fusion protein can be introduced into cells as RNA. Methods of introducing RNA into cells are known in the art and may include, for example, direct injection, transfection, or any other method used for the introduction of DNA. A Cas9 fusion protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Methods of Genome Editing Using an Asymmetric Donor DNA

The present disclosure provides methods of editing DNA of a eukaryotic cell, the methods generally introducing into the cell a Cas9 polypeptide (or a nucleic acid comprising a nucleotide sequence encoding a Cas9 polypeptide), a Cas9 guide RNA (or a nucleic acid comprising a nucleotide sequence encoding a Cas9 guide RNA), and an asymmetric double-stranded or single-stranded donor DNA.

The present disclosure provides a method of editing genomic DNA of a eukaryotic cell, where the genomic DNA comprises a target strand and a non-target strand. In some embodiments, the method comprises introducing into the cell: (a) a Cas9 guide RNA, or one or more nucleic acids encoding the Cas9 guide RNA, where the Cas9 guide RNA hybridizes to a target sequence of the target strand of the genomic DNA; (b) an asymmetric double stranded or single stranded donor DNA molecule comprising a 5' homology arm and a 3' homology arm, where the 3' homology arm is 20 to 50 nucleotides in length, is shorter than the 5' homology arm, and comprises at least 10 consecutive nucleotides of said target sequence; and (c) a Cas9 protein or a nucleic acid encoding the Cas9 protein, where (i) the Cas9 protein forms a complex with the Cas9 guide RNA thereby guiding the Cas9 protein to said target sequence, (ii) the 3' homology arm of the donor DNA molecule hybridizes to the non-target strand of the genomic DNA, and (iii) a nucleotide sequence of the donor DNA molecule is incorporated into the genomic DNA. For example, see FIGS. 14A-14B and FIGS. 15A-15B.

The present disclosure provides a method of editing, in a eukaryotic cell, a double stranded genomic DNA that comprises: (1) a target strand comprising a target sequence, and (2) a non-target strand comprising: a target-sequence-complement that is complementary to the target sequence of the target strand, and a protospacer adjacent motif (PAM) sequence that is immediately adjacent and 3' of the target-sequence-complement, where the method comprises introducing into the cell: (a) a Cas9 guide RNA, or a nucleic acid encoding said Cas9 guide RNA, wherein the Cas9 guide RNA comprises a guide sequence that hybridizes to the target sequence of said target strand; (b) a Cas9 protein, or a nucleic acid encoding said Cas9 protein, wherein the Cas9 protein forms a complex with the Cas9 guide RNA and is thereby targeted to the target sequence of said target strand, wherein the Cas9 protein cleaves at least the non-target strand of the genomic DNA, within said target-sequence-complement, into a PAM distal non-target DNA strand and a PAM proximal non-target DNA strand; and (c) an asymmetric double stranded or single stranded donor DNA molecule comprising: (i) a first homology arm 20 to 50 nucleotides in length that comprises a nucleotide sequence that hybridizes to the PAM distal non-target DNA strand, and (ii) a second homology arm that is 70 to 110 nucleotides in length, is 5' of the first homology arm, and comprises a nucleotide sequence that is complementary to the PAM proximal non-target DNA strand, wherein a nucleotide sequence of the donor DNA molecule is incorporated into the genomic DNA. For example, see FIGS. 14A-14B and FIGS. 15A-15B.

In carrying out a method of the present disclosure for editing a target DNA in a eukaryotic cell, where the donor DNA is an asymmetric donor DNA of the present disclosure, the Cas9 polypeptide can be a 'dead' Cas9 (dCas9); a Cas9 nickase, where the nickase cleaves the non-target strand (e.g., a nickase with a functional RuvC domain); a Cas9 nickase, where the nickase cleaves target strand (e.g., a nickase with a functional HNH domain). Thus, in some cases, the Cas9 is a 'dead' Cas9 (dCas9), and yet genome editing still proceeds despite the lack of cleavage (either a single strand or double strand break in the target DNA). In some cases, the Cas9 is a nickase with a functional RuvC domain (cleaves the non-target strand). In some cases, the Cas9 is nickase with a functional HNH domain (cleaves the target strand). In some cases, the Cas9 includes a functional RuvC domain and a functional HNH domain, and cleaves both the target and non-target strands.

A method of the present disclosure for genome editing, using an asymmetric donor DNA, provides for increased homology-directed repair (HDR) compared to a method that does not involve use of an asymmetric donor DNA. For example, in some cases, a method of the present disclosure for genome editing, using an asymmetric donor DNA, provides for an at least 10%, at least 25%, at least 50%, at least 100%, at least 2.5-fold, at least 5-fold, at least 10-fold, at least 20-fold, at least 30-fold, at least 40-fold, or at least 50-fold increase in HDR, compared with the rate of HDR when the method is carried out using a symmetrical donor DNA template.

In some cases, a method of the present disclosure for genome editing, using an asymmetric donor DNA, provides for an at least 10%, at least 25%, at least 50%, at least 100%, at least 2.5-fold, at least 5-fold, at least 10-fold, at least 20-fold, at least 30-fold, at least 40-fold, or at least 50-fold increase in the number of target genomic DNA molecules that undergo HDR, compared with the number of target genomic DNA molecule that undergo HDR when the method is carried out using a symmetrical donor DNA template.

In some cases, a method of the present disclosure for genome editing, using an asymmetric donor DNA, provides for an at least 10%, at least 25%, at least 50%, at least 100%, at least 2.5-fold, at least 5-fold, at least 10-fold, at least 20-fold, at least 30-fold, at least 40-fold, or at least 50-fold increase in the number of cells of a targeted cell population that undergo HDR, compared with the number of cells of a targeted cell population that undergo HDR when the method is carried out using a symmetrical donor DNA template.

In some cases, a method of the present disclosure for genome editing, using an asymmetric donor DNA, provides for an increased ratio of HDR to NHEJ, compared to the ratio of HDR to NHEJ when the method is carried out using a symmetrical donor DNA template. For example, in some cases, a method of the present disclosure for genome editing, using an asymmetric donor DNA, provides for a ratio of HDR to NHEJ of at least 1:5, at least 1:4, at least 1:3, at least 1:2, at least 1:2, at least 2:1, at least 3:1, at least 4:1, at least 5:1, at least 10:1, or more than 10:1.

Suitable asymmetric donor DNA molecules, Cas9 polypeptides, and guide RNAs are as described above.

The present disclosure provides methods of editing DNA of a eukaryotic cell, the methods generally introducing into the cell a Cas9 polypeptide (or a nucleic acid comprising a nucleotide sequence encoding a Cas9 polypeptide, a Cas9 guide RNA (or a nucleic acid comprising a nucleotide sequence encoding a Cas9 guide RNA), and an asymmetric double-stranded or single-stranded donor DNA. The eukaryotic cell can be referred to as a "target eukaryotic cell." Suitable target eukaryotic cells include in vitro eukaryotic cells, ex vivo eukaryotic cells, and in vivo eukaryotic cells. In some cases, a target eukaryotic cell is an in vitro eukaryotic cell. In some cases, a target eukaryotic cell is an in vivo eukaryotic cell. In some cases, a target eukaryotic cell is an ex vivo eukaryotic cell.

Suitable eukaryotic cells include a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell of an invertebrate animal (e.g. fruit fly, cnidarian, echinoderm, nematode, etc.); a cell of a vertebrate animal (e.g., fish, amphibian, reptile, bird, mammal); a cell of a mammal (e.g., a cell from a rodent such as a mouse or a rat, a cell from a non-human primate, a cell from a human, etc.); and the like.

A suitable eukaryotic cell can be a stem cell (e.g. an embryonic stem (ES) cell, an induced pluripotent stem (iPS) cell); a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be maintained for fewer than 10 passages in vitro. Suitable eukaryotic cells include unicellular organisms, or cells grown in culture.

If the cells are primary cells, they may be harvest from an organism (e.g., an individual) by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells can be frozen in 10% dimethyl sulfoxide (DMSO), 50% serum, 40% buffered medium, or some other such solution as is commonly used in the art to preserve cells at such freezing temperatures, and thawed in a manner as commonly known in the art for thawing frozen cultured cells.

In some embodiments, a target eukaryotic cell is in vitro. In some embodiments, a target eukaryotic cell is in vivo. In some embodiments, a target eukaryotic cell is a plant cell or is derived from a plant cell. In some embodiments, a target eukaryotic cell is an animal cell or is derived from an animal cell. In some embodiments, target eukaryotic cell is an invertebrate cell or is derived from an invertebrate cell. In some embodiments, a target eukaryotic cell is a vertebrate cell or is derived from a vertebrate cell. In some embodiments, a target eukaryotic cell is a mammalian cell or is derived from a mammalian cell. In some embodiments, a target eukaryotic cell is a rodent cell or is derived from a rodent cell. In some embodiments, a target eukaryotic cell is a human cell or is derived from a human cell.

A suitable target eukaryotic cell includes a cell that harbors a genetic defect in its genome, which genetic defect is to be corrected using a method of the present disclosure.

An asymmetric donor DNA system of the present disclosure can be introduced into a host cell by any of a variety of well-known methods. As discussed above, a method of the present disclosure for editing the genome of a eukaryotic cell comprises introducing into the cell: a) a Cas9 polypeptide (or a nucleic acid comprising a nucleotide sequence encoding a Cas9 polypeptide; b) a Cas9 guide RNA (or a nucleic acid comprising a nucleotide sequence encoding a Cas9 guide RNA); and c) an asymmetric double-stranded or single-stranded donor DNA. Thus, in some cases, the method comprises introducing into a target eukaryotic cell: a) a Cas9 polypeptide; b) a Cas9 guide RNA; and c) an asymmetric donor DNA. In other cases, the method comprises introducing into a target eukaryotic cell: a) a Cas9 polypeptide; b) a nucleic acid comprising a nucleotide sequence encoding a Cas9 guide RNA; and c) an asymmetric double-stranded or single-stranded donor DNA. In other instances, the method comprises introducing into a target eukaryotic cell: a) a nucleic acid encoding a Cas9 polypeptide; b) a Cas9 guide RNA; and c) an asymmetric double-stranded or single-stranded donor DNA. In other cases, the method comprises introducing into a target eukaryotic cell: a) a nucleic acid comprising a nucleotide sequence encoding a Cas9 polypeptide; b); b) a nucleic acid comprising a nucleotide sequence encoding a Cas9 guide RNA; and c) an asymmetric double-stranded or single-stranded donor DNA. In any of these embodiments, the Cas9 polypeptide can be an enzymatically active Cas9 polypeptide. In any of these embodiments, the Cas9 polypeptide can be an enzymatically inactive Cas9 polypeptide (a "dead Cas9" polypeptide). In any of these embodiments, the Cas9 polypeptide can be a "nickase" Cas9 polypeptide.

Methods of introducing a nucleic acid into a host cell are known in the art, and any known method can be used to introduce a nucleic acid (e.g., an expression construct) into a target cell. Suitable methods include, include e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

In some cases, a Cas9 polypeptide is provided as a nucleic acid (e.g., an mRNA, a DNA, a plasmid, an expression vector, a viral vector, etc.) that encodes the Cas9 fusion polypeptide. In some cases, the Cas9 polypeptide is provided directly as a protein. A Cas9 polypeptide can be introduced into a cell (provided to the cell) by any convenient method; such methods are known to those of ordinary skill in the art. As an illustrative example, a Cas9 polypeptide can be injected directly into a cell (e.g., with or without nucleic acid encoding a Cas9 guide RNA and with or without a donor polynucleotide). As another example, a preformed complex of a Cas9 polypeptide and a Cas9 guide RNA (an RNP) can be introduced into a cell (e.g., via nucleofection; via a protein transduction domain (PTD) conjugated to one or more components, e.g., conjugated to the Cas9 protein, conjugated to a guide RNA, conjugated to a Cas9 polypeptide and a guide RNA; etc.).

Where a Cas9 polypeptide and/or a Cas9 guide RNA are introduced into a target eukaryotic cell as a nucleic acid comprising a nucleotide sequence encoding the Cas9 polypeptide and/or the Cas9 guide RNA, the nucleotide sequence encoding the Cas9 polypeptide and/or the Cas9 guide RNA can be operably linked to a transcriptional control element (e.g., a promoter) that is functional in a eukaryotic cell. In some cases, the promoter is a constitutively active promoter. In some cases, the promoter is an inducible promoter. In some cases, the promoter is a cell type-specific promoter. Suitable known promoters can be any known promoter and include constitutively active promoters (e.g., CMV promoter), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

System for Genome Editing Comprising Dead Cas9

The present disclosure provides a system for editing genomic DNA in a eukaryotic cell, the system comprising: a) a Cas9 polypeptide that exhibits reduced enzymatic activity; b) a Cas9 guide RNA, or a nucleic acid comprising a nucleotide encoding a Cas9 guide RNA; and c) a double-stranded or single-stranded donor DNA template. For simplicity, a Cas9 polypeptide that exhibits reduced enzymatic activity is referred to herein as a "dead Cas9" polypeptide or a "dCas9" polypeptide. In some cases, the donor DNA template is an asymmetric DNA donor template, as described above.

The present disclosure provides a system for editing genomic DNA in a eukaryotic cell, the system comprising: (a) a dead Cas9 (dCas9) protein, or a nucleic acid encoding said dCas9 protein, where the dCas9 protein lacks catalytically active RuvC and HNH domains; (b) a Cas9 guide RNA, or one or more nucleic acids comprising a nucleotide sequence encoding said Cas9 guide RNA, where the Cas9 guide RNA comprises a guide sequence that is complementary to a target sequence of a target genomic DNA of a eukaryotic cell; and (c) a corresponding double stranded or single stranded donor DNA template molecule comprising at least 10 consecutive nucleotides of said target sequence.

A dCas9 polypeptide for use in the method does not cleave either strand of a target DNA. Interaction of the dCas9, the guide RNA, and the donor DNA is illustrated schematically in FIG. 15A-15B.

dCas9

As noted above, in some cases, a variant Cas9 polypeptide has a reduced ability to cleave both the complementary and the non-complementary strands of a double stranded target nucleic acid. As a non-limiting example, in some cases, the variant Cas9 polypeptide harbors mutations in both the RuvC and HNH domains (e.g., mutations at both the D10 and H840 positions, e.g., both the D10A and the H840A mutations, or the corresponding mutations of any of the proteins set forth as SEQ ID NOs: 5-816) such that the polypeptide has a reduced ability to cleave both the complementary and the non-complementary strands of a double stranded target nucleic acid. Such a Cas9 polypeptide can have a reduced ability to cleave a target nucleic acid but retain the ability to bind a target nucleic acid.

Other residues can be mutated to achieve the above effects (i.e. inactivate one or the other nuclease domains). As non-limiting examples, residues D10, G12, G17, E762, H840, N854, N863, H982, H983, A984, D986, and/or A987 of the Cas9 protein set forth in SEQ ID NO: 5 (or the corresponding residues of any of the proteins set forth as SEQ ID NOs: 6-816) can be altered (i.e., substituted) (e.g., see Table 1 for more information regarding the conservation of Cas9 amino acid residues, e.g., those that are highly conserved and are included in the motifs listed in Table 1). Also, mutations other than alanine substitutions are suitable.

In some embodiments, a variant Cas9 polypeptide that has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the variant Cas9 polypeptide can still bind to target nucleic acid in a site-specific manner (because it is still guided to a target nucleic acid sequence by a guide nucleic acid) as long as it retains the ability to interact with the guide nucleic acid.

Donor DNA

In some cases, the donor DNA template is double stranded. In some cases, the donor DNA template molecule comprises a nucleotide sequence that is a heterologous to the target genomic DNA in the eukaryotic cell.

In some cases, the donor DNA molecule comprises one or more synthetic modifications selected from: a base modification, a sugar modification, and a backbone modification. Suitable base modifications, sugar modifications, and backbone modifications are as described above. For example, in some cases, the donor DNA molecule comprises a phosphorothioate linkage.

In some cases, the contacting occurs under conditions that are permissive for nonhomologous end joining or homology-directed repair. In some cases, the donor polynucleotide, a portion of the donor polynucleotide, a copy of the donor polynucleotide, or a portion of a copy of the donor polynucleotide integrates into the target DNA.

In some cases, a Cas9 guide RNA and a dCas9 polypeptide are coadministered (e.g., contacted with a target nucleic acid, administered to cells, etc.) with a donor polynucleotide sequence that includes at least a segment with homology to the target DNA sequence. In such cases, a method of the present disclosure may be used to add, i.e. insert or replace, nucleic acid material to a target DNA sequence (e.g. to "knock in" a nucleic acid that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, a complex comprising a Cas9 guide RNA and a dCas9 polypeptide is useful in any in vitro, ex vivo, or in vivo application in which it is desirable to modify a target DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into a target DNA sequence, a polynucleotide comprising a donor sequence to be inserted is also provided to the cell. By a "donor sequence" or "donor polynucleotide" it is meant a nucleic acid sequence to be inserted at the site bound by a dCas9 polypeptide (the "target site"). The donor polynucleotide will contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the target site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described above for nucleic acids encoding a Cas9 guide RNA and/or a dCas9 polypeptide and/or donor polynucleotide.

Asymmetric Donor DNA

In some cases, the donor DNA is an asymmetric donor DNA, as described above. For example, in some cases, the donor DNA is an asymmetric donor DNA molecule comprising a 5' homology arm and a 3' homology arm, wherein the 3' homology arm is 20 to 50 nucleotides in length, is shorter than the 5' homology arm, and comprises the at least 10 consecutive nucleotides of said target sequence. In some cases, the donor DNA template molecule is single stranded. In some cases, the donor DNA template molecule is double stranded. Asymmetric donor DNA is as described above.

Guide RNA

In some cases, a dCas9 system of the present disclosure comprises only one guide RNA, which may be a single-guide RNA or a dual-guide RNA. Suitable guide RNAs are as described above.

In some cases, the guide RNA comprises one or more synthetic modifications selected from: a base modification, a sugar modification, and a backbone modification. Suitable base modifications, sugar modifications, and backbone modifications are as described above. For example, in some cases, the guide RNA comprises a phosphorothioate linkage.

In some cases, a dCas9 system of the present disclosure comprises two or more Cas9 guide RNAs, or one or more nucleic acids encoding the two or more Cas9 guide RNAs, wherein the guide sequences of the two or more Cas9 guide RNAs are complementary to target sequences that do not overlap with one another and are each separated from one another by 1-100 nucleotides; e.g., are separated from one another by from 1 nt to 5 nt, from 5 nt to 10 nt, from 10 nt to 15 nt, from 15 nt to 20 nt, from 20 nt to 25 nt, from 25 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some cases, the two or more Cas9 guide RNAs are complementary to target sequences that overlap with the donor DNA template molecule.

In some cases, a dCas9 system of the present disclosure comprises three or more Cas9 guide RNAs, or one or more nucleic acids encoding the three or more Cas9 guide RNAs, wherein the guide sequences of the three or more Cas9 guide RNAs are complementary to target sequences that do not overlap with one another and are each separated from one another by 1-100 nucleotides; e.g., are separated from one another by from 1 nt to 5 nt, from 5 nt to 10 nt, from 10 nt to 15 nt, from 15 nt to 20 nt, from 20 nt to 25 nt, from 25 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some cases, the three or more Cas9 guide RNAs are complementary to target sequences that overlap with the donor DNA template molecule.

In some cases, a dCas9 system of the present disclosure comprises four or more Cas9 guide RNAs, or one or more nucleic acids encoding the four or more Cas9 guide RNAs, wherein the guide sequences of the four or more Cas9 guide RNAs are complementary to target sequences that do not overlap with one another and are each separated from one another by 1-100 nucleotides; e.g., are separated from one another by from 1 nt to 5 nt, from 5 nt to 10 nt, from 10 nt to 15 nt, from 15 nt to 20 nt, from 20 nt to 25 nt, from 25 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some cases, the four or more Cas9 guide RNAs are complementary to target sequences that overlap with the donor DNA template molecule.

Cells

A system of the present disclosure that comprises a dCas9 polypeptide, a guide RNA (or one or more nucleic acids comprising nucleotide sequences encoding the guide RNA), and a donor DNA (or a nucleic acid comprising a nucleotide sequence encoding the donor DNA) can in some cases further include a eukaryotic cell comprising said target genomic DNA.

Suitable eukaryotic cells include, but are not limited to, plant cells; algal cells; fungal cells; unicellular eukaryotic organisms (including pathogenic unicellular eukaryotic organisms); reptile cells; amphibian cells; insect cells; arthropod cells; and mammalian cells (e.g., ungulate cells (e.g., bovine cells, ovine cells, caprine cells, equine cells, etc.); feline cells; canine cells; non-human primate cells; human cells). Suitable cells include stem cells, including embryonic stem cells and adult stem cells; progenitor cells; hepatic cells; lymphocytes; oligodendrocytes; neurons; and the like.

Methods of Genome Editing Using Dead Cas9

The present disclosure provides a method of editing a target genomic DNA in a eukaryotic cell. The method generally involves introducing into the cell: a) a dead Cas9 polypeptide, or a nucleic acid comprising a nucleotide encoding a dead Cas9 polypeptide; b) a Cas9 guide RNA, or one or more nucleic acids comprising nucleotide sequences encoding a Cas9 guide RNA; and c) a single-stranded or double-stranded DNA donor template comprising at least 10 consecutive nucleotides of the a target sequence in the target genomic DNA. Suitable eukaryotic cells are as described above. Suitable guide RNAs are as described above. Suitable donor DNA templates are as described above. In some cases, the method comprises introducing into an in vitro eukaryotic cell: a) a dead Cas9 polypeptide, or a nucleic acid comprising a nucleotide encoding a dead Cas9 polypeptide; b) a Cas9 guide RNA, or one or more nucleic acids comprising nucleotide sequences encoding a Cas9 guide RNA; and c) a single-stranded or double-stranded DNA donor template comprising at least 10 consecutive nucleotides of the a target sequence in the target genomic DNA. In some cases, the method comprises introducing into an in vivo eukaryotic cell: a) a dead Cas9 polypeptide, or a nucleic acid comprising a nucleotide encoding a dead Cas9 polypeptide; b) a Cas9 guide RNA, or one or more nucleic acids comprising nucleotide sequences encoding a Cas9 guide RNA; and c) a single-stranded or double-stranded DNA donor template comprising at least 10 consecutive nucleotides of the a target sequence in the target genomic DNA.

The present disclosure provides a method of editing a target genomic DNA of a eukaryotic cell, the method comprising introducing into the eukaryotic cell: (a) a dead Cas9 (dCas9) protein, or a nucleic acid encoding said dCas9 protein, wherein the dCas9 protein does not cleave the target genomic DNA; (b) a Cas9 guide RNA, or one or more nucleic acids encoding said Cas9 guide RNA, wherein the Cas9 guide RNA hybridizes to a target sequence of the target genomic DNA; and (c) a corresponding double stranded or single stranded donor DNA template molecule comprising at least 10 consecutive nucleotides of said target sequence, where the dCas9 protein forms a complex with the Cas9 guide RNA thereby guiding the dCas9 protein to said target sequence, and wherein a nucleotide sequence of the donor DNA molecule is incorporated into the genomic DNA.

In some cases, the method comprises introducing comprises introducing two or more Cas9 guide RNAs, or one or more nucleic acids encoding the two or more Cas9 guide RNAs into a eukaryotic cell comprising a target DNA, where the two or more Cas9 guide RNAs hybridize to target sequences that do not overlap with one another and are each separated from one another by from 1-100 nucleotides. In some cases, the method comprises introducing comprises introducing two or more Cas9 guide RNAs, or one or more nucleic acids encoding the two or more Cas9 guide RNAs into a eukaryotic cell comprising a target DNA, where the two or more Cas9 guide RNAs hybridize to target sequences that do not overlap with one another and are each separated from one another by from 1 nt to 5 nt, from 5 nt to 10 nt, from 10 nt to 15 nt, from 15 nt to 20 nt, from 20 nt to 25 nt, from 25 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some cases, the two or more Cas9 guide RNAs hybridize to target sequences that overlap with the donor DNA template molecule.

In some cases, the method comprises introducing comprises introducing three or more Cas9 guide RNAs, or one or more nucleic acids encoding the three or more Cas9 guide RNAs into a eukaryotic cell comprising a target DNA, where the three or more Cas9 guide RNAs hybridize to target sequences that do not overlap with one another and are each separated from one another by 1-100 nucleotides. In some cases, the method comprises introducing comprises introducing three or more Cas9 guide RNAs, or one or more nucleic acids encoding the three or more Cas9 guide RNAs into a eukaryotic cell comprising a target DNA, where the three or more Cas9 guide RNAs hybridize to target sequences that do not overlap with one another and are each separated from one another by from 1 nt to 5 nt, from 5 nt to 10 nt, from 10 nt to 15 nt, from 15 nt to 20 nt, from 20 nt to 25 nt, from 25 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some cases, the three or more Cas9 guide RNAs hybridize to target sequences that overlap with the donor DNA template molecule.

In some cases, the method comprises introducing comprises introducing four or more Cas9 guide RNAs, or one or more nucleic acids encoding the four or more Cas9 guide RNAs into a eukaryotic cell comprising a target DNA, where the four or more Cas9 guide RNAs hybridize to target sequences that do not overlap with one another and are each separated from one another by 1-100 nucleotides. In some cases, the method comprises introducing comprises introducing four or more Cas9 guide RNAs, or one or more nucleic acids encoding the four or more Cas9 guide RNAs into a eukaryotic cell comprising a target DNA, where the four or more Cas9 guide RNAs hybridize to target sequences that do not overlap with one another and are each separated from one another by from 1 nt to 5 nt, from 5 nt to 10 nt, from 10 nt to 15 nt, from 15 nt to 20 nt, from 20 nt to 25 nt, from 25 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some cases, the four or more Cas9 guide RNAs hybridize to target sequences that overlap with the donor DNA template molecule.

Suitable eukaryotic cells include, but are not limited to, plant cells; algal cells; fungal cells; unicellular eukaryotic organisms (including pathogenic unicellular eukaryotic organisms); reptile cells; amphibian cells; insect cells; arthropod cells; and mammalian cells (e.g., ungulate cells (e.g., bovine cells, ovine cells, caprine cells, equine cells, etc.); feline cells; canine cells; non-human primate cells; human cells). Suitable cells include stem cells, including embryonic stem cells and adult stem cells; progenitor cells; hepatic cells; lymphocytes; oligodendrocytes; neurons; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Materials and Methods
Cas9 and RNA Preparation

Cas9 (pCR1002), dCas9 (pCR1003), Cas9-2NLS (pCR1053), D10ACas9-2NLS (pCR1054), H840ACas9-2NLS (pCR1055), and dCas9-2NLS (pCR1056) were purified by a combination of affinity, ion exchange, and size exclusion chromatographic steps as previously described[22], except protein was eluted at 40 uM in 20 mM HEPES KOH pH 7.5, 5% glycerol, 150 mM KCl, 1 mM dithiothreitol (DTT). FIG. 18 contains the expressed sequences for each of these vectors.

Single guide RNAs (sgRNAs) were generated by HiScribe (NEB E2050S) T7 in vitro transcription using PCR-generated DNA as a template[22] ("dx.doi" followed by ".org/10.17504/protocols" followed by ".io.dm749m"). Sequences for the sgRNA templates can be found in FIG. 17.

BioLayer Interferometry

The Octet RED384 BioLayer Interferometry machine and Streptavidin (SA) Biosensors are available from ForteBio (Menlo Park, Calif.). All steps were performed in Reaction Buffer (20 mM Tris pH 7.0, 100 mM KCl, 5 mM $MgCl_2$, 1 mM DTT, 0.01% Tween, 50 μg/mL Heparin) at 37° C. Biosensors were incubated with 300 nM double stranded DNA (Single ribonucleoprotein (RNP) Substrate) biotinylated on the 5' terminus of the non-target strand for 180 seconds and free DNA was washed away. 200 nM Cas9 (expressed from pCR1002) or dCas9 (expressed from pCR1003) were mixed with a 20% molar excess of sgRNA and incubated for 10 minutes to form RNP. Biosensor tips conjugated to substrate DNA were incubated with RNP for 300 seconds to load RNP. Biosensor-double stranded DNA (dsDNA)-RNP complexes were allowed to dissociate in Reaction Buffer for 3600 seconds. Response curves for each biosensor were normalized against biosensors conjugated to DNA but without RNP (buffer-only control). Normalized response curves were processed using Octet software version 7 to obtain reported kinetic values.

EMSA Assays

Nuclease and sgRNA were incubated in Reaction Buffer for 30 minutes to form RNP. Substrate DNA was added and RNP loading was allowed to take place for a defined interval (16 hours, equilibrium experiments; ten minutes, strand displacement/annealing experiments). Assembled RNP-dsDNA complexes were incubated with challenge DNA for the reported amount of time. Standard reactions conditions were: Substrate DNA—100 nM, Cas9-500 nM, sgRNA—500 nM, Challenge DNA—1500 nM. All reactions were performed at 37° C. Sequences for the substrate and challenge oligonucleotides (IDT) can be found in FIG. 17.

Cell Lines

HEK293 cells were obtained from ATCC and verified mycoplasma-free (Lonza Mycoalert LT-07). All cells were maintained in DMEM supplemented with 10% FBS and 100 μg/mL Penicillin-Streptomycin.

Reporter Strain Construction

HEK293 cells were transduced with lentivirus expressing a BFP reporter construct under the EF1 alpha promoter (Addgene Deposit Pending). Dilution cloning was used to isolate clonal populations with robust expression of Blue fluorescent protein (BFP) (as measured by flow cytometry). Cell populations were periodically sorted on a BD FACSJAZZ to maintain BFP expression levels.

Nucleofection Editing Experiments 100 pmoles of Cas9-2NLS (or variants) was diluted to a final volume of 5 uL with Cas9 buffer (20 mM HEPES (pH 7.5), 150 mM KCl, 1 mM $MgCl_2$, 10% glycerol and 1 mM tris (2-carboxyethyl)phosphine (TCEP)) and mixed slowly into 5 uL of Cas9 buffer containing 120 pmoles of L2 sgRNA. The resulting mixture was incubated for ten minutes at RT to allow RNP formation. $2\times10^5$ HEK293 cells were harvested, washed once in PBS, and resuspended in 20 uL of SF nucleofection buffer (Lonza, Basel, Switzerland). 10 uL of RNP mixture, 100 pmoles of donor DNA, and cell suspension were combined in a Lonza 4d strip nucleocuvette. Reaction mixtures were electroporated using setting DS150, incubated in the nucleocuvette at RT for ten minutes, and transferred to culture dishes containing pre-warmed media ("dx.doi" followed by ".org/10.17504/protocols" followed by ".io.dm649d"). Editing outcomes were measured four and seven days post-nucleofection by flow cytometry. Seven-day results are presented in the figures.

Terminal Transferase-qPCR Assay 667 pmoles of Cas9-2NLS (or variants) was diluted to a final volume of 20 uL with Cas9 buffer and mixed slowly into 20 uL of Cas9 buffer containing 800 pmoles of sgRNA. The resulting mixture was incubated for ten minutes at RT to allow RNP formation. $4\times10^6$ cells were harvested, washed once in PBS, and resuspended in 100 uL of SF nucleofection buffer (Lonza V4XC-2032). 50 uL of RNP mixture, 100 pmoles of donor DNA, and cell suspension were combined in a Lonza 4d strip nucleocuvette. Reaction mixtures were electroporated using setting DS150, incubated in the nucleocuvette at RT for ten minutes, and transferred to culture dishes containing pre-warmed media. Cells were allowed to recover for three hours, then fixed in 2% formaldehyde for 15 minutes at 4° C. and permeablized overnight in 70% ethanol at −20° C. $1\times10^6$ cells were rehydrated in terminal transferase (TdT) buffer (Roche 03333574001) for ten minutes at 37° C. and incubated with 800 U of TdT and 2 nmoles of Biotin-16-dUTP (Roche 11093070910) for 30 minutes at 37° C. Labeled cells were resuspended in Lysis Buffer (50 mM Tris, pH 7.4, 500 mM NaCl, 0.4% SDS, 5 mM EDTA, 1 mM DTT) and disrupted by sonication in a Covaris S220. Crosslinks were reversed by incubation for 4 hours at 65° C. and cell slurry was cleared by centrifugation at max speed for ten minutes.

Biotinylated DNA in the supernatant was bound to streptavidin MyOne C1 Dynabeads (Life Technologies 65002) and washed 3× in Wash Buffer (5 mM Tris, 0.5 mM EDTA, 1M NaCl). Non-biotinylated strands were dissociated by incubation in 20 mM NaOH for ten minutes. The washed beads were resuspended to a final concentration of 10 ug/uL in $dH_2O$. Two microliters of bead slurry was used as template for qPCR.

A total of three independent cultures were analyzed for each sgRNA on an Eppendorf Nexus X1 qPCR machine using primers listed in FIG. 17. Each reaction was performed using DyNAmo HS SYBR Green qPCR kit (Fisher Scientific F-410L) in a total volume of 20 μL with primers at a final concentration of 300 nM. Annealing was performed at 62° C. Fold enrichment of the assayed DNA segments over the un-labeled ACT1B locus was calculated using the $2^{-\Delta\Delta Ct}$ method essentially as described[23].

Results

Figure 5A:
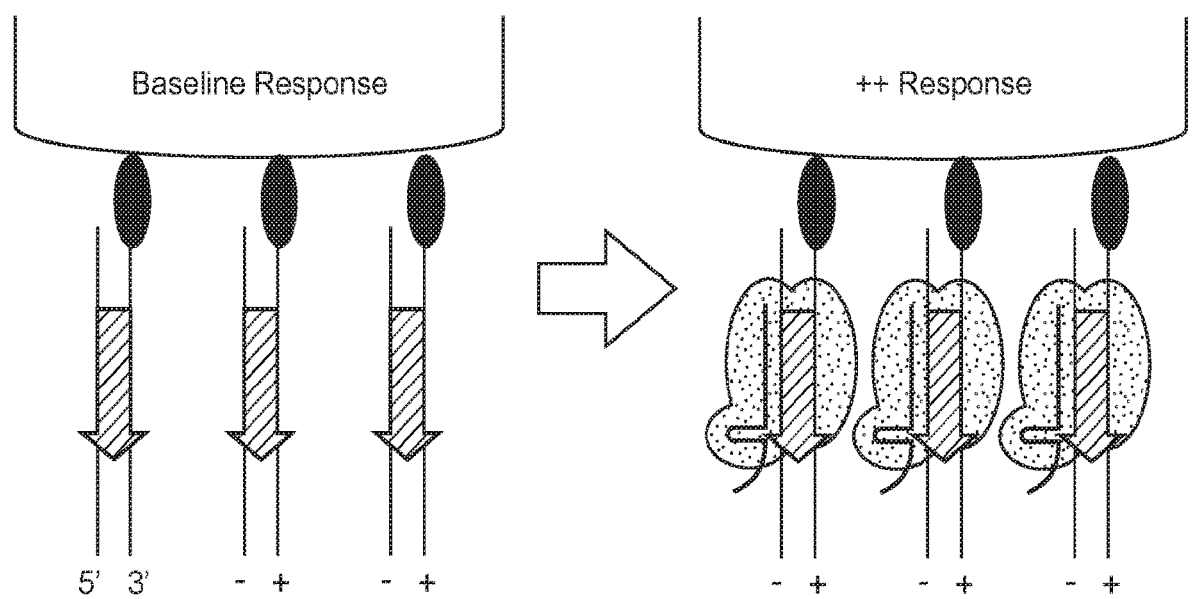
FIG. 5A-5E depicts association and dissociation of Cas9 and Cas9 variants from substrate DNA.
Figure 5B:
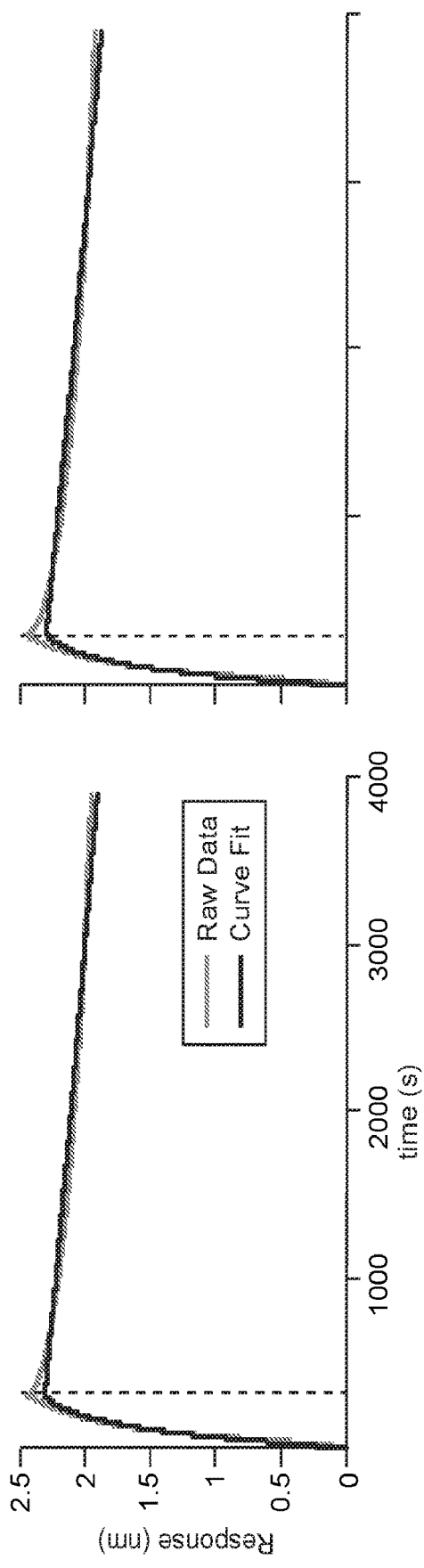
Figure 5B:
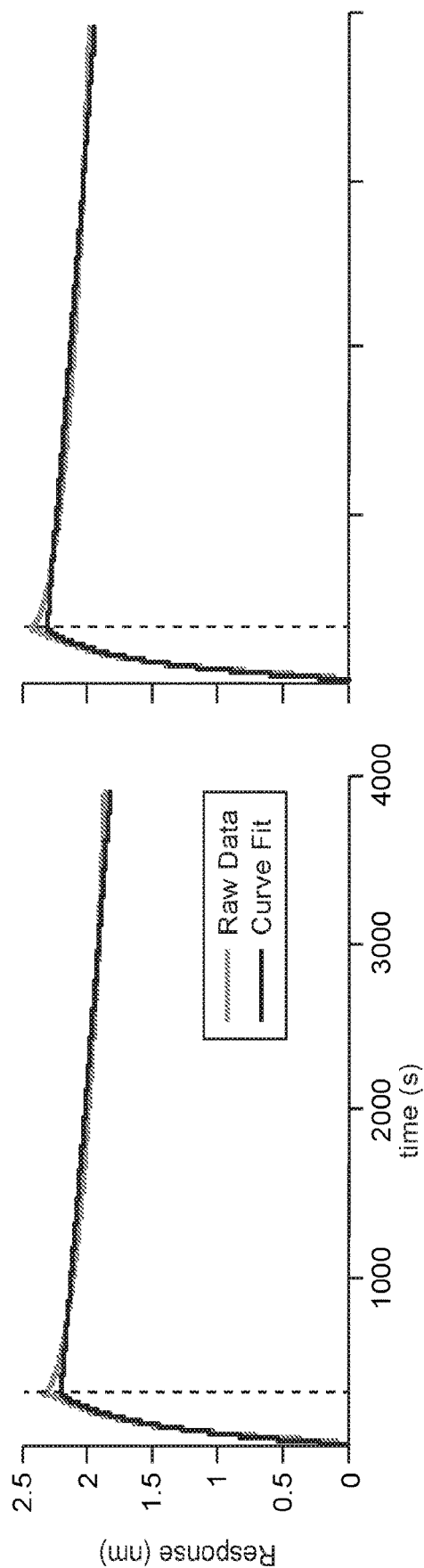
Figure 5C:
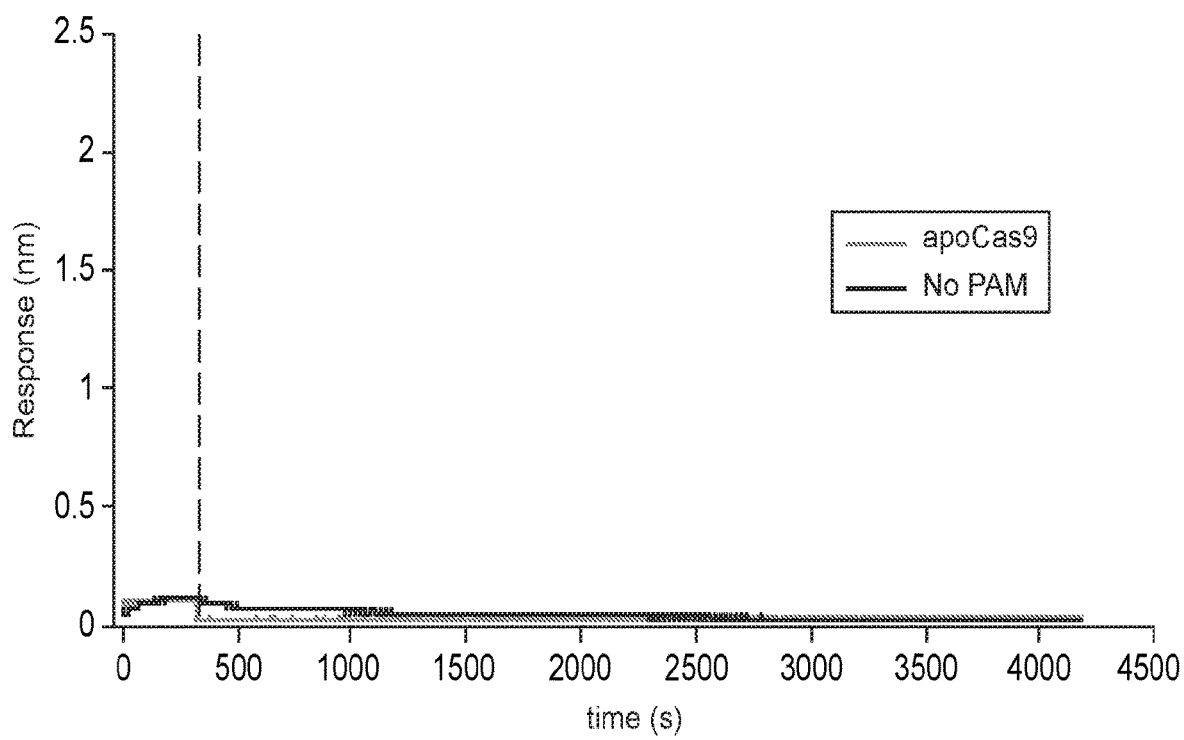
Figure 5D:
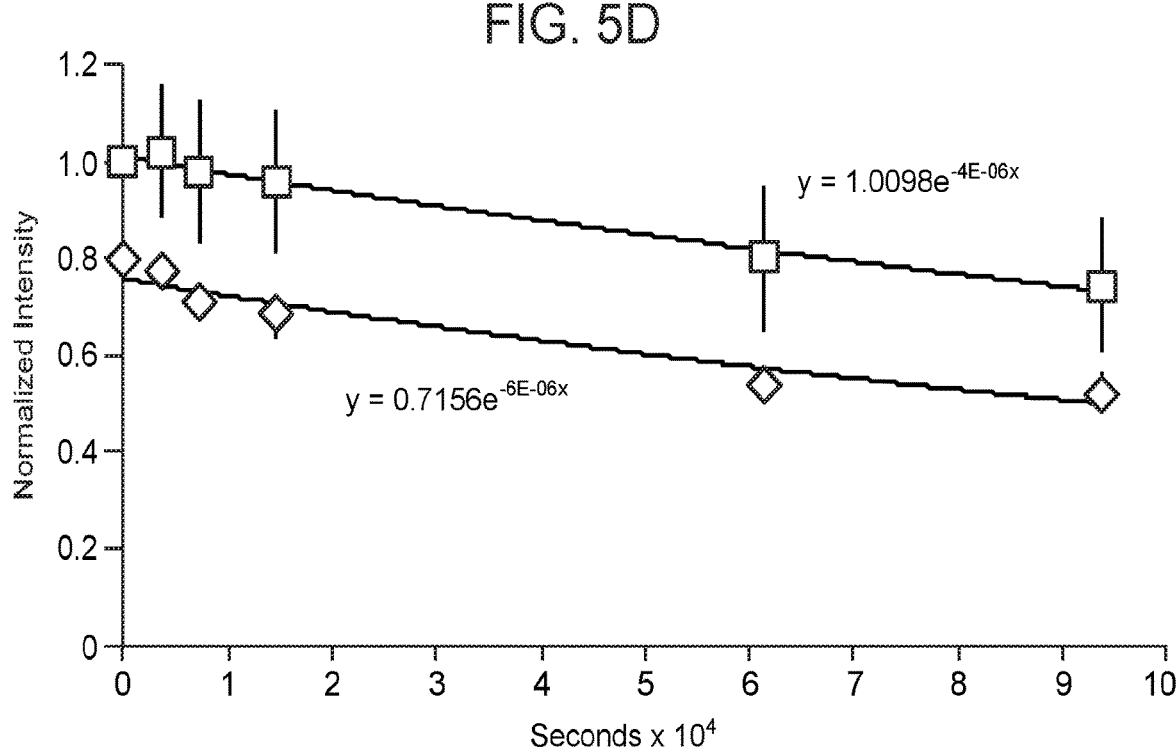

Bio-Layer Interferometry (BLI) was used to determine the in vitro kinetics of RNP interaction with substrate DNA under native conditions[13]. A biotinylated 55 base pair substrate DNA (1 described in[12]) was immobilized to a streptavidin-coated BLI probe, and the binding and dissociation of Cas9 or catalytically inactive dCas9 was measured (FIG. 5A). Despite the ability of Cas9 to cleave the target DNA (FIG. 5E), it was observed that both proteins have identical affinities for DNA ($K_D$ 1.2±0.1 nM, FIG. 1A and FIG. 5B), as well as identical off rates of ~5.0±0.3×10$^{-5}$ s$^{-1}$, which equates to a lifetime of 5.5 hours. The tight interaction of both RNP variants with substrate DNA was sgRNA-dependent and required a protospacer adjacent motif (PAM) (FIG. 5C). To resolve whether Cas9 preferentially dissociates from one end of cut duplex DNA under physiological conditions, substrate DNA on each side of the nuclease cut site were labeled with a distinct fluorophore and dissociation of cut fragments was monitored using an electrophoretic mobility shift assay (EMSA). By chasing with unlabeled duplex competitor DNA, the off rate of the PAM-distal side of the cut at $1\times10^{-5}$ $s^{-1}$ and the off-rate of the PAM-proximal side of the cut at $6\times10^{-6}$ $s^{-1}$ was determined (FIG. 1B and FIG. 5D), which is very similar to values measured by BLI. Cas9's lifetime on DNA is therefore approximately 5-fold longer than the lower bound previously established by fluorescent means[12], and under native conditions symmetrically dissociates from the target duplex. The in vitro Cas9-DNA lifetime is similar to the time required to repair Cas9 lesions in mammalian cells (6-24 hours)[14], but longer than the time required to repair double strand breaks caused by ionizing radiation ($t_{1/2}$=60 minutes)[15]. Thus, Cas9 may bind so stably to substrate DNA that it conceals the underlying double strand break and limits its recognition by genome surveillance factors.

Figure 1B:
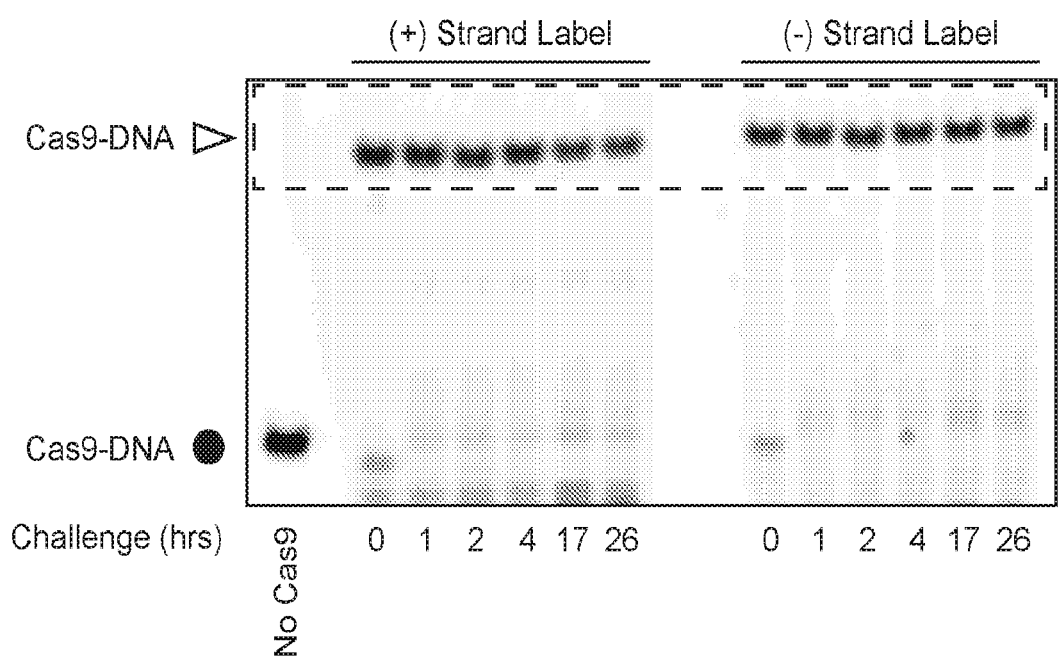

FIG. 1: Cas9 interacts stably with substrate DNA. (FIG. 1A) Bio-layer interferometry measurements of association (left of dotted line) and dissociation (right of dotted line) of Cas9 (black trace) or dCas9 (brown trace) with 1 dsDNA. Mean±standard deviation (SD) kinetic values calculated from n=2 experiments are inset. See FIG. 5 for all experiments and data fitting. (FIG. 1B) Electrophoretic mobility shift assay (EMSA) measuring dissociation of Cas9 from substrate dsDNA. Cas9 RNP was equilibrated with S1 dsDNA for 16 hours, after which unlabeled challenge dsDNA was added for the indicated time and reaction products were visualized on a native polyacrylamide gel. Black circle, labeled substrate DNA (no Cas9); open triangle, Cas9-DNA complex; region of interest, dashed box. Data shown is representative of n=2 experiments. Subsequent figures highlight the region of interest corresponding to the dashed lines.

FIG. 5: (FIG. 5A) Schematic of BLI assay used to measure dissociation. 5' monobiotinylated substrate DNA (identical to λ1, FIG. 2A-2E) is associated with streptavidin-coated sensor tips (black oval) and baseline signal is established (left panel). Association phase (right panel) loads Cas9 onto substrate dsDNA and measures response. Dissociation phase (not shown) transfers the tip into buffer and monitors dissociation of Cas9. (FIG. 5B) Fit between BLI data (thick trace) and calculated kinetic values (maroon trace) for Cas9 (black) and dCas9 (brown). Replicate data is shown. (FIG. 5C) Cas9 interacts specifically with substrate dsDNA. BLI traces show no interaction of apoCas9 (no sgRNA) with substrate dsDNA (maroon trace) or Cas9 with substrate dsDNA lacking a PAM (blue trace). (n=2). (FIG. 5D) Gel densitometry of FIG. 1B. Mean±SD normalized intensity of + strand (blue) and − strand (red) shifted products were plotted as a function of time. The indicated regression lines were used to calculate $k_{off}$. (FIG. 5E) Cas9, Cas9D10A, and Cas9H840A cleave DNA while dCas9 does not. Cas9 nucleases were incubated with or without sgRNA for 30 minutes and associated with 1 substrate DNA (FIG. 2A) for ten minutes. Untagged (pCR1002 and pCR1003, FIG. 18) and NLS-tagged (pCR1053-pCR1056, FIG. 18) Cas9 variants were tested and found to have equivalent activity. -Reaction products were resolved on a 10% TBE-Urea gel. Open arrow, uncut substrate DNA; *, excess Cy5 labeled ssDNA; ‡, excess Cy3 labeled ssDNA. Data presented is representative of n=2 experiments.

Figure 2A:
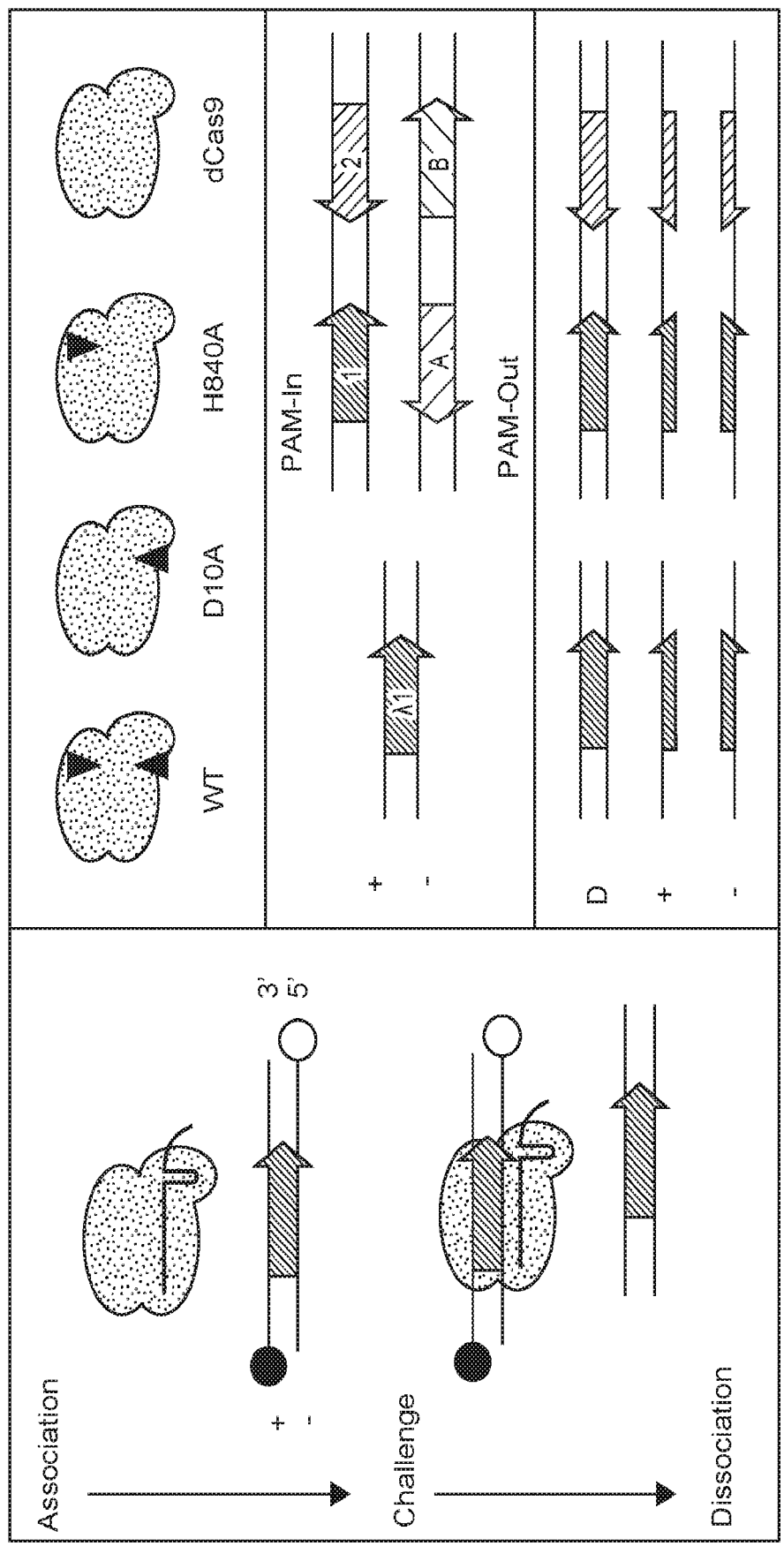
FIG. 2A-2E depicts data showing that complementary DNA anneals to the non-target strand of the RNP-dsDNA complex.
Figure 2B:
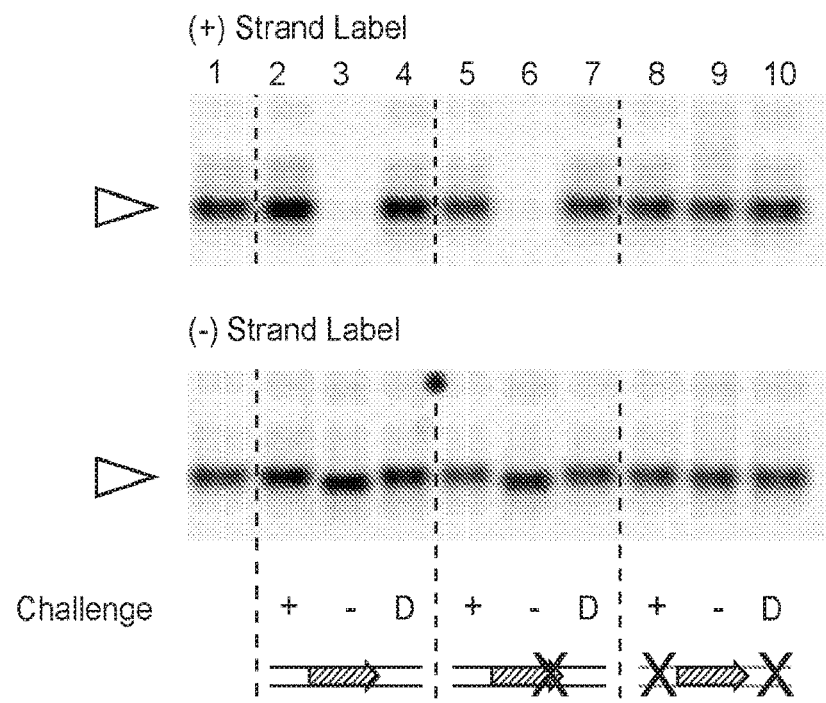
Figure 2C:
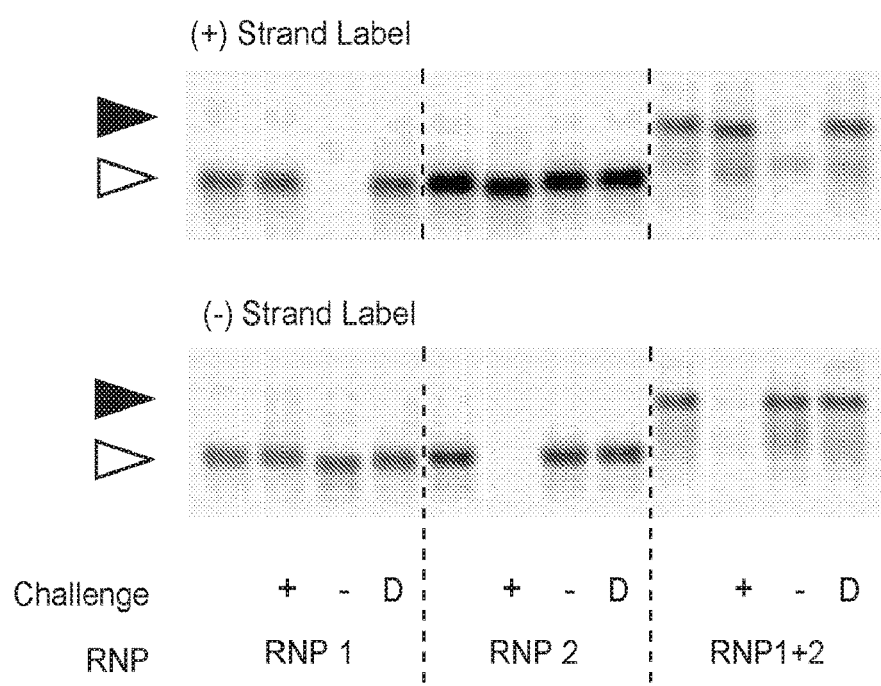
Figure 6:
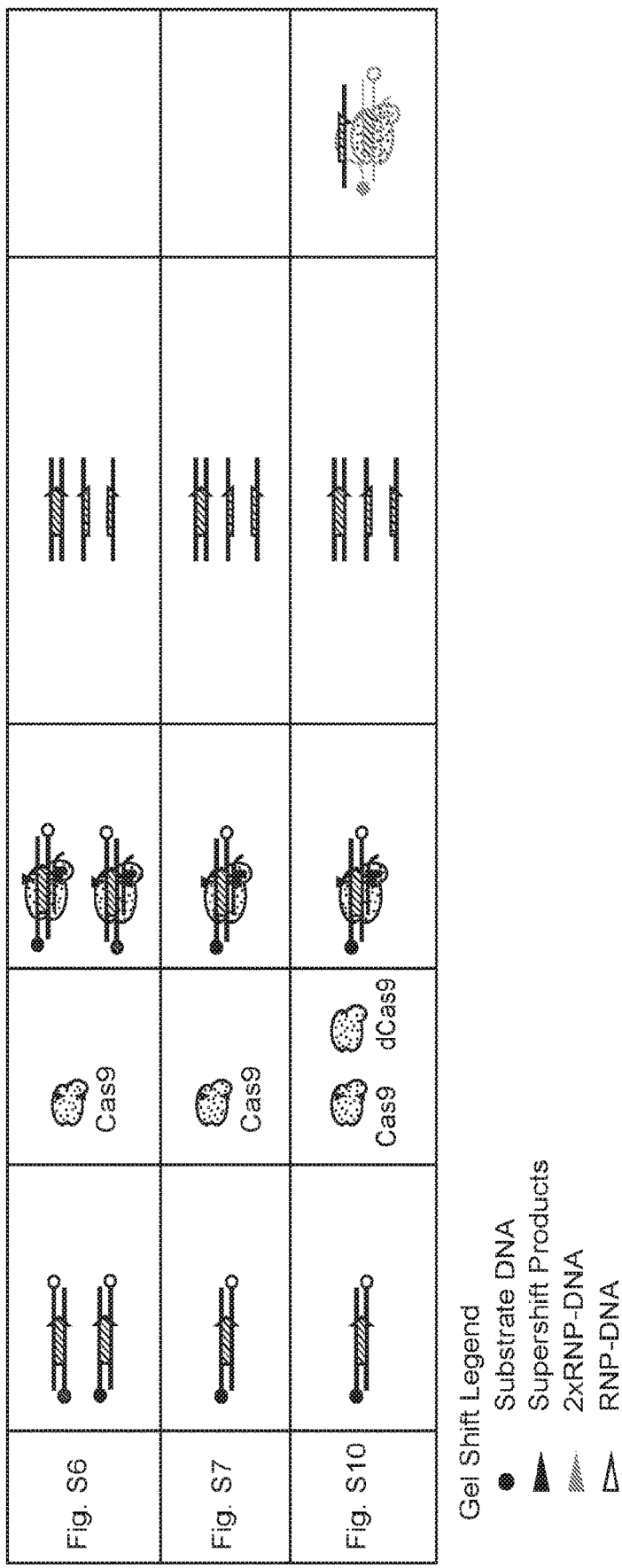
FIG. 6 depicts a schematic of reagents and experimental design for various EMSA experiments.
Figure 7A:
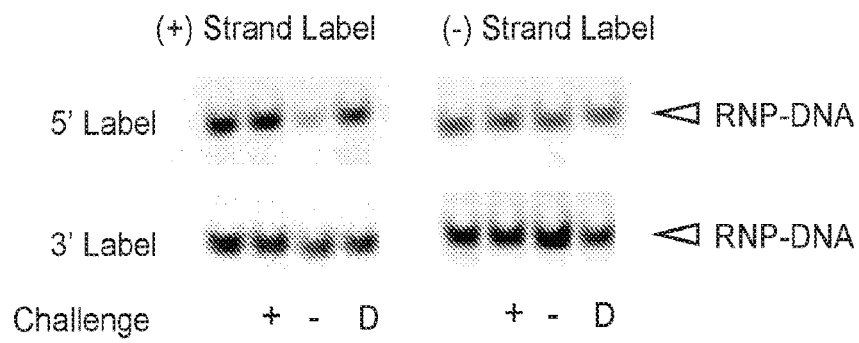
FIG. 7A-7C depicts removal of non-target strand by challenge DNA.
Figure 7B:
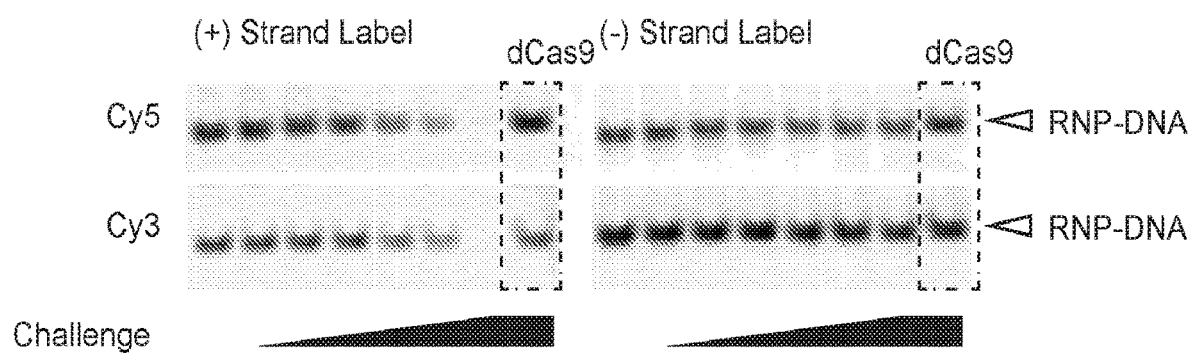
Figure 8:
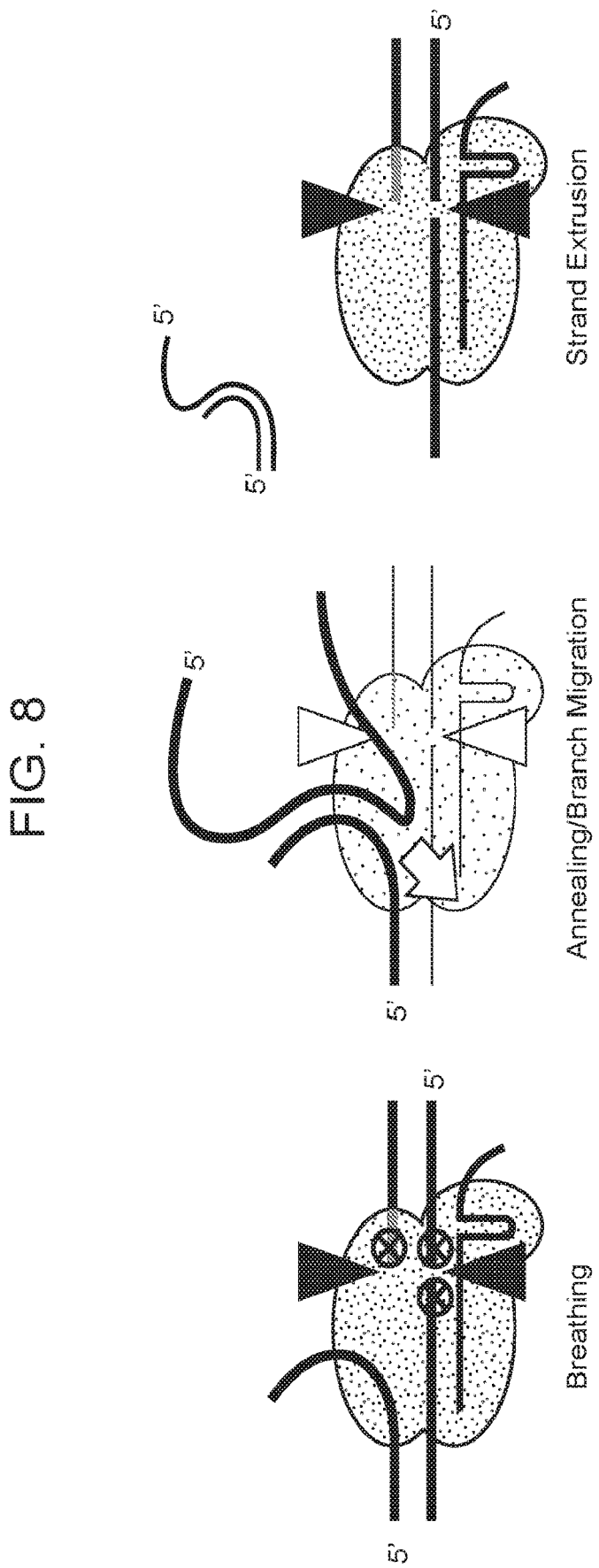
FIG. 8 depicts a model for challenge-mediated non-target strand removal activity.

To identify intermediate species that form during Cas9-mediated DNA cleavage, the Cas9-DNA complex was challenged with unlabeled DNA of various compositions (FIG. 2A and FIG. 6). Surprisingly, incubation of Cas9-DNA with an excess of single stranded DNA (ssDNA) identical to the target strand caused the fluorophore attached to the 5' end of the non-target strand to be lost from the complex, while a fluorophore attached to the 5' end of the target strand was not affected by either double or single stranded challenge DNA (FIG. 2B, lanes 2-4). By systematically labeling the 5' or 3' termini of either strand of the substrate DNA, it was found that target strand challenge DNA removes the PAM-distal non-target strand from the Cas9-DNA complex without affecting the other three strands (FIG. 7A). This strand-removal activity required sequence complementarity between Cas9-bound DNA and challenge DNA outside the protospacer sequence (FIG. 2B, lanes 8-10), but the PAM sequence of challenge DNA was dispensable (FIG. 2B, lanes 5-7). These results, and the appearance of a new, fluorescently-labeled product whose size is consistent with cleaved non-target strand annealed to challenge DNA (FIG. 2B), indicate that single stranded challenge DNA does not compete for Cas9 binding, but instead anneals to the non-target strand. Strand removal was dependent on the concentration of this challenge DNA, as well as nuclease activity (FIG. 7B). By recruiting two RNP complexes to a single target DNA in a PAM-Inward orientation, as is used in paired-nick editing experiments[16], it was found that the PAM-distal non-target strand could be removed from each complex with the appropriate challenge ssDNA (FIG. 2C). Hence, while Cas9 globally dissociates from duplex DNA in a symmetric fashion (FIG. 1B), it appears that the enzyme locally releases the PAM-distal non-target strand after cleavage but before dissociation. This strand is furthermore available for annealing to complementary challenge DNA and can be extruded from the Cas9-DNA complex by branch migration (FIG. 8).

Figure 5E:
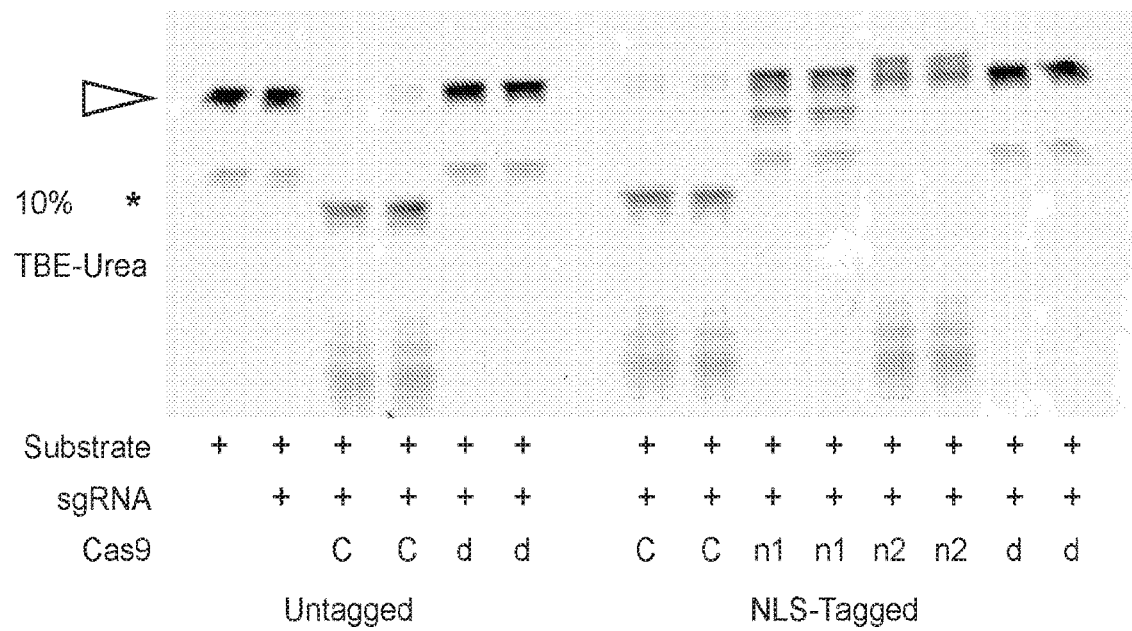
Figure 5E:
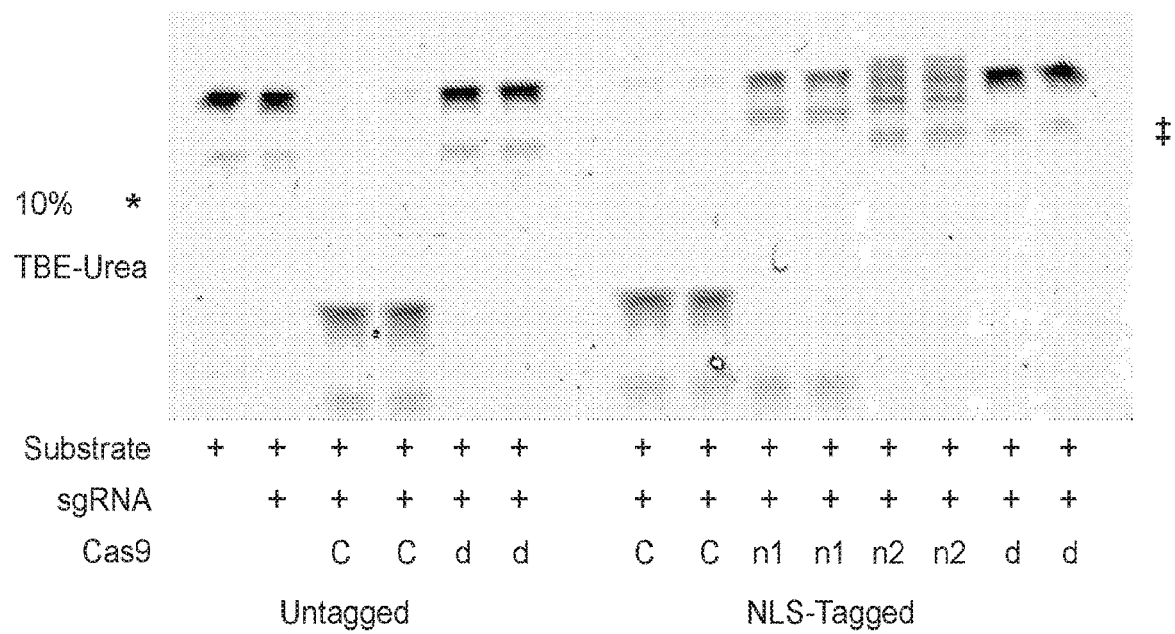

FIG. 2: Complementary DNA anneals to the non-target strand of the RNP-dsDNA complex. (FIG. 2A) Schematic for EMSA assays. Association: RNP is equilibrated for 10 minutes with fluorescently labeled substrate DNA (magenta, Cy5; green, Cy3) containing protospacer-PAM sequences (blue and green arrows); Challenge/Dissocation: reactions are incubated with or without unlabeled challenge DNA for ten minutes and products are resolved on a native polyacrylamide gel. Nuclease variants (top right inset) are WT (two magenta arrows representing catalytically active nuclease domains), the Cas9D10A and Cas9H840A nickase variants (single magenta arrow), and the catalytically dead D10A/H840A dCas9 variant. DNA substrates (middle right inset) contain one or two protospacer-PAM sequences (arrows). Dual binding of RNP to substrate DNA was investigated using sgRNA pairs that targeted protospacer-PAM sites in PAM-In (1 and 2) or PAM-Out (A and B) orientations. Unlabeled challenge DNA (lower right inset) was provided as double-stranded (D) or single stranded (+ or −) species. Data presented are representative of n=2 biological replicates and cropped to highlight the region of interest. The Cas9, sgRNA, and substrate DNA for each EMSA experiment is schematically presented in FIG. 6. Nuclease activity was verified using denaturing gels (FIG. 5E). (FIG. 2B) Challenging a stable Cas9-DNA complex with ssDNA complementary to the PAM-distal non-target strand leads to removal of this strand from the complex. Challenge DNAs were identical to substrate DNA (S1 substrate challenge; lanes 2-4), identical to substrate DNA with PAM disrupted (S1 pam− challenge; lanes 5-7), or disrupted the complementarity of the sequence flanking the protospacer-PAM (S1 nh− challenge; lanes 8-10). Open triangle, RNP-DNA complex. (FIG. 2C) Loading multiple Cas9 molecules in a PAM-In orientation allows displacement of either PAM-distal non-target strand. One or two Cas9 molecules were loaded onto D1 substrate DNA, then challenged with the indicated challenge DNA species. Open triangle, RNP-DNA; solid grey triangle, 2×Cas9-DNA product. (FIG. 2D) Challenge DNA anneals to the uncut non-target strand when Cas9 nuclease domains are inactivated. EMSA performed as described in FIG. 2A. Cas9, Cas9D10A, Cas9H840A, and dCas9 nuclease variants were used as diagrammed. Open triangle, RNP-DNA; solid black triangle, supershifted product. (FIG. 2E) Challenge DNA anneals to the non-target strand when strand displacement is prevented by adjacent Cas9-DNA interactions in a PAM-Out orientation. EMSA performed as described in FIG. 2A, except the fluorophore location was varied. Cas9 and dCas9 nuclease variants were used as diagrammed. D1 substrate dsDNA was labeled with Cy5 on the + strand (solid square) or Cy3 on the − strand (open square). Challenge ssDNAs were labeled with Cy5 on the + strand (solid circle) or Cy3 on the − strand (open circle). Open triangle, RNP-DNA; Solid black arrow, well-shifted products.

FIG. 6: Schematic of reagents and experimental design for EMSA experiments. Potential supershift products are presented where appropriate.

Figure 7C:
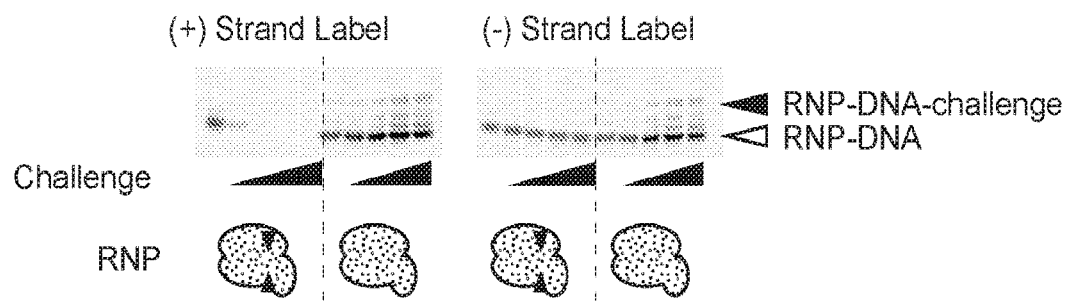

FIG. 7: (FIG. 7A) The non-target strand is released on the PAM-distal side of the cut. One Cas9 molecule was loaded onto substrate DNA fluorescently labeled at the 5' or the 3' terminus of each strand (FIG. 6). Only the 5' non-target strand can be removed from the complex by a challenge DNA. Open arrow, RNP-DNA complex. (FIG. 7B) Removal of the non-target strand depends upon the concentration of the challenge DNA but is independent of the labeling fluorophore. Single RNP EMSA was conducted as described in FIG. 2A, except challenge concentration was varied from 0-1500 nM (0, 30, 75, 150, 300, 600, 1500 nM). Catalytically inactive dCas9 was used in lane 8 (dashed box) to demonstrate that nuclease activity is required for strand extrusion activity. Substrate DNA fluorescently labeled at the 5' termini with Cy5 or Cy3 as indicated. Open arrow, RNP-DNA complex. (FIG. 7C) Strand annealing occurs in single-RNP substrates when the non-target strand is left intact. Cas9 or dCas9 variants were loaded onto substrate DNA as indicated and as described in FIG. 6. Challenge concentration was varied from 0-5 uM (0, 500, 1500, 2500, 5000 nM). Open arrow, RNP-DNA complex; solid black arrow, supershifted products.

FIG. 8: Model for challenge-mediated non-target strand removal activity. 1) After duplex cleavage, Cas9 holds onto three ends of the target DNA (white crossed circles), but the PAM-distal non-target strand is released from the Cas9-DNA complex. 2) Complementary DNA anneals to released strand. 3) Branch migration results in extrusion from the Cas9-DNA complex.

Figure 9:
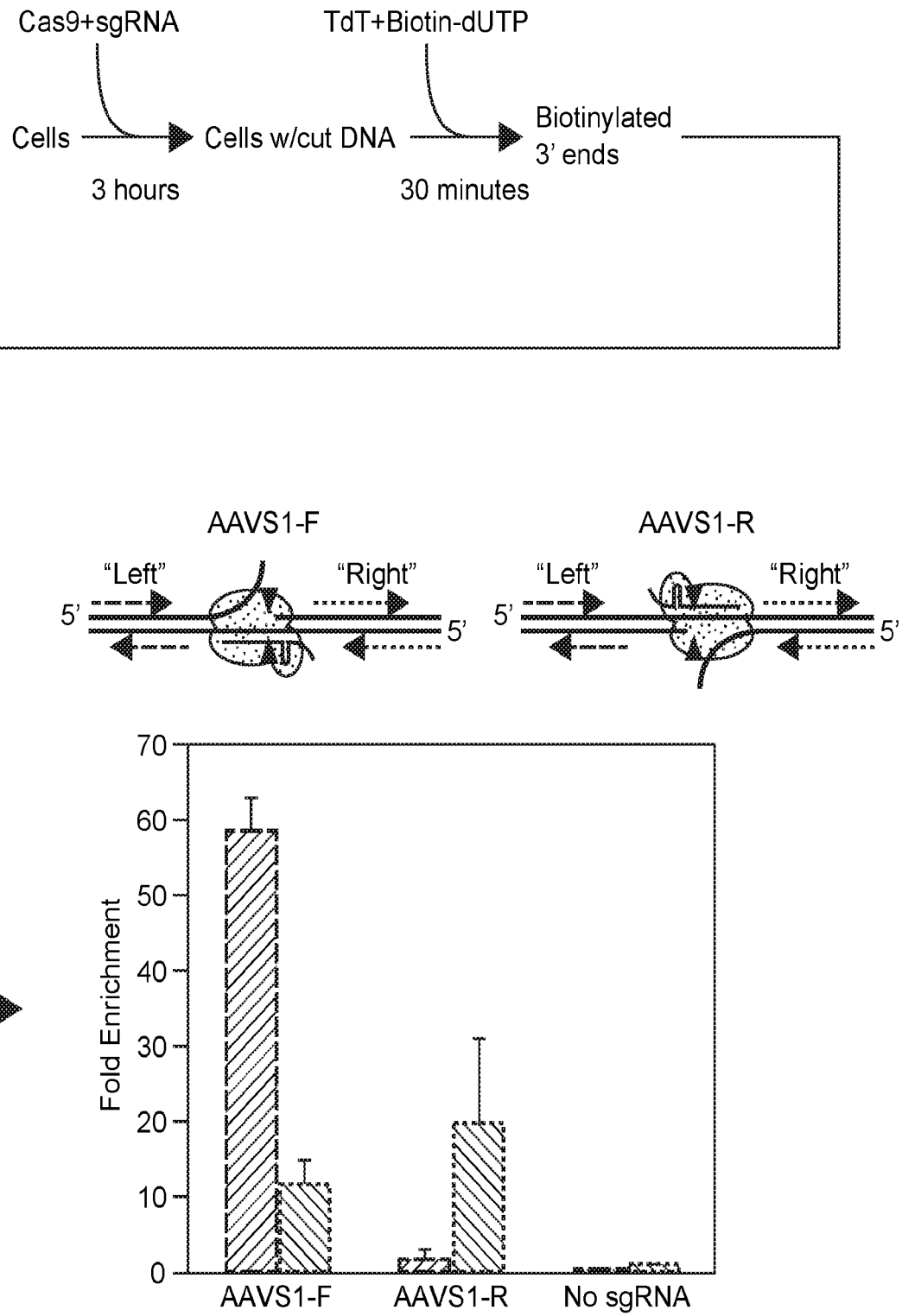
FIG. 9 depicts that the non-target strand is available for enzymatic modification in cells.

To determine whether Cas9 asymmetrically releases DNA during in vivo gene targeting in human cells, a terminal transferase end-labeling assay was used to measure the accessibility of the 3'-hydroxyls on either side of a Cas9-induced double stranded break immediately after cleavage. It was found that the non-target strand is PAM-distally end-labeled six-fold more effectively than the target strand, and this preferential labeling follows the orientation of the Cas9 complex, such that sgRNAs targeting opposite strands induce labeling of opposite hydroxyls (FIG. 9). Preferential accessibility of a single strand at the site of a Cas9 break raises the possibility that single strand break recognition may play an unanticipated role in Cas9-mediated genome editing.

FIG. 9: The non-target strand is available for enzymatic modification in cells. Cas9 was targeted to either strand of the AAVS1 locus (AAVS1-F or AAVS1-R) and terminal transferase was introduced to 3' end-label cut DNA with biotin. After streptavidin immunoprecipitation, end-labeling on either side of the break was determined by the ability to qPCR amplify sequences using the indicated primer pairs (Left and Right). Results are presented as the mean+/−SD fold enrichment (n=3) of labeled DNA over uncut control DNA (ACT1).

Figure 2D:
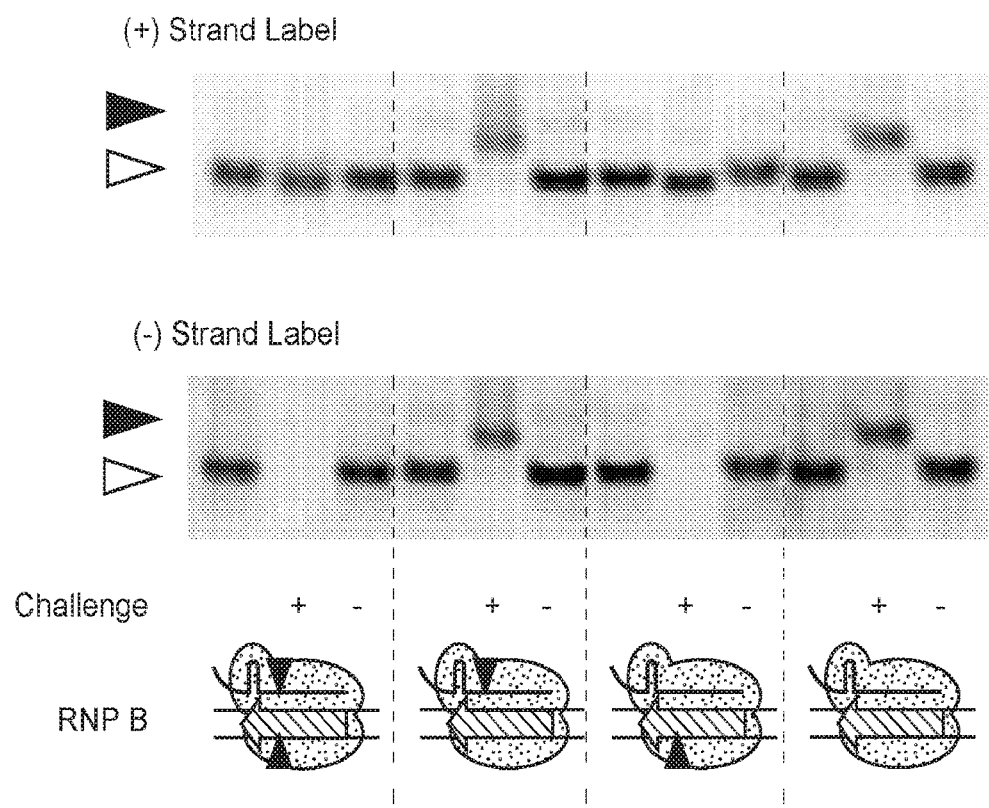
Figure 2E:
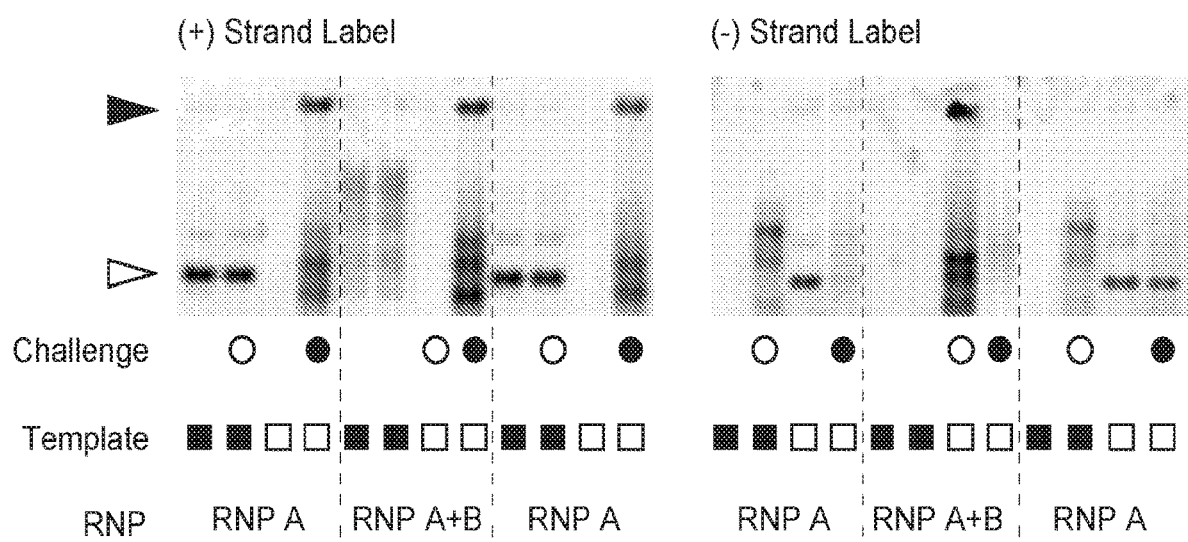

Having shown that Cas9 releases the PAM-distal non-target strand but tightly engages the other three strands, the nature of complexes formed when strand extrusion is prevented was explored, either by catalytic inactivation of nuclease domains or by topological prevention of branch migration. Combining substrate DNA with Cas9 or the Cas9H840A mutant, which both cut the non-target strand, preserved the challenge-dependent removal of the non-target strand. The Cas9D10A mutant and dCas9, which leave the non-target strand intact, instead exhibited a supershifted product when provided with target strand challenge. This is consistent with stable annealing of the ssDNA challenge to the non-target strand and formation of a Cas9-dsDNA-ssDNA complex (FIG. 2D and FIG. 7C). This model predicts that loading two RNPs onto a single substrate DNA in a PAM-Out orientation should prevent strand removal by branch migration because the stable protein-DNA interaction on the PAM-proximal side of each RNP would topologically block branch migration from the other complex (FIG. 6). This may be similar to the situation encountered during genomic targeting with even a single Cas9 nuclease, in which chromatin factors such as nucleosomes should prevent branch migration. Strand-annealing activity in PAM-Out complexes to directly the monitor incorporation of fluorescently labeled challenge DNA into supershifted products was investigated. For PAM-Out RNPs bound to either strand of the substrate, addition of target strand challenge DNA resulted in retention of the fluorescent challenge in the wells rather than strand removal (FIG. 2E). This is in direct contrast to the PAM-In configuration, which does not present a topological barrier and allows strand removal (FIG. 2C). Taken together, these observations demonstrate that the non-target strand is accessible for annealing to complementary ssDNA even when branch migration is prevented. Cas9 binding therefore not only melts the non-target DNA strand from the target strand, but also renders the non-target strand accessible for annealing to exogenous nucleic acid.

Figure 3A:
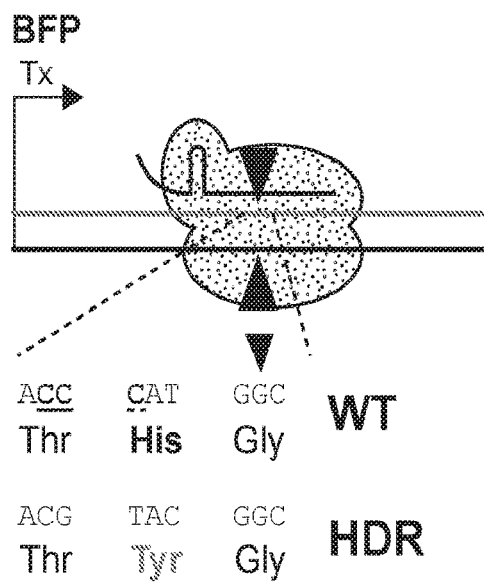
FIG. 3A-3E depicts that delivery of ssDNA donors complementary to the non-target strand drives efficient HDR using Cas9, nickases and dCas9.
Figure 3B:
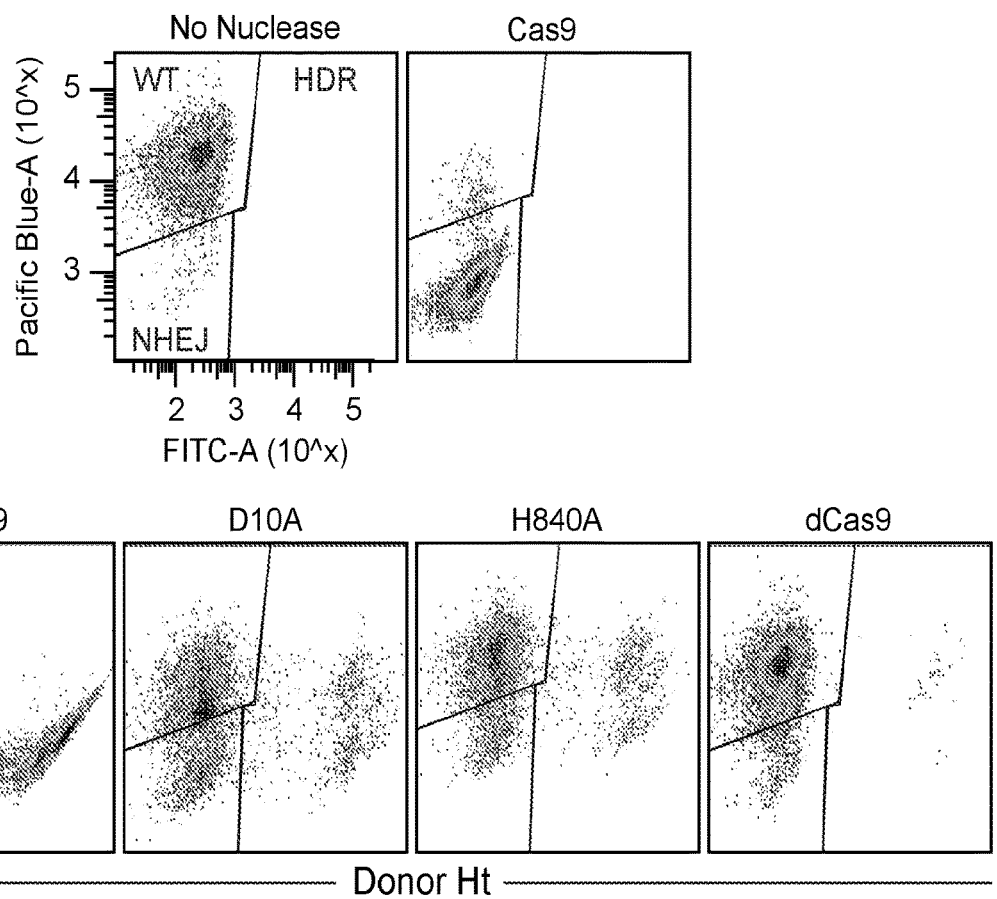
Figure 3C:
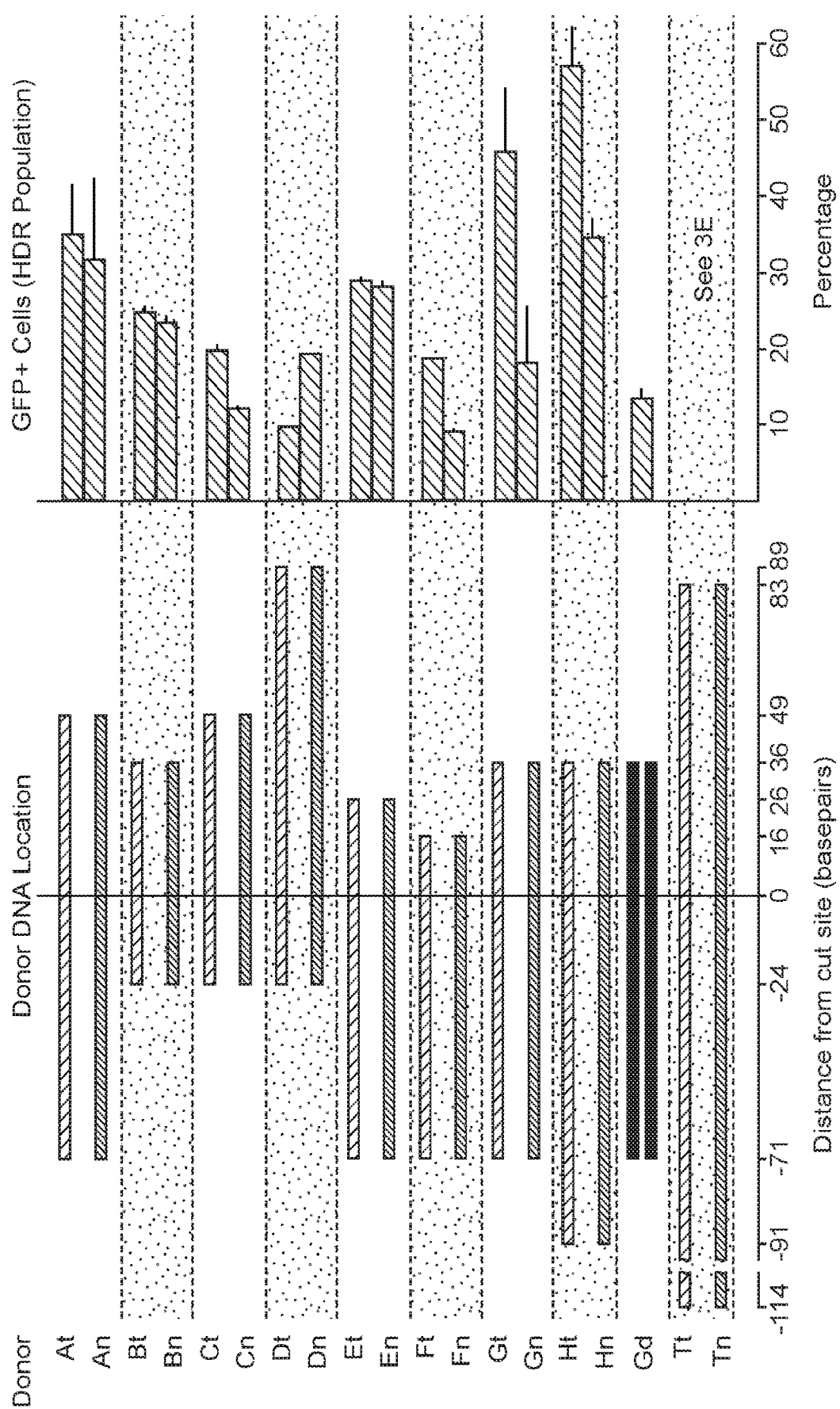
Figure 11:
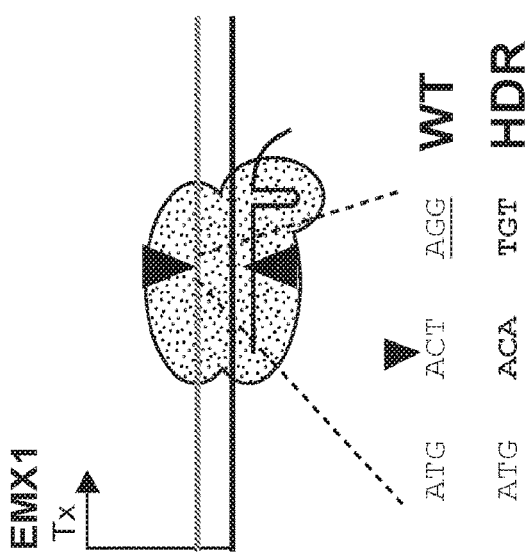
FIG. 11 depicts the strand-bias for optimized donor DNA.
Figure 11:
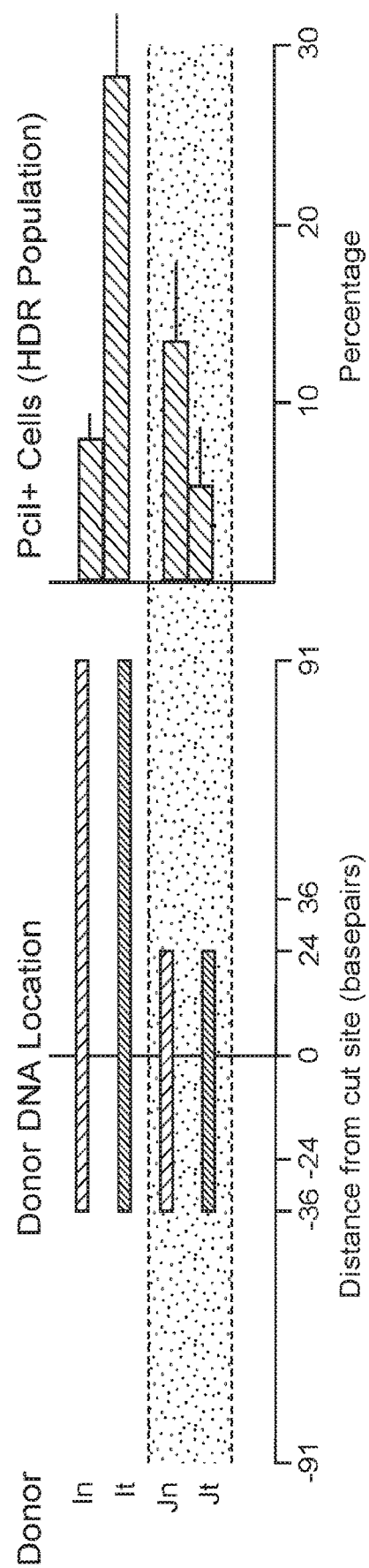

Short ssDNA donors containing a mutation of interest have been used to stimulate homology-directed repair (HDR) events, the frequency of which can be increased by administering cell cycle or DNA damage repair inhibitors[5,14]. It was investigated if designing an ssDNA donor to optimize annealing to the exposed non-target strand could boost the frequency of HDR events in the absence of chemical intervention. To explore this hypothesis, ssDNA donor molecules with varying sequence overlap on the 5' and 3' side of the break and complementary to either the non-target or target strand were generated, and their ability to support Cas9-mediated conversion of a stably-integrated BFP reporter to green fluorescent protein (GFP) via a three nucleotide mutation was measured (FIG. 3A-FIG. 3B). Nucleofection of Cas9 RNPs with a donor DNA complementary to the non-target strand stimulated HDR frequencies up to 2.6 fold greater than donor DNA complementary to the target strand and 4 fold greater than double strand donor DNA of the same length (FIG. 3C). Strikingly, asymmetric donor DNA optimized for annealing by overlapping the Cas9 cut site with 36 base pairs on the PAM-distal side, and with a 91 base pair extension on the PAM-proximal side of the break, supported HDR frequencies of 57±5%. This HDR frequency, obtained through simple rules of ssDNA donor design, is several fold greater than rates obtained using potentially undesirable chemical or genetic intervention, such as cell cycle blockade or knockdown of non-homologous end joining (NHEJ) repair[3,6]. Shorter or longer overlaps with the non-target strand compromised editing efficiency, possibly by reducing the stability of annealing to the non-target strand or requiring extensive invasion into the duplex region further away from the Cas9 complex. Donor DNA complementary to the non-target strand designed using these rules also increased HDR frequencies at the endogenous EMX1 locus (FIG. 11 and FIG. 12). Notably, while the geometric design principles used for increased HDR at EMX1 remained consistent with annealing to the non-target strand, the strandedness and polarity of the targeting sgRNA and hence the donor ssDNA are opposite those used when editing the exogenous BFP construct. Thus, HDR enhancement by precise donor-non-target strand complementarity appears robust to the choice of transcript template or coding strand.

FIG. 3: Delivery of ssDNA donors complementary to the non-target strand drives efficient HDR using Cas9, nickases, and dCas9. (FIG. 3A) Schematic for HDR at a BFP reporter locus. Target strand (green) or non-target strand (magenta) donor ssDNAs were generated with the indicated overlaps on either side of the Cas9 cut site in the BFP reporter. The sequences of the unedited (wild type (WT), BFP) and edited loci (HDR, GFP) are presented inset (PAM reverse-complement, underlined; cut site, magenta arrow). (FIG. 3B) HDR, NHEJ, and unedited populations can be measured using flow cytometry. BFP-GFP flow cytometry scatter plots for BFP reporter cells (leftmost panel), BFP reporter cells edited with Cas9 (Cas9), or BFP reporter cells edited with the indicated nuclease and Donor Ht. Data shown is representative of n=2 experiments. Gated populations are WT, BFP+ cells; NHEJ, BFP– GFP– cells; and HDR, GFP+ cells. (FIG. 3C) Optimized donor DNA is complementary to the non-target strand and has a characteristic size. HDR frequencies for editing with target (t), non-target (n), or double-stranded (d) donor DNAs are presented at right as mean±SD for n≥2 independent experiments. (FIG. 3D) Target strand donor stimulates greater levels of HDR for all Cas9 variants. HDR frequencies quantified from editing experiments using the indicated nuclease and donor Donor Ht (target strand, green) or Donor Hn (non-target strand, magenta). Data is presented as mean±SD from n≥2 independent experiments. (FIG. 3E) Single or tiled-dCas9 molecules support HDR. HDR frequencies from dCas9 editing experiments as presented in FIG. 3D, except control (RNP only, Donor only) reactions are shown alongside editing reactions. RNP, single dCas9; tiled, equimolar amounts of dCas9 targeting four distinct sites on the coding strand of the BFP reporter.

FIG. 11: Strand-bias for optimized donor DNA is independent of genomic locus and gene transcription. Cas9 targets the template strand of the EMX1 locus as diagrammed at left. Target strand (blue) or non-target strand (orange) donor ssDNAs were generated with the indicated overlaps on either side of the Cas9 cut site at EMX1. The sequences of the unedited and edited loci are presented inset (PAM sequence, underlined; cut site, magenta arrow; PciI site, bold font). HDR frequencies for editing with each donor are presented at right as mean+/–SD for n≥2 two independent experiments.

Figure 12A:
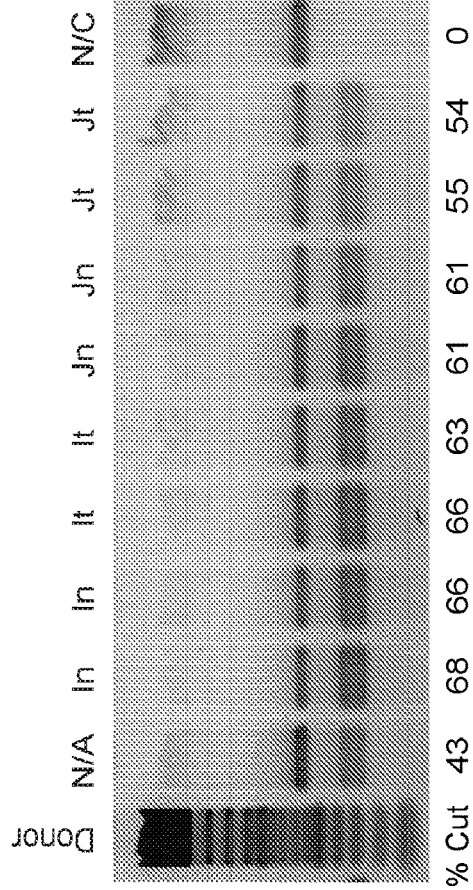
FIG. 12A-12B depicts various conditions affecting the cutting of loci.
Figure 12B:
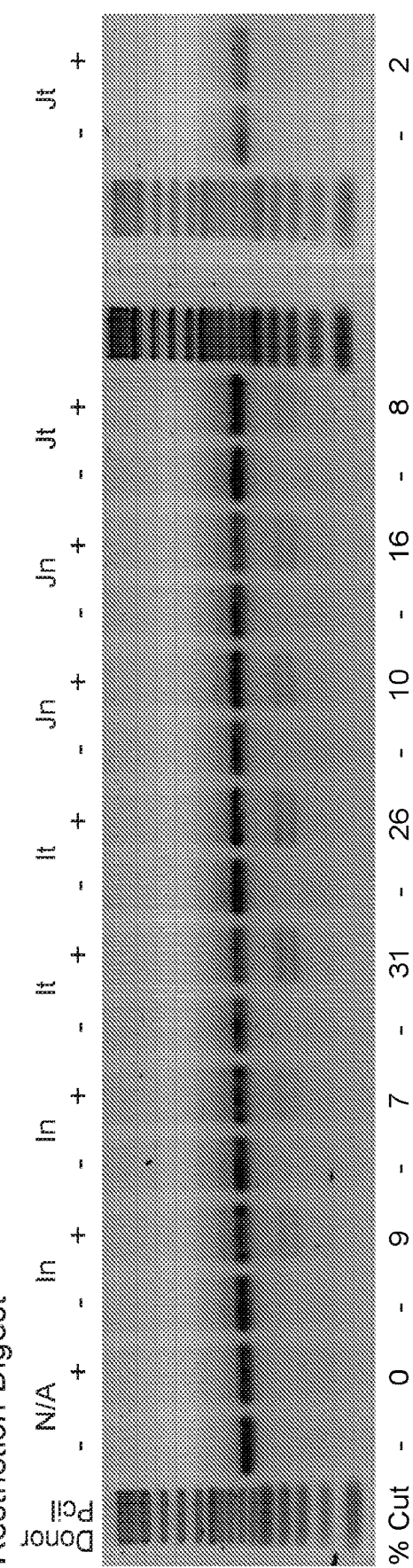

FIG. 12: (FIG. 12A) The EMX1 locus is not cut as efficiently as the BFP locus. PCR amplification and T7E1 digestion were performed on cells edited using the indicated donor DNA (N/A—no donor, N/C—no Cas9). % Cut was quantified by gel densitometry. Compare to 95% total editing seen at the BFP locus (FIG. 10A). (FIG. 12B) HDR incorporation of a PciI site into the EMX1 locus shows donor strand-bias. PCR amplification (–) or PCR amplification and PciI digestion (+) was performed on cells edited using the indicated donor DNA (N/A—no donor). % Cut was quantified by gel densitometry and used to generate bar graphs in FIG. 11.

Figure 3E:
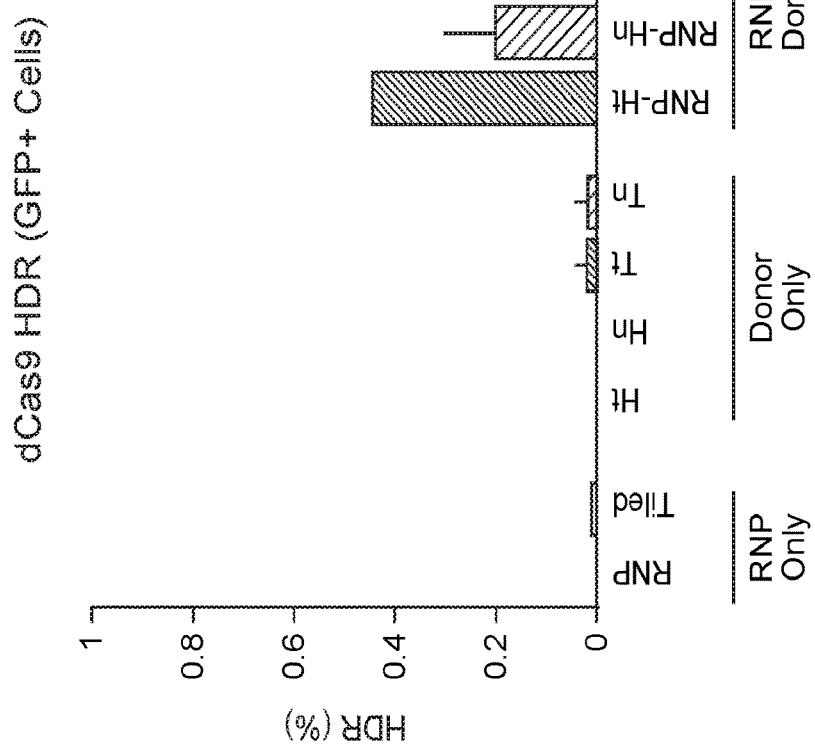
Figure 3D:
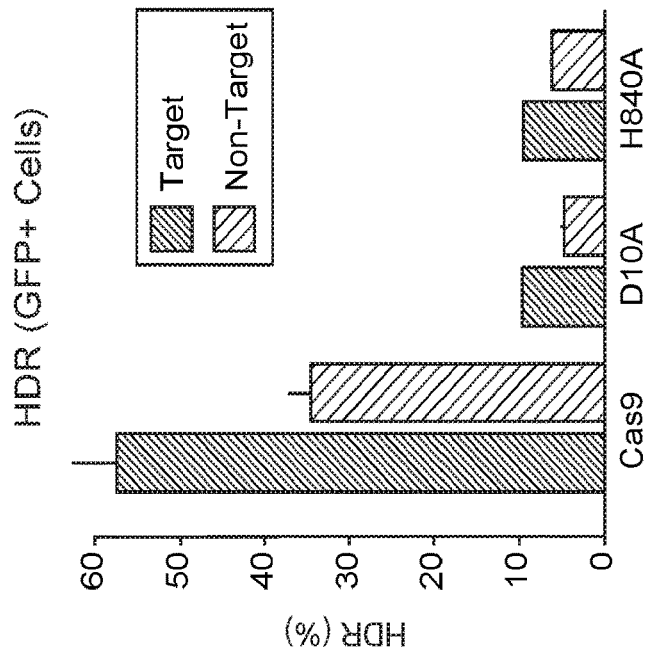
Figure 4:
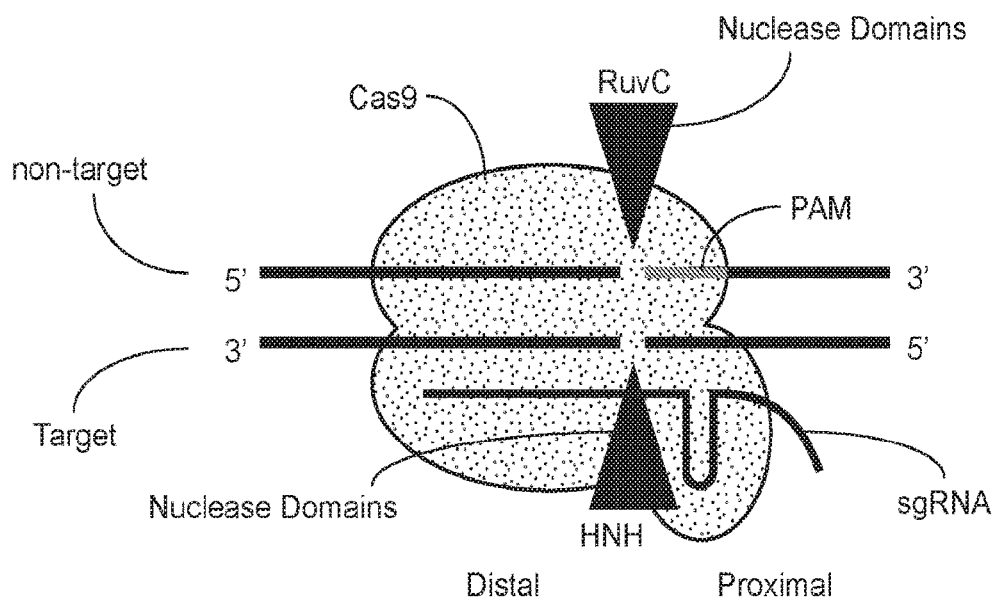
FIG. 4 depicts a schematic of Cas9's interaction with substrate DNA.

Because it was observed that in vitro strand annealing is independent of nuclease activity (FIG. 2), the potential of optimized ssDNA donors to edit the BFP reporter when paired with Cas9 variants in which one or both nuclease domains were disrupted was investigated. Cas9D10A stimulates 2-3% HDR when delivered via plasmid in a "paired nick" configuration[16,17] but efficient HDR with a single nickase has not been reported[18]. Using RNP electroporation, it was observed that Cas9D10A (nicking the target strand) and Cas9H840A (nicking the non-target strand) each stimulated HDR frequencies of ~10% when provided with target strand donor DNA, but also silenced the BFP reporter, potentially by inducing error-prone NHEJ (FIG. 3B, FIG. 3D and FIG. 10A). This latter observation raises concerns about the use of paired nickases for editing, since off-target cuts associated with each single nickase could be mutagenic. The high efficiency of editing with RNP delivery relative to plasmid delivery may reveal these unappreciated NHEJ events, since indels caused by individual plasmid-expressed nickases have previously been reported at the low end of the detection level for T7E1 or Surveyor assays[8,16,17] Surprisingly, a small but measurable (0.4±0.0%) frequency of HDR was observed when catalytically inactive dCas9 was used in editing experiments (FIG. 3B and FIG. 3D). dCas9 was less effective at stimulating HDR than Cas9, Cas9D10A, or Cas9H840A but presumably stimulates editing without introducing breaks in genomic DNA (FIG. 10A). For all nuclease variants tested, HDR occurred at approximately a two-fold higher frequency when donor DNA complementary to the non-target strand was provided relative to donor DNA complementary to the target strand (FIG. 3D), suggesting that strand annealing impacts HDR in the absence of nuclease activity, consistent with the ability to stably form Cas9-dsDNA-ssDNA complexes in vitro (FIG. 2D, FIG. 2E and FIG. 7C).

Figure 10B:
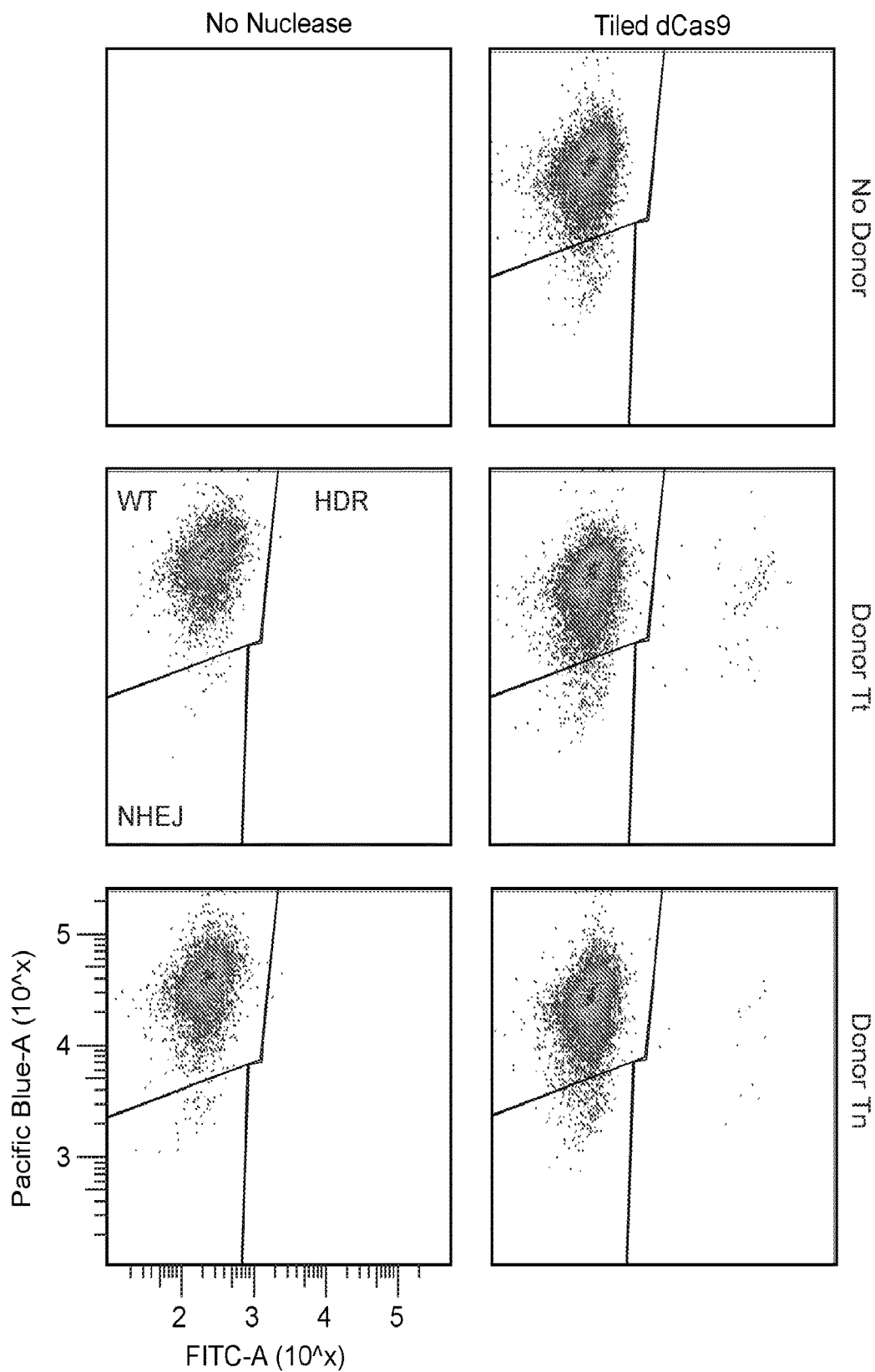

FIG. 10: (FIG. 10A) Representative flow cytometry data used to create bar graphs shown in FIG. 3B. (FIG. 10B) Representative flow cytometry data used to create bar graphs shown in FIG. 3C.

dCas9-mediated HDR is reminiscent of reports of ODN-mediated repair[19], in which single stranded donor DNA invades uncut genomic duplex and provides a template for conversion. As the annealing step is thought to be rate limiting in ODN-mediated repair, it was speculated that binding multiple dCas9 molecules to the same strand would displace large portions of genomic DNA for annealing to the ssDNA donor and might increase the frequency of dCas9-mediated HDR. Tiling four dCas9 molecules on the same strand resulted in 2-fold increase (to 0.7±0.3%) in HDR when paired with an ssDNA donor that can anneal to the non-target strand, but a 2-fold decrease (0.2±0.04%) when paired with a non-annealing donor (FIG. 3E and FIG. 10B).

The rate of dCas9-mediated HDR, while low compared to wild type Cas9-mediated mutation, is substantially greater than oligonucleotide alone (0.02±0.03%; FIG. 3E). dCas9-mediated mutation could be useful in therapeutic applications where cleavage at target or off-target sites stimulates undesirable NHEJ events.

Figure 13:
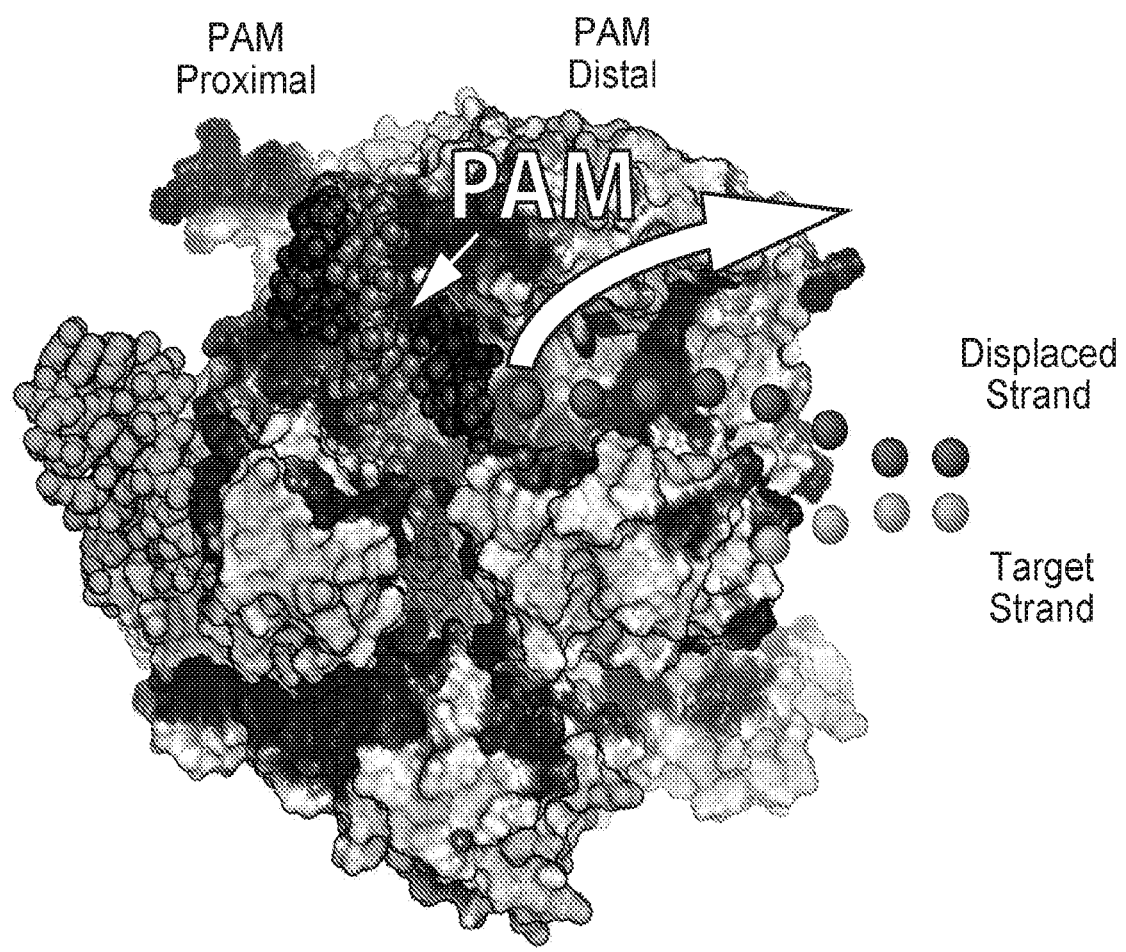
FIG. 13 depicts structural data that is consistent with the asymmetric release of substrate by Cas9.

Cas9 is an antiviral restriction enzyme that has rapidly been adopted as a tool for gene editing, but relatively little is known about the steps that occur between genome cleavage and subsequent repair. It was demonstrated that although Cas9 binds stably to DNA substrates, it makes one strand upstream of the PAM and identical in sequence to the RNA protospacer accessible both in vitro and in vivo. Cas9-mediated interrogation of potential Clustered Regularly Interspaced Short Palindromic Repeat (CRISPR) targets has recently been shown to play a role in protospacer acquisition by Cas1, Cas2, and Csn2[20], and it is tempting to speculate that Cas9's ability to render the non-target strand available for annealing to exogenous factors could potentiate this process. The ability of Cas9 to release one PAM-distal strand of DNA is consistent with recently published structural data showing that the target DNA strand is buried from solvent and wrapped around the sgRNA, whereas the RuvC active site lines a wide, solvent-exposed basic cleft that appears poised to channel the PAM-distal region of the non-target strand (FIG. 13). This structural asymmetry also explains an early observation that Cas9 cleaves the target strand in one precise location 3 base pairs from the PAM while the non-target strand is cut in variable locations[16], likely because the strand is free to breathe in and out of the nuclease domain. Collectively, the biochemical and structural asymmetry of Cas9 interaction with substrate DNA indicate that Cas9 is not conceptually equivalent to other targeted nucleases such as zing finger nucleases (ZFNs) or transcription activator-like effector nucleases (TALENS), which have symmetric FokI catalytic sites and have not been observed to preferentially release one strand of DNA. Thus, strategies for Cas9-mediated editing may differ from those used with other gene-editing tools, and may even differ for engineered dCas9-FokI editing[21].

FIG. 13: Structural data is consistent with asymmetric release of substrate by Cas9. A surface electrostatic view of Cas9, sgRNA (orange), and non-target (purple) or target (grey) DNA strands[7]. PAM-Cas9 interaction, white arrow; putative path of non-target strand, purple dots; presumed direction of non-target strand extrusion, black arrow.

Most optimization of genome editing has focused on biasing nuclease-based editing towards HDR and away from NHEJ by chemically or genetically inactivating components of the NHEJ pathway, chemically activating HDR, or manipulating the cell cycle[3-6]. These trans interventions, while highly useful in some contexts, may be undesirable during therapeutic gene editing because they diminish the cellular capacity to respond to damage at other sites in the genome. It was found that Cas9-mediated HDR frequencies can be increased by rationally designing the orientation, polarity, and length of the donor ssDNA to match the properties of the Cas9-DNA complex. It was also found that these donor designs paired with tiled catalytically-inactive dCas9 molecules could stimulate HDR approximately 50-fold greater than donor alone. It is currently unclear whether the enhancement of HDR with either Cas9 or dCas9 occurs via a direct mechanism (e.g. mimicking a specific HDR intermediate structure that is recognized by the cell), or indirectly (e.g. increasing the local concentration of the repair template). Simple strategies discovered here will be valuable for basic research and therapeutic gene editing applications, for example correcting a disease causing allele to the wild type sequence.

REFERENCES

1 Doudna, J. A. & Charpentier, E. Genome editing. The new frontier of genome engineering with CRISPR-Cas9. *Science* (New York, N.Y.) 346, 1258096, doi:10.1126/science. 1258096 (2014).

2 Jiang, W. & Marraffini, L. A. CRISPR-Cas: New Tools for Genetic Manipulations from Bacterial Immunity Systems. *Annual review of microbiology,* doi:10.1146/annurev-micro-091014-104441 (2015).

3 Chu, V. T. et al. Increasing the efficiency of homology-directed repair for CRISPR-Cas9-induced precise gene editing in mammalian cells. *Nature Biotechnology,* doi: 10.1038/nbt.3198 (2015).

4 Davis, L. & Maizels, N. Homology-directed repair of DNA nicks via pathways distinct from canonical double-strand break repair. *Proceedings of the National Academy of Sciences of the United States of America* 111, E924-932, doi: 10.1073/pnas. 1400236111 (2014).

5 Lin, S., Staahl, B. T., Alla, R. K. & Doudna, J. A. Enhanced homology-directed human genome engineering by controlled timing of CRISPR/Cas9 delivery. *eLife* 4, doi: 10.7554/eLife.04766 (2014).

6 Maruyama, T. et al. Increasing the efficiency of precise genome editing with CRISPR-Cas9 by inhibition of non-homologous end joining. *Nature Biotechnology,* doi: 10.1038/nbt.3190 (2015).

7 Anders, C., Niewoehner, O., Duerst, A. & Jinek, M. Structural basis of PAM-dependent target DNA recognition by the Cas9 endonuclease. *Nature* 513, 569-573, doi:10.1038/nature13579 (2014).

8 Nishimasu, H. et al. Crystal structure of Cas9 in complex with guide RNA and target DNA. *Cell* 156, 935-949, doi:10.1016/j.cell.2014.02.001 (2014).

9 Jinek, M. et al. A programmable dual-RNA-guided DNA endonuclease in adaptive bacterial immunity. *Science* (New York, N.Y.) 337, 816-821, doi:10.1126/science.1225829 (2012).

Carroll, D. Genome engineering with zinc-finger nucleases. *Genetics* 188, 773-782, doi:10.1534/genetics.111.131433 (2011).

11 Gaj, T., Gersbach, C. A. & Barbas, C. F. ZFN, TALEN, and CRISPR/Cas-based methods for genome engineering. *Trends in biotechnology* 31, 397-405, doi:10.1016/j.tibtech.2013.04.004 (2013).

12 Sternberg, S., Redding, S., Jinek, M., Greene, E. & Doudna, J. DNA interrogation by the CRISPR RNA-guided endonuclease Cas9. *Nature* (2014).

13 Abdiche, Y., Malashock, D., Pinkerton, A. & Pons, J. Determining kinetics and affinities of protein interactions using a parallel real-time label-free biosensor, the Octet. *Analytical biochemistry* 377, 209-217, doi:10.1016/j.ab.2008.03.035 (2008).

14 Kim, S., Kim, D., Cho, S. W., Kim, J. & Kim, J.-S. Highly efficient RNA-guided genome editing in human cells via delivery of purified Cas9 ribonucleoproteins. *Genome Research* 24, 1012-1019, doi:10.1101/gr.171322.113 (2014).

Metzger, L. & Iliakis, G. Kinetics of DNA double-strand break repair throughout the cell cycle as assayed by pulsed field gel electrophoresis in CHO cells. *International journal of radiation biology* 59, 1325-1339 (1991).

16 Ran, F. A. et al. Double nicking by RNA-guided CRISPR Cas9 for enhanced genome editing specificity. *Cell* 154, 1380-1389, doi:10.1016/j.cell.2013.08.021 (2013).
17 Mali, P. et al. CAS9 transcriptional activators for target specificity screening and paired nickases for cooperative genome engineering. *Nature Biotechnology* 31, 833-838, doi:10.1038/nbt.2675 (2013).
18 Trevino, A. E. & Zhang, F. *Genome Editing Using Cas9 Nickases*. 1 edn, Vol. 546 (Elsevier Inc., 2014).
19 Engstrom, J. U., Suzuki, T. & Kmiec, E. B. Regulation of targeted gene repair by intrinsic cellular processes. *BioEssays: news and reviews in molecular, cellular and developmental biology* 31, 159-168, doi:10.1002/bies.200800119 (2009).
Heler, R. et al. Cas9 specifies functional viral targets during CRISPR-Cas adaptation. *Nature* 519, 199-202, doi: 10.1038/nature14245 (2015).
21 Tsai, S. Q. et al. Dimeric CRISPR RNA-guided FokI nucleases for highly specific genome editing. *Nature Biotechnology* 32, 569-576, doi:10.1038/nbt.2908 (2014).
22 Anders, C. & Jinek, M. In vitro enzymology of Cas9. *Methods in enzymology* 546, 1-20, doi:10.1016/B978-0-12-801185-0.00001-5 (2014).
23 Aparicio, O. et al. Chromatin immunoprecipitation for determining the association of proteins with specific genomic sequences in vivo. *Current protocols in molecular biology*/edited by Frederick M Ausubel [et al] Chapter 21, Unit 21.23, doi:10.1002/0471142727.mb2103s69 (2005).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11085057B2). An electronic copy of the "Sequence Listing" will also be available from the USPTO upon request and payment of the fee set forth in 37 CFR 1.19(b)(3).

What is claimed is:

1. A method of editing genomic DNA of a eukaryotic cell, wherein the genomic DNA comprises a target strand and a non-target strand, the method comprising introducing into the cell:
   (a) a Cas9 guide RNA, or one or more nucleic acids encoding said Cas9 guide RNA, wherein the Cas9 guide RNA hybridizes to a target sequence of the target strand of the genomic DNA;
   (b) an asymmetric double stranded or single stranded donor DNA molecule comprising a 5' homology arm and a 3' homology arm, wherein the 3' homology arm is 20 to 50 nucleotides in length, is shorter than the 5' homology arm, and comprises at least 10 consecutive nucleotides of said target sequence, and wherein the ratio of the length of the 5' homology arm to the 3' homology arm is from 2.5:1 to 5:1; and
   (c) a Cas9 protein or a nucleic acid encoding said Cas9 protein,
   wherein (i) the Cas9 protein forms a complex with the Cas9 guide RNA thereby guiding the Cas9 protein to said target sequence, (ii) the 3' homology arm of the donor DNA molecule hybridizes to the non-target strand of the genomic DNA, and (iii) a nucleotide sequence of the donor DNA molecule is incorporated into the genomic DNA.

2. The method according to claim 1, wherein the Cas9 protein comprises a functional RuvC domain and cleaves at least the non-target strand of genomic DNA.

3. The method according to claim 1, wherein the Cas9 protein comprises a functional HNH domain and cleaves at least the target strand of genomic DNA.

4. The method according to claim 1, wherein the 5' homology arm of the donor DNA molecule is 50 to 200 nucleotides in length.

5. The method according to claim 1, wherein the donor DNA molecule comprises a heterologous nucleotide sequence, between the 5' and 3' homology arms, that is incorporated into the genomic DNA.

6. The method according to claim 1, wherein the donor DNA molecule comprises one or more synthetic modifications selected from: a base modification, a sugar modification, and a backbone modification.

7. The method according to claim 1, wherein the non-target strand comprises a protospacer-adjacent motif (PAM), wherein the 3' homology arm comprises at least 10 consecutive nucleotides that are complementary to a nucleotide sequence in the PAM-distal non-target strand, and wherein the 5' homology arm does not comprise at least 10 consecutive nucleotides that are complementary to a nucleotide sequence in the PAM-distal non-target strand.

* * * * *